(12) United States Patent
Taylor et al.

(10) Patent No.: US 9,079,967 B2
(45) Date of Patent: *Jul. 14, 2015

(54) MODIFIED CHAPERONIN 10

(71) Applicant: INVION Limited, Seventeen Mile Rocks (AU)

(72) Inventors: Dean Jason Taylor, East Brisbane (AU); Barbara Jane Johnson, Shailer Park (AU); Caroline Amanda Dobbin, Holland Park (AU); Christopher Bruce Howard, Rochedale South (AU); Linda Allison Ward, Carindale (AU)

(73) Assignee: Invion Limited, Seventeen Mile Rocks (AU)

( * ) Notice: Subject to any disclaimer, the term of this patent is extended or adjusted under 35 U.S.C. 154(b) by 0 days.

This patent is subject to a terminal disclaimer.

(21) Appl. No.: 13/970,285

(22) Filed: Aug. 19, 2013

(65) Prior Publication Data

US 2014/0093524 A1    Apr. 3, 2014

Related U.S. Application Data

(62) Division of application No. 13/155,332, filed on Jun. 7, 2011, now Pat. No. 8,513,201, which is a division of application No. 11/991,279, filed as application No. PCT/AU2006/001278 on Aug. 31, 2006, now Pat. No. 7,977,458.

(51) Int. Cl.
*C07K 14/47* (2006.01)
*A61K 38/00* (2006.01)

(52) U.S. Cl.
CPC ............. *C07K 14/47* (2013.01); *C07K 14/4715* (2013.01); *A61K 38/00* (2013.01)

(58) Field of Classification Search
CPC ............................ A61K 38/00; C07K 14/4715
See application file for complete search history.

(56) References Cited

FOREIGN PATENT DOCUMENTS

| WO | 95/15338 A1 | 6/1995 |
|---|---|---|
| WO | 95/15339 A1 | 6/1995 |
| WO | 00/43033 A1 | 7/2000 |
| WO | 03/005036 A2 | 1/2003 |
| WO | 2004/041300 A1 | 5/2004 |
| WO | 2004/076639 A2 | 9/2004 |
| WO | 2005/067959 A1 | 7/2005 |
| WO | 2007/006095 A2 | 1/2007 |

OTHER PUBLICATIONS

S. Carmicle et al., "Proteolytic Sensitivity and Helper T-Cell Epitope Immunodominance Associated with the Mobile Loop in Hsp10s," J. Biol. Chem. 277: 155-160 (2002).

G. Dai et al., "Structural Basis for Helper T-Cell and Antibody Epitope Immunodominance in Bacteriophage T4 Hsp10: Role of Disordered Loops," J. Biol. Chem. 277: 161-168 (2002).

B.J. Johnson et al., "Heat Shock Protein 10 Inhibits Lipopolysaccharide-Induced Inflammatory Mediator Production," J. Biol. Chem. 280: 4037-4047 (2005).

A. Richardson et al., "The Importance of a Mobile Loop in Regulating Chaperonin/Co-Chaperonin Interaction: Humans Versus *Escherichia coli*," J. Biol. Chem. 276: 4981-4987 (2001).

M.J. Somodevilla-Torres et al., Purification and Characterisation of Functional Early Pregnancy Factor Expressed in Sf9 Insect Cells and in *Escherichia coli*, Protein Expression & Purification 32: 276-287 (2003).

K.M. Lin et al., "Myocyte Protection by 10 kD Heat Shock Protein (Hsp10) Involves the Mobile Loop and Attenuation of the Ras GTPase Pathway," FASEB J. 18 1-18 (2004).

*Primary Examiner* — John Ulm
(74) *Attorney, Agent, or Firm* — Ditthavong & Steiner, P.C.

(57) ABSTRACT

The present invention relates to isolated Chaperonin 10 polypeptides possessing immunomodulatory activity, but lacking, or substantially lacking, protein folding activity.

5 Claims, 23 Drawing Sheets

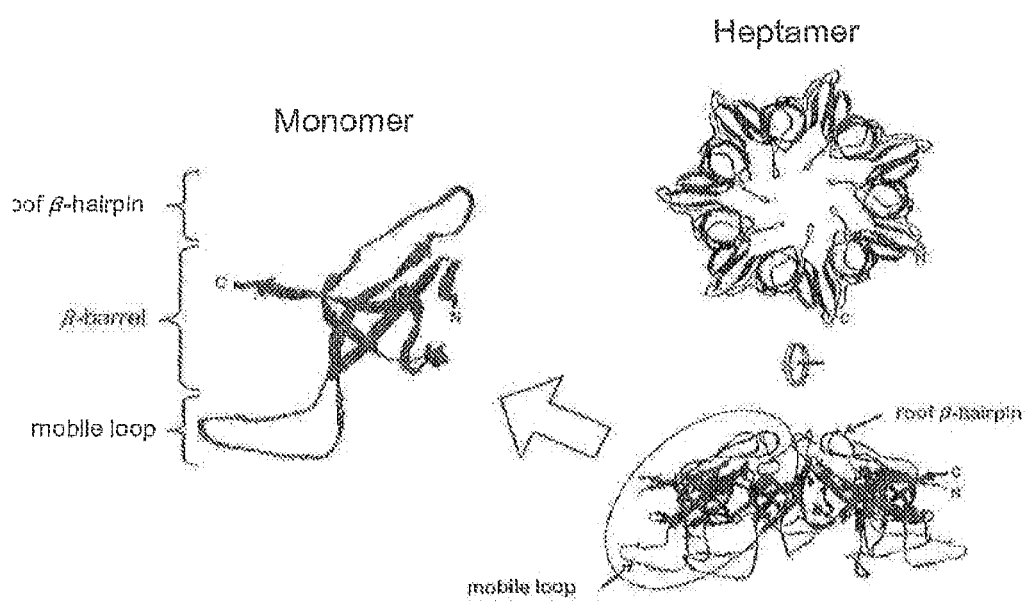

LPS control n=4

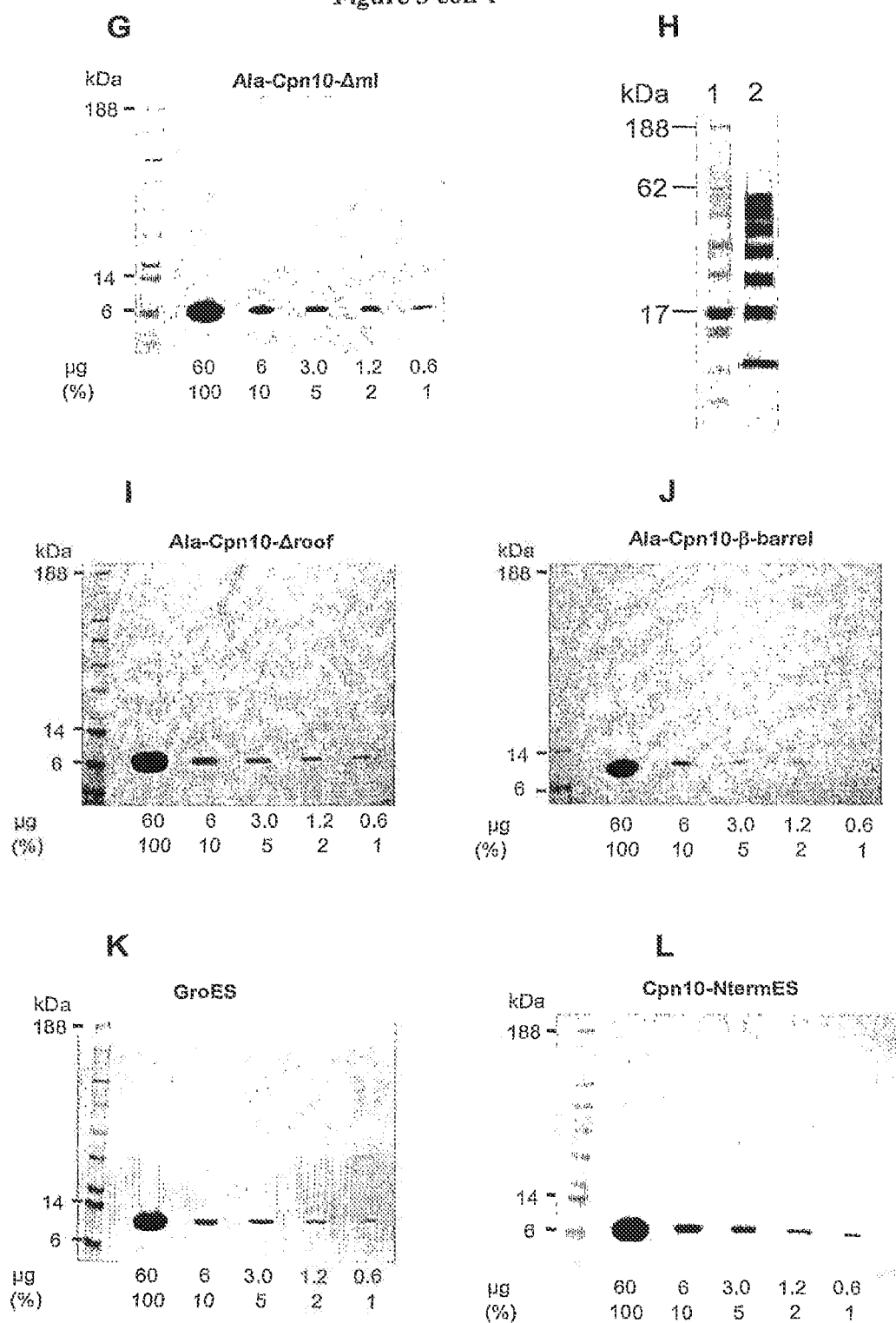

Figure 3 con't
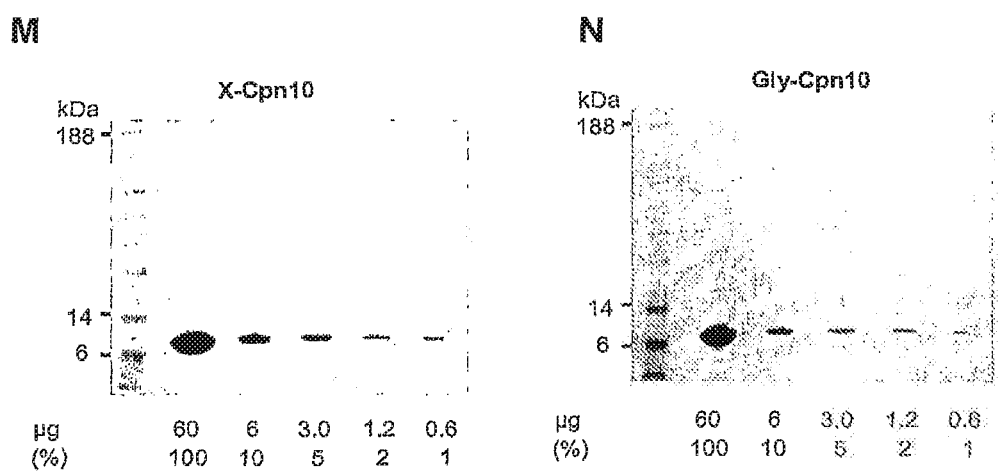

Figure 15
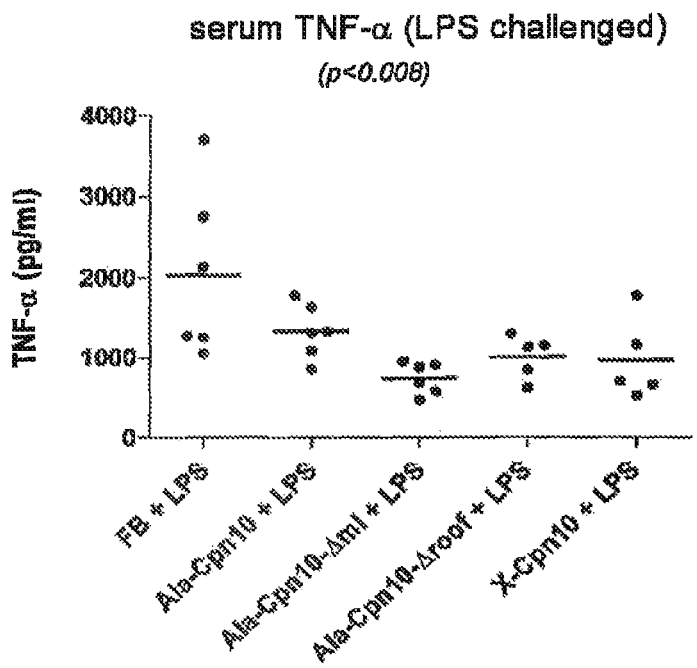
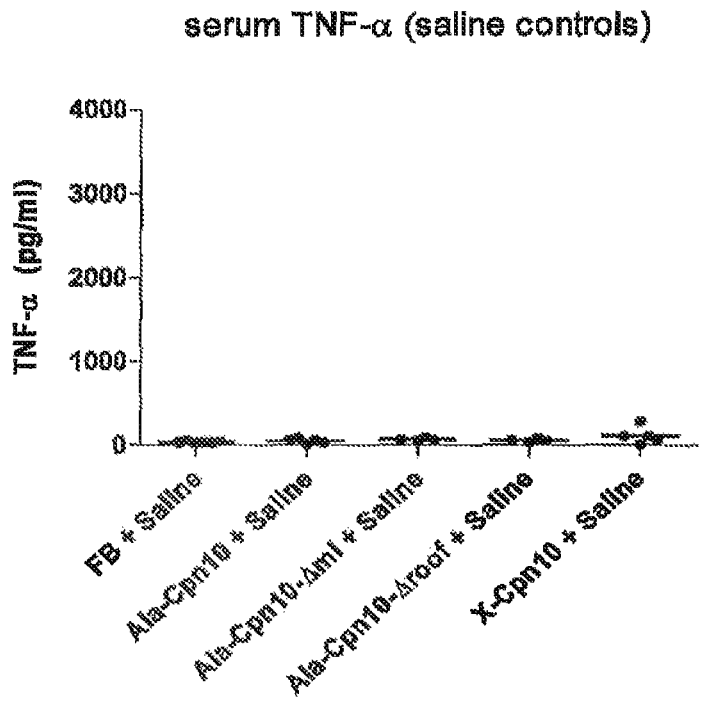

Figure 15 con't
C
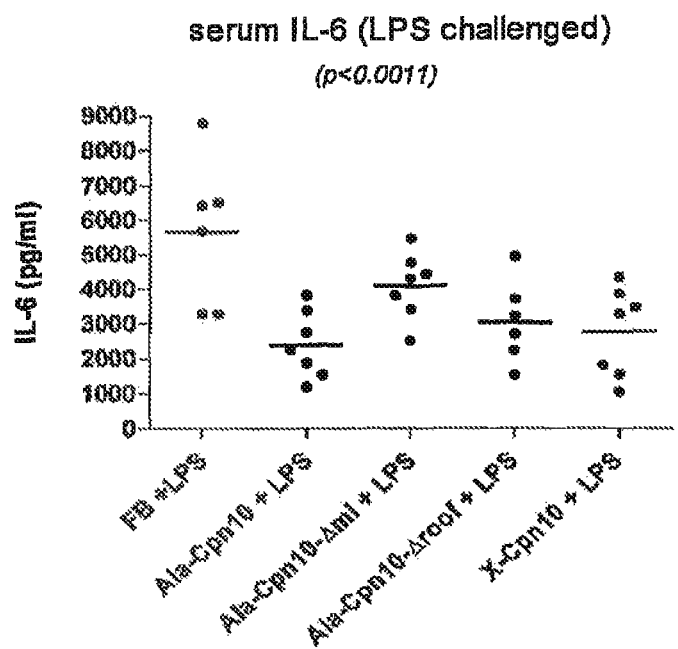
D
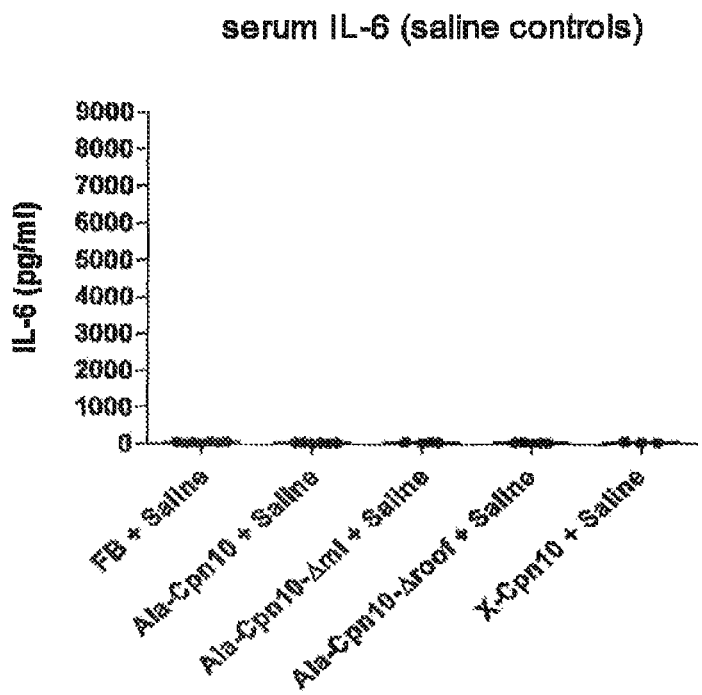

Figure 15 con't
E
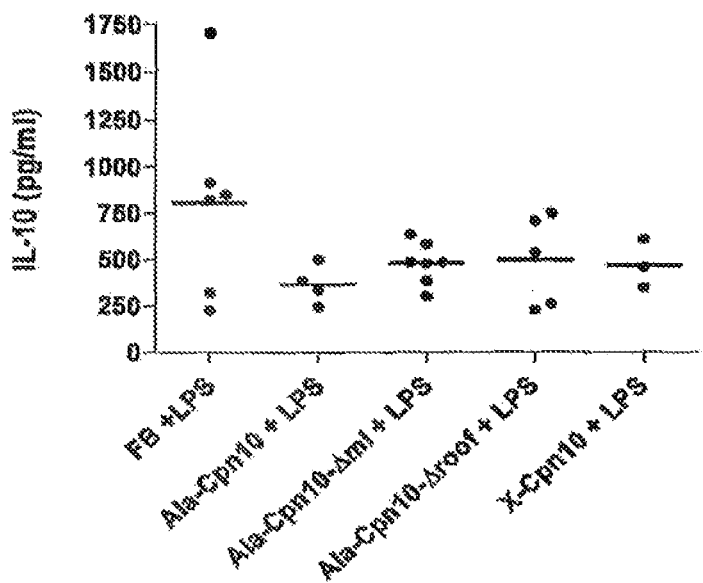
F
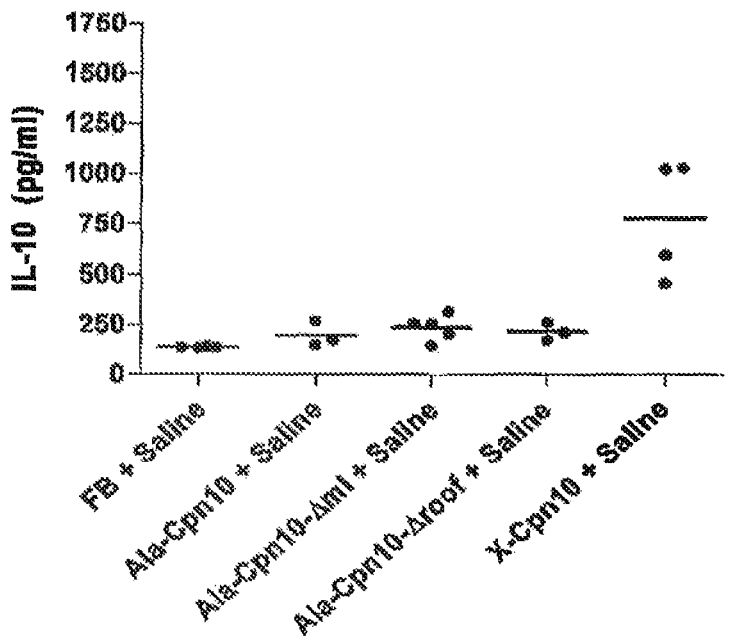

MODIFIED CHAPERONIN 10

CROSS-REFERENCES

This application is a divisional application of U.S. application Ser. No. 13/155,332 by D. J. Naylor et al., entitled "Modified Chaperonin 10" and filed on Jun. 6, 2011, which is a divisional of U.S. application Ser. No. 11/991,279, by D. J. Naylor et al., entitled "Modified Chaperonin 10" and filed on Jan. 16, 2009, now U.S. Pat. No. 7,977,458, which in turn is a United States national stage filing under 35 U.S.C. §371 of PCT Application Serial No. PCT/AU2006/001278 by D. J. Naylor et al., entitled "Modified Chaperonin 10" and filed on Aug. 31, 2006; the specifications of these three applications are incorporated herein in their entirety by this reference.

SEQUENCE LISTING

The instant application contains a Sequence Listing which has been submitted electronically in ASCII format and is hereby incorporated by reference in its entirety. Said ASCII copy, created on Nov. 13, 2014, is named P6854US01_SL.txt and is 52,022 bytes in size.

FIELD OF THE INVENTION

The present invention relates to chaperonin 10 polypeptides, and to nucleic acids encoding the same. The present invention further relates to chaperonin 10 polypeptides displaying immunomodulatory activity, to methods using the same and to compositions comprising such polypeptides.

BACKGROUND ART

Mammalian chaperonin 10 (Cpn10), also known as heat shock protein 10 (Hsp10) and early pregnancy factor (EPF), is typically characterized as a mitochondrial "molecular chaperone" protein involved in protein folding together with chaperonin 60 (Cpn60; Hsp60). Cpn10 and Cpn60 are homologues of the bacterial proteins GroES and GroEL respectively. GroES and Cpn10 each oligomerize into seven member rings that bind as a lid onto a barrel-like structure comprising fourteen GroEL or seven Cpn60 molecules respectively, which tether denatured proteins to the complex (Bukau and Horwich, 1998, *Cell* 92:351-366; Hartl and Hayer-Hartl, 2002, *Science* 295:1852-1858).

Cpn10 proteins are highly conserved across species. Human Cpn10 is 100% identical to bovine Cpn10 and differs from rat Cpn10 at only a single amino acid position. Human Cpn10 shares 30% sequence identity (60% similarity) with GroES from *Escherichia coli*. As illustrated by the heptameric crystal structure of *E. coli* GroES (see FIG. 1A; Xu et al., 1997, *Nature* 388:741-750). Cpn10/GroES proteins are comprised of essentially three different structural regions, an anti-parallel β-barrel region which is flanked by a "roof" β-hairpin loop region and a "mobile loop" region. The mobile loop region mediates interaction with Cpn60/GroEL and is thus critical for the formation of the complex with Cpn60/GroEL and for the "molecular chaperone" protein folding activity.

However in addition to its intracellular role as a molecular chaperone, Cpn10 is also frequently found at the cell surface (see Belles et al., 1999, *Infect Immun* 67:4191-4200) and in the extracellular fluid (see Shin et al., 2003, *J Biol Chem* 278:7607-7616) and is increasingly being recognized as a regulator of the immune response. For example, Cpn10 has been demonstrated to have immunosuppressive activity in experimental autoimmune encephalomyelitis, delayed type hypersensitivity and allograft rejection models (Zhang et al., 2003, *J Neurol Sci* 212:37-46; Morton et al., 2000, *Immunol Cell Biol* 78:603-607).

The present inventors have also recently demonstrated that Cpn10 can inhibit LPS-induced activation of NF-κB, reduce LPS-induced TNFα and RANTES secretion and enhance IL-10 production in a number of different human and murine in vitro systems and murine disease models (Johnson et al., 2005, *J Biol Chem* 280:4037-4047 and International Patent Application No. PCT/AU2005/000041, the disclosure of which is incorporated herein by reference), suggesting that Cpn10 has considerable potential as an immuno-therapeutic for the treatment of autoimmune and inflammatory diseases.

However the site(s) within the Cpn10 molecule responsible for mediating this immunomodulatory activity(ies) has remained elusive.

The present invention relates to modifications to the Cpn10 molecules and the effect of these modifications on immunomodulatory activity.

SUMMARY OF THE INVENTION

Accordingly, the present invention provides Cpn10 polypeptides comprising one or more amino acid substitutions, deletions and/or additions compared to wild-type Cpn10, which polypeptides display immunomodulatory activity.

According to a first aspect of the present invention there is provided an isolated Cpn10 polypeptide possessing immunomodulatory activity but lacking, or substantially lacking, protein folding activity.

According to a second aspect of the present invention there is provided an isolated Cpn10 polypeptide having immunomodulatory activity, said polypeptide comprising one or more amino acid substitutions, deletions and/or additions in the mobile loop region compared to a corresponding wild-type Cpn10 polypeptide.

The Cpn10 polypeptide may display immunomodulatory activity at least similar to the level of immunomodulatory activity of the corresponding wild-type Cpn10 polypeptide.

In one embodiment, one or more residues of the IML tripeptide of the mobile loop region of the Cpn10 polypeptide may be replaced with charged residues.

In another embodiment the Cpn10 polypeptide comprising the IML tripeptide may be replaced with the tripeptide EEE. The Cpn10 polypeptide comprising the EEE tripeptide may be set forth in SEQ ID NO: 39. The Cpn10 polypeptide may be encoded by the nucleotide sequence as set forth in SEQ ID NO:40.

In yet another embodiment the Cpn10 polypeptide comprising the IML tripeptide may be replaced with the tripeptide III. The Cpn10 polypeptide comprising the III tripeptide may be set forth in SEQ ID NO: 37. The Cpn10 polypeptide may be encoded by the nucleotide sequence as set forth in SEQ ID NO:38.

In still yet another embodiment the Cpn10 polypeptide comprising the IML tripeptide may be replaced with the tripeptide IFI. The Cpn10 polypeptide comprising the IFI tripeptide may be set forth in SEQ ID NO: 35. The Cpn10 polypeptide may be encoded by the nucleotide sequence as set forth in SEQ ID NO:36.

According to a third aspect of the present invention there is provided an isolated Cpn10 polypeptide having immunomodulatory activity, said polypeptide substantially lacking the mobile loop region of a corresponding wild-type Cpn10 polypeptide.

In one embodiment the Cpn10 polypeptide substantially lacking the mobile loop region comprises the amino acid sequence as set forth in SEQ ID NO:3 or 24. The Cpn10 polypeptide substantially lacking the mobile loop region may be encoded by the nucleotide sequence as set forth in SEQ ID NO:4, 5 or 25.

The Cpn10 polypeptide may display immunomodulatory activity at least similar to the level of immunomodulatory activity of the corresponding wild-type Cpn10 polypeptide.

According to a fourth aspect of the present invention there is provided an isolated Cpn10 polypeptide having immunomodulatory activity, said polypeptide comprising one or more amino acid substitutions, deletions and/or additions in the roof β-hairpin region compared to a corresponding wild-type Cpn10 polypeptide.

The Cpn10 polypeptide may display immunomodulatory activity at least similar to the level of immunomodulatory activity of the corresponding wild-type Cpn10 polypeptide.

According to a fifth aspect of the present invention there is provided an isolated Cpn10 polypeptide having immunomodulatory activity, said polypeptide substantially lacking the roof β-hairpin region of a corresponding wild-type Cpn10 polypeptide.

In one embodiment the Cpn10 polypeptide substantially lacking the roof β-hairpin region (SEQ ID NO:13) comprises the amino acid sequence as set forth in SEQ ID NO:6 or 26. The Cpn10 polypeptide substantially lacking the roof β-hairpin region may be encoded by the nucleotide sequence as set forth in SEQ ID NO:7, 8 or 27.

The Cpn10 polypeptide may display immunomodulatory activity at least similar to the level of immunomodulatory activity of the corresponding wild-type Cpn10 polypeptide.

According to a sixth aspect of the present invention there is provided an isolated Cpn10 polypeptide having immunomodulatory activity, said polypeptide comprising one or more amino acid substitutions, deletions and/or additions in the mobile loop region and the roof β-hairpin region compared to a corresponding wild-type Cpn10 polypeptide.

According to a seventh aspect of the present invention there is provided an isolated Cpn10 polypeptide, said polypeptide substantially lacking both mobile loop region and the roof β-hairpin region of the corresponding wild-type Cpn10 polypeptide.

The isolated Cpn10 polypeptide may display immunomodulatory activity at least similar to the level of immunomodulatory activity of the corresponding wild-type Cpn10 polypeptide.

In one embodiment the Cpn10 polypeptide comprises the amino acid sequence as set forth in SEQ ID NO:9 or 28. The Cpn10 polypeptide may be encoded by the nucleotide sequence as set forth in SEQ ID NO:10 or 29.

According to an eighth aspect of the present invention there is provided an isolated Cpn10 polypeptide having immunomodulatory activity, said polypeptide comprising a deletion of an extra N-terminal alanine residue compared to a corresponding wild-type Cpn10 polypeptide.

The Cpn10 polypeptide may lack an acetyl group at the N terminus compared to the corresponding wild-type Cpn10 polypeptide. The Cpn10 polypeptide may display a reduced level of immunomodulatory activity when compared to the level of immunomodulatory activity of the corresponding wild-type Cpn10 polypeptide.

In one embodiment the Cpn10 polypeptide comprising the deletion of the extra N-terminal alanine residue may comprise the amino acid sequence as set forth in SEQ ID NO:23.

The Cpn10 polypeptide comprising the deletion of the extra N-terminal alanine residue may be encoded by the nucleotide sequence as set forth in SEQ ID NO:44.

According to a ninth aspect of the present invention there is provided an isolated Cpn10 polypeptide having immunomodulatory activity, wherein the N terminus of the Cpn10 polypeptide is substantially replaced with a bacterial Cpn10 N terminus.

The bacterial Cpn10 may be GroES.

The Cpn10 polypeptide may display a reduced level of immunomodulatory activity when compared to the level of immunomodulatory activity of the corresponding wild-type Cpn10 polypeptide.

In one embodiment the Cpn10 polypeptide may comprise the amino acid sequence as set forth in SEQ ID NO:14. The Cpn10 polypeptide may be encoded by the nucleotide sequence as set forth in SEQ ID NO:43.

According to a tenth aspect of the present invention there is provided an isolated Cpn10 polypeptide having immunomodulatory activity, wherein a glycine residue replaces an extra N terminal alanine residue of the Cpn10 polypeptide as compared to a corresponding wild-type Cpn10 polypeptide.

The Cpn10 polypeptide may display a reduced level of immunomodulatory activity when compared to the level of immunomodulatory activity of the corresponding wild-type Cpn 10 polypeptide.

In one embodiment the Cpn10 polypeptide may comprise the amino acid sequence as set forth in SEQ ID NO:30. The Cpn10 polypeptide may be encoded by the nucleotide sequence as set forth in SEQ ID NO:31.

According to an eleventh aspect of the present invention there is provided an isolated nucleic acid encoding a Cpn10 polypeptide according to any one of the first to the tenth aspects.

According to a twelfth aspect of the present invention there is provided an expression construct comprising a nucleic acid according to the eleventh aspect operably-linked to one or more regulatory sequences.

According to a thirteenth aspect of the present invention there is provided a host cell expressing a polypeptide of any one of the first to tenth aspects, or comprising a nucleic acid of the eleventh aspect or an expression construct of the ninth aspect.

According to a fourteenth aspect of the present invention there is provided an antibody that selectively binds to a polypeptide of any one of the first to the tenth aspects.

According to a fifteenth aspect of the present invention there is provided a pharmaceutical composition comprising a polypeptide of any one of the first to the tenth aspects, a nucleic acid of the eleventh, an expression construct of the twelfth aspect or an antibody of the fourteenth aspect.

The pharmaceutical composition may comprise one or more additional agents. For example, for the treatment of multiple sclerosis the composition may further comprise an effective amount of IFNβ.

According to a sixteenth aspect of the present invention there is provided a method of treating a subject, including the step of administering to said subject an effective amount of a Cpn10 polypeptide of any one of the first to the tenth aspects or a nucleic acid of the eleventh aspect.

The treatment may modulate the immune response in the subject. The immune response may be modulated via modulation of Toll-like receptor signalling.

According to a seventeenth aspect of the present invention there is provided a method for treating or preventing a disease or condition in a subject, the method comprising administering to the subject an effective amount of a Cpn10 polypeptide of any one of the first to the tenth aspects or a nucleic acid of the eleventh aspect.

The disease, disorder or condition may be selected from acute or chronic inflammatory diseases, asthma, allergy, multiple sclerosis, GVHD, or an infectious disease. The infectious disease may result from a bacterial or viral infection. The bacteria may be a Gram negative bacteria.

According to a eighteenth aspect of the present invention there is provided a method for modulating TLR4 signalling in a subject, or in at least one cell, tissue or organ thereof, the method comprising administering an effective amount of a Cpn10 polypeptide of any one of the first to the tenth aspects or a nucleic acid of the eleventh aspect.

Typically the Cpn10 regulates agonist-induced TLR4 signalling.

According to a nineteenth aspect of the present invention there is provided a method for modulating the production and/or secretion of one or more immunomodulators in a subject, or at least one cell, tissue or organ thereof, the method comprising administering an effective amount of a Cpn10 polypeptide of any one of the first to the tenth aspects or a nucleic acid of the eleventh aspect.

The Cpn10 may modulate signalling from TLR4.

The immunomodulator may be a pro-inflammatory cytokine or chemokine or an anti-inflammatory cytokine or chemokine. The cytokine or chemokine may be selected from TNF-α, IL-6, RANTES, IL-10, TGF-β or a type I interferon. The type I interferon may be IFNα or IFNβ.

According to a twentieth aspect of the present invention there is provided a method of identifying a compound that binds to a polypeptide of any one of the first to the tenth aspects, the method comprising the steps of:

(a) contacting a candidate compound with said polypeptide; and (b) assaying for the formation of a complex between the candidate compound and said polypeptide.

The assay for the formation of a complex may be a competitive binding assay or a two-hybrid assay.

According to a twenty-first aspect of the present invention there is provided a method of screening for a compound that modulates the activity of a polypeptide of any one of the first to the tenth aspect, the method comprising the steps of:

(a) contacting said polypeptide with a candidate compound under conditions suitable to enable interaction of said candidate compound to said polypeptide; and (b) assaying for activity of said polypeptide.

Assaying for activity of the polypeptide may comprise adding a labelled substrate and measuring a change in the labelled substrate.

The invention also contemplates variants, derivatives, homologues, analogues and fragments of the modified Cpn10 polypeptides and polynucleotides according to the above aspects and embodiments.

According to the above aspects and embodiments the Cpn10 polypeptides and polynucleotides may be derived from any animal, may be generated using recombinant DNA technologies or may be synthetically produced. Typically the Cpn10 is a eukaryotic Cpn10.

According to the above aspects the wild type Cpn10 polypeptide may be a human Cpn10 polypeptide comprising the amino acid sequence as set forth in SEQ ID NO:1 or 21.

According to the above aspects the wild type Cpn10 polypeptide may be encoded by the nucleotide sequence as set forth in SEQ ID NO:2 or 22.

According to the above aspects and embodiments the immunomodulatory activity of a Cpn10 polypeptide may involve generation of heptamers of the polypeptide.

DEFINITIONS

In the context of this specification, the term "comprising" means "including principally, but not necessarily solely". Furthermore, variations of the word "comprising", such as "comprise" and "comprises", have correspondingly varied meanings.

The term "wild-type" as used herein in relation to Cpn10 polypeptides includes polypeptides in their native or non-native form. For example, native human Cpn10 is acetylated at its N-terminus; the present invention contemplates, within the scope of the term wild-type, polypeptides acetylated or non-acetylated. Further, wild type Cpn10 polypeptides may comprise an additional alanine (A) reside at the N-terminus (WO 2004/041300, the disclosure of which is incorporated herein by reference).

The term "polypeptide" means a polymer made up of amino acids linked together by peptide bonds. The terms "polypeptide" and "protein" are used interchangeably herein, although for the purposes of the present invention a "polypeptide" may constitute a portion of a full length protein.

The term "polynucleotide" as used herein refers to a single- or double-stranded polymer of deoxyribonucleotide, ribonucleotide bases or known analogues of natural nucleotides, or mixtures thereof. The term includes reference to the specified sequence as well as to the sequence complimentary thereto, unless otherwise indicated. The terms "polynucleotide" and "nucleic acid" are used interchangeably herein.

The term "isolated" means that the molecule in question has been removed from its natural environment or host, and associated impurities reduced or eliminated such that the molecule in question is the predominant species present (i.e., on a molar basis it is more abundant than any other individual species in the composition/sample). Typically a substantially purified fraction is a composition wherein the object species comprises at least about 30 percent (on a molar basis) of all macromolecular species present.

Generally, a substantially pure composition will comprise more than about 80 to 90 percent of all macromolecular species present in the composition. Most typically, the object species is purified to essential homogeneity (contaminant species cannot be detected in the composition by conventional detection methods) wherein the composition consists essentially of a single macromolecular species.

As used herein the term "substantially" means the majority but not necessarily all, and thus in relation to a modified polypeptide "substantially" lacking a component region of a corresponding wild-type polypeptide, the modified polypeptide may retain a portion of that component region. For example, a modified polypeptide "substantially" lacking a component region of a corresponding wild-type polypeptide may retain approximately 50 percent or less of the sequence of the component region, although typically the component region is rendered structurally and/or functionally inactive by virtue of the proportion of the sequences of the region omitted.

The term "conservative amino acid substitution" as used herein refers to a substitution or replacement of one amino acid for another amino acid with similar properties within a polypeptide chain (primary sequence of a protein). For example, the substitution of the charged amino acid glutamic acid (Glu) for the similarly charged amino acid aspartic acid (Asp) would be a conservative amino acid substitution.

As used herein the terms "treatment", "treating" and variations thereof, refer to any and all uses which remedy a disease state or symptoms, prevent the establishment of disease, or otherwise prevent, hinder, retard, or reverse the progression of disease or other undesirable symptoms in any way whatsoever.

As used herein the term "effective amount" includes within its meaning a non-toxic but sufficient amount of an agent or compound to provide the desired therapeutic or prophylactic effect. The exact amount required will vary from subject to subject depending on factors such as the species being treated, the age and general condition of the subject, the severity of the condition being treated, the particular agent being administered and the mode of administration and so forth. Thus, it is not possible to specify an exact "effective amount". However, for any given case, an appropriate "effective amount" may be determined by one of ordinary skill in the art using only routine experimentation.

As used herein the terms "modulating", "modulates" and variations thereof refer to increasing or decreasing the level of activity, production, secretion or functioning of a molecule in the presence of a particular molecule or agent of the invention compared to the level of activity, production, secretion or other functioning thereof in the absence of the molecule or agent. These terms do not imply quantification of the increase or decrease. The modulation may be of any magnitude sufficient to produce the desired result and may be direct or indirect.

BRIEF DESCRIPTION OF THE DRAWINGS

FIG. 1. A. Crystal structure of *E. coli* Cpn10 (GroES) showing the anti-parallel-barrel, the "roof" β-hairpin loop and mobile loop regions. Cpn10 is comprised of seven identical 10 kDa subunits. B. Amino acid sequence of wild-type human Cpn10 monomer. Predicted 18 amino acid mobile loop in bold, italic. Predicted 14 amino acid roof β-hairpin in bold, underline.

FIG. 15. Cpn10 activity in a murine inflammatory model of endotoxaemia. Cpn10 and Cpn10 variants reduced LPS-induced serum TNF-α, IL-10 and IL-6 production. Sera from "LPS challenged" (see Table 1, groups 1, 3, 5, 7, 9 and 11) or "saline control" (see Table 1, groups 2, 4, 6, 8, 10 and 12) mice were analyzed for inflammatory-associated cytokines using CBA (see Methods). The levels of A, B) TNF-α, C, D) IL-6, and E, F) IL-10 cytokines were plotted with the mean of each group displayed (horizontal bar). 1-way ANOVA analysis with Tukey's post-hoc test was performed for each data set. Statistical significance in the data is indicated in brackets ($p<0.05$) (see text for details).

SEQUENCE REFERENCES

Figure 2A:
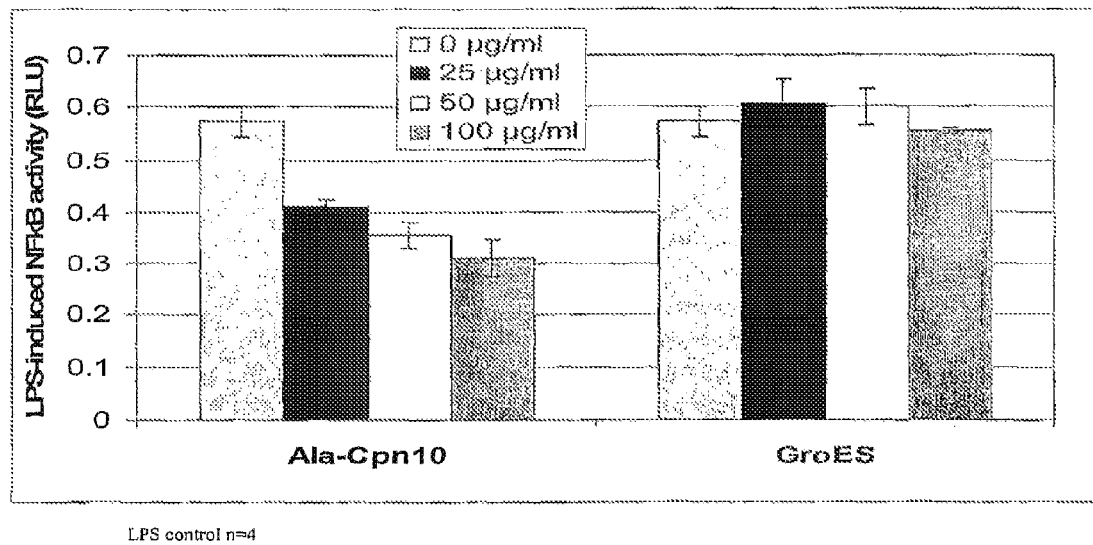
FIG. 2. Effect of Human Ala-Cpn10 and *E. coli* GroES on TLR4 signaling. Dose-responsive inhibition of LPS-induced HIV-LTR activation (an indirect measure of NFκB activity) by human Ala-Cpn10 (batch CH001) but not *E. coli* GroES. Panel B show the results from panel A as percent inhibition of luciferase activity (NFκB activity) relative to the levels of luciferase produced with LPS alone. The LPS alone samples are the mean of 4 replicates, all other samples are the mean of 2 replicates. RLU=relative light units. NFκB activity was induced with 5 ng/ml Lipopolysaccharide (LPS).

The reference table below provides nomenclature of Cpn10 polypeptides used throughout this specification. This table contains descriptions of features of Cpn10 polypeptides disclosed herein and their corresponding amino acid and nucleic acid sequence ID numbers.

TABLE 1

| Cpn10 name | Feature | Additional Feature | Amino Acid SEQ ID NO. | Nucleic Acid SEQ ID NO. |
|---|---|---|---|---|
| X-Cpn10 (i.e. non-acetylated) | Does not include an acetyl group at the N terminus | Does not include initiating Methionine | 23 | 44 |
| Cpn10 (Wild type) | Does not include an acetyl group | Includes initiating Methionine | 1 | 2 |
| Cpn10-Δml (Cpn10-delta mobile loop) | Mobile loop deleted | Includes initiating Methionine | 3 | 4, 5 |
| Cpn10-Δroof (Cpn10-delta-roof) | Roof loop deleted | Includes initiating Methionine | 6 | 7, 8 |
| Cpn10-β-barrel (Cpn10-beta-barrel) | Roof loop and mobile loop deleted | Includes initiating Methionine | 9 | 10 |
| E. Coli Cpn10 (GroES) | Bacterial homolog of Cpn10 | Includes initiating Methionine | 11 | 34 |
| Mobile loop only | Example of a mobile loop sequence in human Cpn10 | | 12 | |
| Beta hairpin roof ("roof") loop only | Example of a roof loop sequence in human Cpn10 | | 13 | |
| Cpn10-NtermES | Human Cpn10 except for E. Coli N terminus | Includes initiating Methionine | 14 | 43 |
| Forward primer for EEE tripeptide | EEE tripeptide is located in the mobile loop | | 15 | |

TABLE 1-continued

| Cpn10 name | Feature | Additional Feature | Amino Acid SEQ ID NO. | Nucleic Acid SEQ ID NO. |
|---|---|---|---|---|
| Reverse primer for EEE tripeptide | EEE tripeptide is located in the mobile loop | | 16 | |
| Forward primer for generating IFI tripeptide | IFI tripeptide is located in the mobile loop | | 17 | |
| Reverse primer for generating IFI tripeptide | IFI tripeptide is located in the mobile loop | | 18 | |
| Forward primer for generating III tripeptide | III tripeptide is located in the mobile loop | | 19 | |
| Reverse primer for III tripeptide | III tripeptide is located in the mobile loop | | 20 | |
| Ala-Cpn10 (Wild type Cpn10) | Extra N terminal alanine residue | Does not include initiating Methionine | 21 | 22 |
| Ala-Cpn10-Δml (Ala-Cpn10-delta mobile loop) | Mobile loop deleted | Does not include initiating Methionine but includes extra N terminal alanine | 24 | 25 |
| Ala-Cpn10-Δroof (Ala-Cpn10-delta-roof) | Roof loop deleted | Does not include initiating Methionine but includes extra N terminal alanine | 26 | 27 |
| Ala-Cpn10-β-barrel (Ala-Cpn10-beta-barrel) | Roof loop and mobile loop deleted | Does not include initiating Methionine but includes extra N terminal alanine residue | 28 | 29 |
| Gly-Cpn10 | Glycine replaces the extra N terminal alanine residue | | 30 | 31 |
| Ala-Cpn10-IFI | IFI tripeptide replaces IML tripeptide in mobile loop | Extra N terminal alanine residue | 35 | 36 |
| Ala-Cpn10-III | III tripeptide replaces IML tripeptide in mobile loop | Extra N terminal alanine residue | 37 | 38 |
| Ala-Cpn10-EEE-cHis | EEE tripeptide replaces IML tripeptide in mobile loop | Extra N terminal alanine residue and a His tag at the C terminus | 39 | 40 |
| Ala-Cpn10-cHis | Extra N terminal alanine residue | His tag at the C terminus | 41 | 42 |

BEST MODE OF PERFORMING THE INVENTION

Cpn10 is a dome-shaped, heptameric ring of identical 10 kDa subunits (see FIG. 1). The inner surface of the dome is hydrophilic and highly charged. Each Cpn10 subunit forms an irregular β-barrel topology from which two large extensions protrude. The first extension is a β-hairpin loop that extends towards the centre of the heptamer and forms the dome-like structure. Intriguingly, whereas the roof of GroES (*E-coli* Cpn10) is charged negatively under physiological conditions, the roof of mammalian Cpn10 is positively charged; while a large portion of the roof is missing completely from the bacteriophage Cpn10 (Gp31). The molecule also has another extension that is a flexible 18 amino acid mobile loop that extends from the base of the dome and mediates an interaction with Cpn60. Site-directed mutagenesis has identified several residues within the mobile loop which are crucial for the interaction with Cpn60, namely three hydrophobic residues (30-IML-32) at the base of the mobile loop which constitute the actual Cpn60-binding site and two residues (26-T and 33-P) which restrict the flexibility of the mobile loop (Richardson et al., 2001, *J Biol Chem* 276:4981-4987). Therefore, the association of Cpn10 with Cpn60 is mediated by the 18 amino acid mobile loop of Cpn10 (for amino acid sequence see FIG. 1B). In *E. coli* GroES the Cpn60/GroEL-binding site tripeptide is less hydrophobic (25-IVL-27) and the mobile loop is more flexible than mammalian Cpn10. These changes decrease the affinity of GroES for Cpn60/GroEL and as a result, GroES can not form a productive interaction with Cpn60 while both Cpn10 and GroES function with GroEL.

Beginning with the hypothesis that the mechanism by which extracellular Cpn10 produces its immunomodulatory effects involves Cpn60 (Johnson et al., 2005, *J Biol Chem* 280:4037-4047), the present inventors generated site-specific mutants of Cpn10 targeting the mobile loop region and demonstrate herein that mutations which perturb interactions with Cpn60 retain immunomodulatory activity.

Accordingly, in one aspect the present invention provides isolated Cpn10 polypeptides displaying immunomodulatory activity but substantially lacking protein folding ability.

It is also demonstrated herein that deletion of a substantial portion of the mobile loop region and/or the roof β-hairpin region of Cpn10 does not abolish the ability of Cpn10 to modulate signalling from the Toll-like receptor TLR4.

Accordingly, the present invention also provides isolated Cpn10 polypeptides having immunomodulatory activity, the polypeptides comprising one or more amino acid substitutions, deletions and/or additions in one or both of the mobile loop region and the roof β-hairpin region compared to a corresponding wild-type Cpn10 polypeptide. The deletion of the mobile loop and the roof loop of Cpn10 is termed the Ala-Cpn10-β-barrel polypeptide as disclosed herein.

The present invention also provides isolated Cpn10 polypeptides substantially lacking one or both of the mobile loop region and the roof β-hairpin region of the corresponding wild-type Cpn10 polypeptide.

As described herein the present inventors have also demonstrated that E. coli GroES is not capable of inducing the immunomodulatory effect attributable to human Cpn10, as determined by modulation of TLR signalling. Further, the inactivity of a Cpn10 polypeptide in which the N-terminal residues of human Cpn10 have been replaced by the corresponding N-terminal residues from E. coli GroES demonstrates that the N-terminus of Cpn10 is required for immunomodulatory activity.

As further described herein the present inventors have also demonstrated that the addition of a glycine residue to the N terminus of Cpn10 augments immunomodulatory activity. It is contemplated that the presence of an acetyl group or an amino acid which shares structural homology to an acetyl group such as an alanine residue or a glycine residue augments immunomodulatory activity of Cpn10.

Polypeptides

As disclosed herein the present invention contemplates Cpn10 polypeptides, typically possessing immunodulatory activity, comprising one or more amino acid deletions, additions or substitutions in comparison with a corresponding wild-type Cpn10 polypeptide. Typically the wild-type Cpn10 is any Cpn10 polypeptide from a eukaryotic organism. By way of example, the Cpn10 may be derived from yeast (e.g. Saccharomyces cerevisiae), nematode (e.g. Caenorhabditis elegans), frog (e.g. Xenopus tropicalis), chicken (e.g. Gallus gallus), zebrafish (e.g. Danio rerio), fly (e.g. fruit fly such as Drosophila melanogaster), plant (e.g. Arabidopsis thaliana) or a mammal. The mammalian Cpn10 may be primate, murine, ovine, bovine, canine, feline, porcine or equine. Alternatively the Cpn10 may be archaeal in origin. In particular embodiments the Cpn10 is human Cpn10. The amino acid sequence of the wild-type human Cpn10 may be as set forth in SEQ ID NO:1 or 21. The nucleotide sequence encoding the wild-type Cpn10 may be as set forth in SEQ ID NO:2 or 22 or display sufficient sequence identity thereto to hybridize to the sequence of SEQ ID NO:2 or 22.

The present invention relates to modifications of wild-type Cpn10 polypeptides as disclosed herein and encompasses otherwise wild-type molecules modified at the N-terminus or C-terminus by the addition, deletion, or substitution of one or more amino acid residues. For example, amino acid additions may result from the fusion of a Cpn10 polypeptide or fragment thereof with a second polypeptide or peptide, such as a polyhistidine tag, maltose binding protein fusion, glutathione —S-transferase fusion, green fluorescent protein fusion, or the addition of an epitope tag such as FLAG or c-myc. For example, a modification of a wild-type human Cpn10 polypeptide may comprise an additional glycine (G) residue. The Cpn10 polypeptide may or may not include the initiating methionine at the N terminus.

In the case of immunomodulatory Cpn10 polypeptides of the invention based on, or substantially derived from human Cpn10, such polypeptides typically comprise the N-terminal sequence MAGQAFRKFL (SEQ ID NO: 32), optionally including one or more modifications as described above.

As disclosed herein, Cpn10 polypeptides of the invention may comprise one or more amino acid additions, deletions or substitutions in either or both of the mobile loop region and the roof β-hairpin region. In one embodiment, one or more amino acid substitutions may be made in the mobile loop region, for example within the tripeptide sequence responsible for interaction with Cpn60, such that the modified polypeptide retains immunomodulatory activity but does not retain protein folding activity. In an alternative embodiment the Cpn10 polypeptide substantially lacks the mobile loop region, for example as exemplified by the sequence set forth in SEQ ID NO:3 or 24, or the roof β-hairpin region, for example as exemplified by the sequence set forth in SEQ ID NO:6 or 26, or both the mobile loop and roof β-hairpin regions, for example as exemplified by the sequence set forth in SEQ ID NO:9 or 28.

As defined herein, the amino acids constituting the mobile loop or roof β-hairpin are defined on the basis of the sequence and known crystal structure of the E. coli Cpn10, GroES. The locations of the mobile loop and roof β-hairpin regions in eukaryotic Cpn10 polypeptides are predicted to be similar in view of the conservation of Cpn10 sequences through evolution and the conservation of predicted three-dimensional protein structures. However the precise boundaries of the mobile loop and roof β-hairpin regions in eukaryotic Cpn10 polypeptides may differ slightly from those of GroES.

The term "variant" as used herein refers to substantially similar sequences. Generally, polypeptide sequence variants possess qualitative biological activity in common. Further, these polypeptide sequence variants may share at least 50%, 55%, 60%, 65%, 70%, 75%, 80%, 85%, 90%, 95%, 96%, 97%, 98% or 99% sequence identity. Also included within the meaning of the term "variant" are homologues of polypeptides of the invention. A homologue is typically a polypeptide from a different species but sharing substantially the same biological function or activity as the corresponding polypeptide disclosed herein.

Further, the term "variant" also includes analogues of the polypeptides of the invention, wherein the term "analogue" means a polypeptide which is a derivative of a polypeptide of the invention, which derivative comprises addition, deletion, substitution of one or more amino acids, such that the polypeptide retains substantially the same function. The term "conservative amino acid substitution" refers to a substitution or replacement of one amino acid for another amino acid with similar properties within a polypeptide chain (primary sequence of a protein).

The present invention also contemplates fragments of the polypeptides disclosed herein. The term "fragment" refers to a polypeptide molecule that encodes a constituent or is a constituent of a polypeptide of the invention or variant thereof. Typically the fragment possesses qualitative biological activity in common with the polypeptide of which it is a constituent. The peptide fragment may be between about 5 to about 150 amino acids in length, between about 5 to about 100 amino acids in length, between about 5 to about 50 amino acids in length, or between about 5 to about 25 amino acids in length. Alternatively, the peptide fragment may be between about 5 to about 15 amino acids in length.

Cpn10 polypeptides modified at the N- and/or C-terminus by the addition, deletion or substitution of one or more amino acid residues as described above also fall within the scope of the present invention.

Production of Cpn10

In accordance with the present invention Cpn10 polypeptides may be produced using standard techniques of recombinant DNA and molecular biology that are well known to those skilled in the art. Guidance may be obtained, for example, from standard texts such as Sambrook et al., *Molecular Cloning: A Laboratory Manual*, Cold Spring Harbor, N.Y., 1989 and Ausubel et al., *Current Protocols in Molecular Biology*, Greene Publ. Assoc. and Wiley-Intersciences, 1992. Methods described in Morton et al., 2000 (*Immunol Cell Biol* 78:603-607), Ryan et al., 1995 (*J Biol Chem* 270:22037-22043) and Johnson et al., 2005 (*J Biol Chem* 280:4037-4047) are examples of suitable purification methods for Cpn10 polypeptides, although the skilled addressee will appreciate that the present invention is not limited by the method of purification or production used and any other method may be used to produce Cpn10 for use in accordance with the methods and compositions of the present invention. Cpn10 peptides may be produced by digestion of a polypeptide with one or more proteinases such as endoLys-C, endoArg-C, endoGlu-C and *staphylococcus* V8-protease. The digested peptide fragments can be purified by, for example, high performance liquid chromatographic (HPLC) techniques.

The purification of Cpn10 polypeptides of the invention may be scaled-up for large-scale production purposes. For example, as described herein the present inventors have developed a bioprocess for the production of large (gram) quantities of highly pure, clinical grade Cpn10 polypeptides by batch fermentation in *E. coli*.

Cpn10 polypeptides of the present invention, as well as fragments and variants thereof, may also be synthesized by standard methods of liquid or solid phase chemistry well known to those of ordinary skill in the art. For example such molecules may be synthesized following the solid phase chemistry procedures of Steward and Young (Steward, J. M. & Young, J. D., Solid Phase Peptide Synthesis. (2nd Edn.) Pierce Chemical Co., Illinois, USA (1984).

In general, such a synthesis method comprises the sequential addition of one or more amino acids or suitably protected amino acids to a growing peptide chain. Typically, either the amino or carboxyl group of the first amino acid is protected by a suitable protecting group. The protected amino acid is then either attached to an inert solid support or utilized in solution by adding the next amino acid in the sequence having the complementary (amino or carboxyl) group suitably protected and under conditions suitable for forming the amide linkage. The protecting group is then removed from this newly added amino acid residue and the next (protected) amino acid is added, and so forth. After all the desired amino acids have been linked, any remaining protecting groups, and if necessary any solid support, is removed sequentially or concurrently to produce the final polypeptide.

Amino acid changes in Cpn10 polypeptides may be effected by techniques well known to those persons skilled in the relevant art. For example, amino acid changes may be effected by nucleotide replacement techniques which include the addition, deletion or substitution of nucleotides (conservative and/or non-conservative), under the proviso that the proper reading frame is maintained. Exemplary techniques include random mutagenesis, site-directed mutagenesis, oligonucleotide-mediated or polynucleotide-mediated mutagenesis, deletion of selected region(s) through the use of existing or engineered restriction enzyme sites, and the polymerase chain reaction.

The generation of immunomodulatory activity by the Cpn10 polypeptides of the invention may involve the formation of heptamers of the Cpn10 polypeptides. Testing of immunomodulatory activity for the purposes of the present invention may be via any one of a number of techniques known to those of skill in the art. As exemplified herein immunomodulatory activity of Cpn10 polypeptides may be determined by measuring the ability of the polypeptide to modulate signalling from the Toll-like receptor TLR4, for example using a luciferase bioassay, and typically in the presence of a TLR4 agonist such as lipopolysaccharide. Alternatively or in addition, immunomodulatory activity may be determined using other assays in vitro, ex vivo or in vivo, for example via measurement of NF-κB production or the production of cytokines in cells such as peripheral blood mononuclear cells.

Polynucleotides

Embodiments of the present invention provide isolated polynucleotides encoding Cpn10 polypeptides as described above, and variants and fragments of such polynucleotides. The nucleotide sequences encoding wild-type Cpn10 may be as set forth in SEQ ID NO:2 or 22 or display sufficient sequence identity thereto to hybridize to the sequence of SEQ ID NO:2 or 22.

Specifically, the nucleotide sequence encoding the Cpn10-NtermES polypeptide of the invention may be as set forth in SEQ ID NO:43 or display sufficient sequence identity thereto to hybridize to the sequence of SEQ ID NO:43.

The nucleotide sequence encoding the Ala-Cpn10 polypeptide of the invention may be as set forth in SEQ ID NO:22 or display sufficient sequence identity thereto to hybridize to the sequence of SEQ ID NO:22.

The nucleotide sequence encoding the Ala-Cpn10-Δml polypeptide of the invention may be as set forth in SEQ ID NO:25 or display sufficient sequence identity thereto to hybridize to the sequence of SEQ ID NO:25.

The nucleotide sequence encoding the Ala-Cpn10-Δroof polypeptide of the invention may be as set forth in SEQ ID NO:27 or display sufficient sequence identity thereto to hybridize to the sequence of SEQ ID NO:27.

The nucleotide sequence encoding the Cpn10 β-barrel polypeptide of the invention may be as set forth in SEQ ID NO:10 or display sufficient sequence identity thereto to hybridize to the sequence of SEQ ID NO:10. The nucleotide sequence encoding the Ala-Cpn10 β-barrel polypeptide of the invention may be as set forth in SEQ ID NO:29 or display sufficient sequence identity thereto to hybridize to the sequence of SEQ ID NO:29. The nucleotide sequence encoding the Gly-Cpn10 polypeptide of the invention may be as set forth in SEQ ID NO:31 or display sufficient sequence identity thereto to hybridize to the sequence of SEQ ID NO:31.

The nucleotide sequence encoding the Ala-Cpn10-IFI polypeptide of the invention may be as set forth in SEQ ID NO:36 or display sufficient sequence identity thereto to hybridize to the sequence of SEQ ID NO:36.

The nucleotide sequence encoding the Ala-Cpn10-III polypeptide of the invention may be as set forth in SEQ ID NO:38 or display sufficient sequence identity thereto to hybridize to the sequence of SEQ ID NO:38.

The nucleotide sequence encoding the Ala-Cpn10-EEE-cHis polypeptide of the invention may be as set forth in SEQ ID NO:40 or display sufficient sequence identity thereto to hybridize to the sequence of SEQ ID NO:40.

The nucleotide sequence encoding the Ala-Cpn10-cHis polypeptide of the invention may be as set forth in SEQ ID NO:42 or display sufficient sequence identity thereto to hybridize to the sequence of SEQ ID NO:42.

The nucleotide sequence encoding the Cpn10-Δml polypeptide is contemplated within the present invention and may be set forth in SEQ ID NO:4 or 5 or display sufficient sequence identity thereto to hybridize to the sequence of SEQ ID NO:4 or 5.

The nucleotide sequence encoding the Cpn10-Δroof polypeptide is contemplated in the present invention and may be set forth in SEQ ID NO:7 or 8 or display sufficient sequence identity thereto to hybridize to the sequence of SEQ ID NO:7 or 8.

The nucleotide sequence encoding the Cpn10-β-barrel polypeptide is contemplated in the present invention and may be set forth in SEQ ID NO:10 or display sufficient sequence identity thereto to hybridize to the sequence of SEQ ID NO:10.

As for polypeptides discussed above, the term "variant" as used herein refers to substantially similar sequences. Generally, polynucleotide sequence variants encode polypeptides which possess qualitative biological activity in common. Further, these polynucleotide sequence variants may share at least 50%, 55%, 60%, 65%, 70%, 75%, 80%, 85%, 90%, 95%, 96%, 97%, 98% or 99% sequence identity. Also included within the meaning of the term "variant" are homologues of polynucleotides of the invention. A homologue is typically a polynucleotide from a different species but sharing substantially the same activity.

Fragments of polynucleotides of the invention are also contemplated. The term "fragment" refers to a nucleic acid molecule that encodes a constituent or is a constituent of a polynucleotide of the invention. Fragments of a polynucleotide do not necessarily need to encode polypeptides which retain biological activity. Rather the fragment may, for example, be useful as a hybridization probe or PCR primer. The fragment may be derived from a polynucleotide of the invention or alternatively may be synthesized by some other means, for example chemical synthesis. Polynucleotides of the invention and fragments thereof may also be used in the production of antisense molecules using techniques known to those skilled in the art.

Accordingly, the present invention contemplates oligonucleotides and fragments based on the sequences of the polynucleotides of the invention for use as primers and probes. Oligonucleotides are short stretches of nucleotide residues suitable for use in nucleic acid amplification reactions such as PCR, typically being at least about 10 nucleotides to about 50 nucleotides in length, more typically about 15 to about 30 nucleotides in length. Probes are nucleotide sequences of variable length, for example between about 10 nucleotides and several thousand nucleotides, for use in detection of homologous sequences, typically by hybridization. The level of homology (sequence identity) between sequences will largely be determined by the stringency of hybridization conditions. In particular the nucleotide sequence used as a probe may hybridize to a homologue or other variant of a polynucleotide disclosed herein under conditions of low stringency, medium stringency or high stringency. Low stringency hybridization conditions may correspond to hybridization performed at 50° C. in 2×SSC. There are numerous conditions and factors, well known to those skilled in the art, which may be employed to alter the stringency of hybridization. For instance, the length and nature (DNA, RNA, base composition) of the nucleic acid to be hybridized to a specified nucleic acid; concentration of salts and other components, such as the presence or absence of formamide, dextran sulfate, polyethylene glycol, etc.; and altering the temperature of the hybridization and/or washing steps. For example, a hybridization filter may be washed twice for 30 minutes in 2×SSC, 0.5% SDS and at least 55° C. (low stringency), at least 60° C. (medium stringency), at least 65° C. (medium/high stringency), at least 70° C. (high stringency) or at least 75° C. (very high stringency).

In particular embodiments, polynucleotides of the invention may be cloned into a vector. The vector may be a plasmid vector, a viral vector, or any other suitable vehicle adapted for the insertion of foreign sequences, their introduction into eukaryotic cells and the expression of the introduced sequences. Typically the vector is a eukaryotic expression vector and may include expression control and processing sequences such as a promoter, an enhancer, ribosome binding sites, polyadenylation signals and transcription termination sequences.

Antibodies

The present invention provides antibodies that selectively bind to the Cpn10 polypeptides of the present invention, as well as fragments and analogues thereof. Suitable antibodies include, but are not limited to polyclonal, monoclonal, chimeric, humanized, single chain, Fab fragments, and an Fab expression library. Antibodies of the present invention may act as agonists or antagonists of Cpn10 polypeptides, or fragments or analogues thereof.

Preferably antibodies are prepared from discrete regions or fragments of the Cpn10 polypeptides of the invention, in particular those involved in conferring immunomodulatory activity and/or partner or substrate binding. An antigenic Cpn10 polypeptide contains at least about 5, and preferably at least about 10, amino acids.

Methods for the generation of suitable antibodies will be readily appreciated by those skilled in the art. For example, an anti-Cpn10 monoclonal antibody, typically containing Fab portions, may be prepared using the hybridoma technology described in Antibodies-A Laboratory Manual, Harlow and Lane, eds., Cold Spring Harbor Laboratory, N.Y. (1988).

In essence, in the preparation of monoclonal antibodies directed toward Cpn10 polypeptides of the invention, fragments or analogues thereof, any technique that provides for the production of antibody molecules by continuous cell lines in culture may be used. These include the hybridoma technique originally developed by Kohler et al., Nature, 256:495-497 (1975), as well as the trioma technique, the human B-cell hybridoma technique [Kozbor et at, Immunology Today, 4:72 (1983)], and the EBV-hybridoma technique to produce human monoclonal antibodies [Cole et al., in Monoclonal Antibodies and Cancer Therapy, pp. 77-96, Alan R. Liss, Inc., (1985)]. Immortal, antibody-producing cell lines can be created by techniques other than fusion, such as direct transformation of B lymphocytes with oncogenic DNA, or transfection with Epstein-Barr virus. See, e.g., M. Schreier et al., "Hybridoma Techniques" (1980); Hammerling et al., "Monoclonal Antibodies and T-cell Hybridomas" (1981); Kennett et al., "Monoclonal Antibodies" (1980). In summary, a means of producing a hybridoma from which the monoclonal antibody is produced, a myeloma or other self-perpetuating cell line is fused with lymphocytes obtained from the spleen of a mammal hyperimmunized with a recognition factor-binding portion thereof, or recognition factor, or an origin-specific DNA-binding portion thereof. Hybridomas producing a monoclonal antibody useful in practicing this invention are identified by their ability to immunoreact with the present recognition factor and their ability to inhibit specified transcriptional activity in target cells.

A monoclonal antibody useful in practicing the present invention can be produced by initiating a monoclonal hybridoma culture comprising a nutrient medium containing a hybridoma that secretes antibody molecules of the appropriate antigen specificity. The culture is maintained under conditions and for a time period sufficient for the hybridoma to secrete the antibody molecules into the medium. The antibody-containing medium is then collected. The antibody molecules can then be further isolated by well-known techniques. Similarly, there are various procedures known in the art which may be used for the production of polyclonal antibodies to Cpn10 polypeptides of the invention, or fragments or analogues thereof. For the production of Cpn10 polyclonal antibody, various host animals can be immunized by injection with a Cpn10 polypeptide, or a fragment or analogue thereof, including but not limited to rabbits, mice, rats, sheep, goats, etc. Further, the Cpn10 polypeptide or fragment or analogue thereof can be conjugated to an immunogenic carrier, e.g., bovine serum albumin (BSA) or keyhole limpet hemocyanin (KLH). Also, various adjuvants may be used to increase the immunological response, including but not limited to Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *Corynebacterium parvum*.

Screening for the desired antibody can also be accomplished by a variety of techniques known in the art. Assays for immunospecific binding of antibodies may include, but are not limited to, radioimmunoassays, ELISAs (enzyme-linked immunosorbent assay), sandwich immunoassays, immunoradiometric assays, gel diffusion precipitation reactions, immunodiffusion assays, in situ immunoassays, Western blots, precipitation reactions, agglutination assays, complement fixation assays, immunofluorescence assays, protein A assays, and immunoelectrophoresis assays, and the like (see, for example, Ausubel et al., eds, 1994, Current Protocols in Molecular Biology, Vol. 1, John Wiley & Sons, Inc., New York). Antibody binding may be detected by virtue of a detectable label on the primary anti-Cpn10 antibody. Alternatively, the anti-Cpn10 antibody may be detected by virtue of its binding with a secondary antibody or reagent which is appropriately labelled. A variety of methods are known in the art for detecting binding in an immunoassay and are within the scope of the present invention. Antibodies of the present invention can be used in diagnostic methods and kits that are well known to those of ordinary skill in the art to detect qualitatively or quantify Cpn10 in a body fluid or tissue, or alternatively antibodies may be used in methods and compositions for the treatment of various diseases, disorders and conditions.

The antibody (or fragment thereof) raised against a Cpn10 polypeptide of the invention or a fragment or analogue thereof has binding affinity for Cpn10. Preferably, the antibody (or fragment thereof) has binding affinity or avidity greater than about $10^5$ $M^{-1}$, more preferably greater than about $10^6$ $M^{-1}$, more preferably still greater than about $10^7 M^{-1}$ and most preferably greater than about $10^8$ $M^{-1}$.

In terms of obtaining a suitable amount of an antibody according to the present invention, one may manufacture the antibody(s) using batch fermentation with serum free medium. After fermentation the antibody may be purified via a multistep procedure incorporating chromatography and viral inactivation/removal steps. For instance, the antibody may be first separated by Protein A affinity chromatography and then treated with solvent/detergent to inactivate any lipid enveloped viruses. Further purification, typically by anion and cation exchange chromatography may be used to remove residual proteins, solvents/detergents and nucleic acids. The purified antibody may be further purified and formulated into 0.9% saline using gel filtration columns. The formulated bulk preparation may then be sterilized and viral filtered and dispensed.

Agonists and Antagonists

In addition to specific anti-Cpn10 antibodies, the polypeptides of the present invention, and fragments and variants thereof are particularly useful for the screening and identification of compounds and agents that interact with Cpn10. In particular, desirable compounds are those that modulate the immunomodulatory activity of Cpn10. Such compounds may modulate by activating, increasing, inhibiting or preventing Cpn10 immunomodulatory activity. Suitable compounds may exert their effect on Cpn10 by virtue of either a direct (for example binding) or indirect interaction.

Compounds which bind, or otherwise interact with Cpn10 polypeptides of the invention, and specifically compounds which modulate the activity of Cpn10, may be identified by a variety of suitable methods. Interaction and/or binding may be determined using standard competitive binding assays or two-hybrid assay systems.

For example, the two-hybrid assay is a yeast-based genetic assay system (Fields and Song, 1989) typically used for detecting protein-protein interactions. Briefly, this assay takes advantage of the multi-domain nature of transcriptional activators. For example, the DNA-binding domain of a known transcriptional activator may be fused to a Cpn10 polypeptide of the invention, or fragment or variant thereof, and the activation domain of the transcriptional activator fused to a candidate protein. Interaction between the candidate protein and the Cpn10 polypeptide, or fragment or variant thereof, will bring the DNA-binding and activation domains of the transcriptional activator into close proximity. Interaction can thus be detected by virtue of transcription of a specific reporter gene activated by the transcriptional activator.

Alternatively, affinity chromatography may be used to identify binding partners of Cpn10. For example, a Cpn10 polypeptide of the invention, or fragment or variant thereof, may be immobilized on a support (such as sepharose) and cell lysates passed over the column. Proteins binding to the immobilized Cpn10 polypeptide, fragment or variant can then be eluted from the column and identified. Initially such proteins may be identified by N-terminal amino acid sequencing for example.

Alternatively, in a modification of the above technique, a fusion protein may be generated by fusing a Cpn10 polypeptide, fragment or variant to a detectable tag, such as alkaline phosphatase, and using a modified form of immunoprecipitation as described by Flanagan and Leder (1990).

Methods for detecting compounds that modulate Cpn10 activity may involve combining a Cpn10 polypeptide with a candidate compound and a suitable labelled substrate and monitoring the effect of the compound on Cpn10 by changes in the substrate (may be determined as a function of time). Suitable labelled substrates include those labelled for colorimetric, radiometric, fluorimetric or fluorescent resonance energy transfer (FRET) based methods, for example.

Cpn10 polypeptides of the invention and appropriate fragments and variants can be used in high-throughput screens to assay candidate compounds for the ability to bind to, or otherwise interact with Cpn10. These candidate compounds can be further screened against functional Cpn10 to determine the effect of the compound on Cpn10 activity.

It will be appreciated that the above described methods are merely examples of the types of methods which may be employed to identify compounds that are capable of interacting with, or modulating the activity of, the Cpn10 polypeptides, and fragments and variants thereof, of the present invention. Other suitable methods will be known to persons skilled in the art and are within the scope of the present invention.

By the above methods, compounds can be identified which either activate (agonists) or inhibit (antagonists) Cpn10 activity. Such compounds may be, for example, antibodies, low molecular weight peptides, nucleic acids or non-proteinaceous organic molecules.

Potential modulators of Cpn10 activity, for screening by the above methods, may be generated by a number of techniques known to those skilled in the art. For example, various forms of combinatorial chemistry may be used to generate putative non-peptide modulators. Additionally, techniques such as nuclear magnetic resonance (NMR) and X ray crystallography, may be used to model the structure of Cpn10 polypeptides, fragments and variants and computer predictions used to generate possible modulators.

Compositions and Routes of Administration

Cpn10 polypeptides and polynucleotides of the invention may be useful as therapeutic agents. These molecules find use, for example, in treating or preventing a disease or condition in a subject, by administering a therapeutically effective amount of such a molecule to the subject. Typically such diseases and conditions are amenable to treatment by modulation of the immune response in the subject. By way of example, such diseases and conditions may include acute or chronic inflammatory diseases, asthma, allergy, multiple sclerosis, GVHD, and infectious diseases. The infectious disease may result from a bacterial or viral infection. Accordingly, pharmaceutically useful compositions comprising Cpn10 polypeptides and polynucleotides for use in treating or preventing diseases and conditions are contemplated.

Agonists and antagonists of Cpn10 polypeptides of the invention, including anti-Cpn10 antibodies, may also be useful as therapeutic agents. Accordingly, the present invention also contemplates methods of treatment using such agonists and antagonists and pharmaceutical compositions comprising the same.

In general, suitable compositions for use in accordance with the methods of the present invention may be prepared according to methods and procedures that are known to those of ordinary skill in the art and accordingly may include a pharmaceutically acceptable carrier, diluent and/or adjuvant.

Compositions may be administered by standard routes. In general, the compositions may be administered by the parenteral (e.g., intravenous, intraspinal, subcutaneous or intramuscular), oral or topical route. Administration may be systemic, regional or local. The particular route of administration to be used in any given circumstance will depend on a number of factors, including the nature of the condition to be treated, the severity and extent of the condition, the required dosage of the particular compound to be delivered and the potential side-effects of the compound.

In general, suitable compositions may be prepared according to methods which are known to those of ordinary skill in the art and may include a pharmaceutically acceptable diluent, adjuvant and/or excipient. The diluents, adjuvants and excipients must be "acceptable" in terms of being compatible with the other ingredients of the composition, and not deleterious to the recipient thereof.

Examples of pharmaceutically acceptable carriers or diluents are demineralized or distilled water; saline solution; vegetable based oils such as peanut oil, safflower oil, olive oil, cottonseed oil, maize oil, sesame oils, arachis oil or coconut oil; silicone oils, including polysiloxanes, such as methyl polysiloxane, phenyl polysiloxane and methylphenyl polysolpoxane; volatile silicones; mineral oils such as liquid paraffin, soft paraffin or squalane; cellulose derivatives such as methyl cellulose, ethyl cellulose, carboxymethylcellulose, sodium carboxymethylcellulose or hydroxypropylmethylcellulose; lower alkanols, for example ethanol or iso-propanol; lower aralkanols; lower polyalkylene glycols or lower alkylene glycols, for example polyethylene glycol, polypropylene glycol, ethylene glycol, propylene glycol, 1,3-butylene glycol or glycerin; fatty acid esters such as isopropyl palmitate, isopropyl myristate or ethyl oleate; polyvinylpyrridone; agar; carrageenan; gum tragacanth or gum acacia, and petroleum jelly. Typically, the carrier or carriers will form from 10% to 99.9% by weight of the compositions.

The compositions of the invention may be in a form suitable for administration by injection, in the form of a formulation suitable for oral ingestion (such as capsules, tablets, caplets, elixirs, for example), in the form of an ointment, cream or lotion suitable for topical administration, in a form suitable for delivery as an eye drop, in an aerosol form suitable for administration by inhalation, such as by intranasal inhalation or oral inhalation, in a form suitable for parenteral administration, that is, subcutaneous, intramuscular or intravenous injection.

For administration as an injectable solution or suspension, non-toxic parenterally acceptable diluents or carriers can include Ringer's solution, isotonic saline, phosphate buffered saline, ethanol and 1,2-propylene glycol.

Some examples of suitable carriers, diluents, excipients and adjuvants for oral use include peanut oil, liquid paraffin, sodium carboxymethylcellulose, methylcellulose, sodium alginate, gum acacia, gum tragacanth, dextrose, sucrose, sorbitol, mannitol, gelatin and lecithin. In addition these oral formulations may contain suitable flavoring and coloring agents. When used in capsule form the capsules may be coated with compounds such as glyceryl monostearate or glyceryl distearate which delay disintegration.

Adjuvants typically include emollients, emulsifiers, thickening agents, preservatives, bactericides and buffering agents.

Solid forms for oral administration may contain binders acceptable in human and veterinary pharmaceutical practice, sweeteners, disintegrating agents, diluents, flavorings, coating agents, preservatives, lubricants and/or time delay agents. Suitable binders include gum acacia, gelatine, corn starch, gum tragacanth, sodium alginate, carboxymethylcellulose or polyethylene glycol. Suitable sweeteners include sucrose, lactose, glucose, aspartame or saccharine. Suitable disintegrating agents include corn starch, methylcellulose, polyvinylpyrrolidone, guar gum, xanthan gum, bentonite, alginic acid or agar. Suitable diluents include lactose, sorbitol, mannitol, dextrose, kaolin, cellulose, calcium carbonate, calcium silicate or dicalcium phosphate. Suitable flavoring agents include peppermint oil, oil of wintergreen, cherry, orange or raspberry flavoring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, stearic acid, sodium oleate, sodium chloride or talc. Suitable time delay agents include glyceryl monostearate or glyceryl distearate.

Liquid forms for oral administration may contain, in addition to the above agents, a liquid carrier. Suitable liquid carriers include water, oils such as olive oil, peanut oil, sesame oil, sunflower oil, safflower oil, arachis oil, coconut oil, liquid paraffin, ethylene glycol, propylene glycol, polyethylene glycol, ethanol, propanol, isopropanol, glycerol, fatty alcohols, triglycerides or mixtures thereof.

Suspensions for oral administration may further comprise dispersing agents and/or suspending agents. Suitable suspending agents include sodium carboxymethylcellulose, methylcellulose, hydroxypropylmethyl-cellulose, poly-vinyl-pyrrolidone, sodium alginate or acetyl alcohol. Suitable dispersing agents include lecithin, polyoxyethylene esters of fatty acids such as stearic acid, polyoxyethylene sorbitol mono- or di-oleate, -stearate or -laurate, polyoxyethylene sorbitan mono- or di-oleate, -stearate or -laurate and the like.

The emulsions for oral administration may further comprise one or more emulsifying agents. Suitable emulsifying agents include dispersing agents as exemplified above or natural gums such as guar gum, gum acacia or gum tragacanth.

Methods for preparing parenterally administrable compositions are apparent to those skilled in the art, and are described in more detail in, for example, Remington's Pharmaceutical Science, 15th ed., Mack Publishing Company, Easton, Pa., hereby incorporated by reference herein.

The topical formulations of the present invention, comprise an active ingredient together with one or more acceptable carriers, and optionally any other therapeutic ingredients. Formulations suitable for topical administration include liquid or semi-liquid preparations suitable for penetration through the skin to the site of where treatment is required, such as liniments, lotions, creams, ointments or pastes, and drops suitable for administration to the eye, ear or nose.

Drops according to the present invention may comprise sterile aqueous or oily solutions or suspensions. These may be prepared by dissolving the active ingredient in an aqueous solution of a bactericidal and/or fungicidal agent and/or any other suitable preservative, and optionally including a surface active agent. The resulting solution may then be clarified by filtration, transferred to a suitable container and sterilized. Sterilization may be achieved by: autoclaving or maintaining at 90° C.-100° C. for half an hour, or by filtration, followed by transfer to a container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturizer such as glycerol, or oil such as castor oil or arachis oil.

Lotions according to the present invention include those suitable for application to the skin or eye. An eye lotion may comprise a sterile aqueous solution optionally containing a bactericide and may be prepared by methods similar to those described above in relation to the preparation of drops. Lotions or liniments for application to the skin may also include an agent to hasten drying and to cool the skin, such as an alcohol or acetone, and/or a moisturizer such as glycerol, or oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with a greasy or non-greasy basis. The basis may comprise hydrocarbons such as hard, soft or liquid paraffin, glycerol, beeswax, a metallic soap; a mucilage; an oil of natural origin such as almond, corn, arachis, castor or olive oil; wool fat or its derivatives, or a fatty acid such as stearic or oleic acid together with an alcohol such as propylene glycol or macrogols.

The composition may incorporate any suitable surfactant such as an anionic, cationic or non-ionic surfactant such as sorbitan esters or polyoxyethylene derivatives thereof. Suspending agents such as natural gums, cellulose derivatives or inorganic materials such as silicaceous silicas, and other ingredients such as lanolin, may also be included.

The compositions may also be administered in the form of liposomes. Liposomes are generally derived from phospholipids or other lipid substances, and are formed by mono- or multi-lamellar hydrated liquid crystals that are dispersed in an aqueous medium. Any non-toxic, physiologically acceptable and metabolisable lipid capable of forming liposomes can be used. The compositions in liposome form may contain stabilizers, preservatives, excipients and the like. The preferred lipids are the phospholipids and the phosphatidyl cholines (lecithins), both natural and synthetic. Methods to form liposomes are known in the art, and in relation to this specific reference is made to: Prescott, Ed., Methods in Cell Biology, Volume XIV, Academic Press, New York, N.Y. (1976), p. 33 et seq., the contents of which is incorporated herein by reference.

The compositions may be conjugated to an array of polyethylene glycol (PEG) derivatives. The addition of PEG to proteins (PEGylation) is a well established method for decreasing the plasma clearance rates of proteins, thereby increasing their efficacy (Nucci et al., 1991, *Adv. Drug Del. Rev.* 6:133). Additional benefits of PEGylation may include greater stability of proteins, decreased immunogenicity, enhanced solubility and decreased susceptibility to proteolysis (Sheffield W. 2001, *Curr Drug Targets Cardiovasc Haematol Disord.* 1:1-22). PEG molecules contain the basic repeating structure of —$(OCH_3CH_2)_n$-OH and are classified into groups according to their molecular weight. PEG derivatives are conjugated to proteins to increase their hydrodynamic radius and in general, their increase in half-life is directly related to the size of the PEG chain attached (Sheffield W. 2001, *Curr Drug Targets Cardiovasc Haematol Disord.* 1:1-22).

The compositions may also be administered in the form of microparticles. Biodegradable microparticles formed from polylactide (PLA), polylactide-co-glycolide (PLGA), and epsilon-caprolactone ($\epsilon$-caprolactone) have been extensively used as drug carriers to increase plasma half life and thereby prolong efficacy. (R. Kumar, M., 2000, *J Pharm Pharmaceut Sci.* 3(2) 234-258). Microparticles have been formulated for the delivery of a range of drug candidates including vaccines, antibiotics, and DNA. Moreover, these formulations have been developed for various delivery routes including parenteral subcutaneous injection, intravenous injection and inhalation.

The compositions may incorporate a controlled release matrix that is composed of sucrose acetate isobutyrate (SAIB) and organic solvent or organic solvents mixture. Polymer additives may be added to the vehicle as a release modifier to further increase the viscosity and slow down the release rate. SAIB is a well known food additive. It is a very hydrophobic, fully esterified sucrose derivative, at a nominal ratio of six isobutyrate to two acetate groups. As a mixed ester, SAIB does not crystallize but exists as a clear viscous liquid.

Mixing SAIB with a pharmaceutically accepted organic solvent such as ethanol or benzyl alcohol decreases the viscosity of the mixture sufficiently to allow for injection. An active pharmaceutical ingredient may be added to the SAIB delivery vehicle to form SAIB solution or suspension formulations. When the formulation is injected subcutaneously, the solvent diffuses from the matrix allowing the SAIB-drug or SAIB-drug-polymer mixtures to set up as an in situ forming depot.

For the purposes of the present invention molecules and agents may be administered to subjects as compositions either therapeutically or preventively. In a therapeutic application, compositions are administered to a patient already suffering from a disease, in an amount sufficient to cure or at least partially arrest the disease and its complications. The composition should provide a quantity of the molecule or agent sufficient to effectively treat the patient.

The therapeutically effective dose level for any particular patient will depend upon a variety of factors including: the disorder being treated and the severity of the disorder; activity of the molecule or agent employed; the composition employed; the age, body weight, general health, sex and diet of the patient; the time of administration; the route of administration; the rate of sequestration of the molecule or agent; the duration of the treatment; drugs used in combination or coincidental with the treatment, together with other related factors well known in medicine.

One skilled in the art would be able, by routine experimentation, to determine an effective, non-toxic amount of agent or compound which would be required to treat applicable diseases and conditions.

Generally, an effective dosage is expected to be in the range of about 0.0001 mg to about 1000 mg per kg body weight per 24 hours; typically, about 0.001 mg to about 750 mg per kg body weight per 24 hours; about 0.01 mg to about 500 mg per kg body weight per 24 hours; about 0.1 mg to about 500 mg per kg body weight per 24 hours; about 0.1 mg to about 250 mg per kg body weight per 24 hours; about 1.0 mg to about 250 mg per kg body weight per 24 hours. More typically, an effective dose range is expected to be in the range about 1.0 mg to about 200 mg per kg body weight per 24 hours; about 1.0 mg to about 100 mg per kg body weight per 24 hours; about 1.0 mg to about 50 mg per kg body weight per 24 hours; about 1.0 mg to about 25 mg per kg body weight per 24 hours; about 5.0 mg to about 50 mg per kg body weight per 24 hours; about 5.0 mg to about 20 mg per kg body weight per 24 hours; about 5.0 mg to about 15 mg per kg body weight per 24 hours.

Alternatively, an effective dosage may be up to 500 mg/m$^2$. Generally, an effective dosage is expected to be in the range of about 25 to about 500 mg/m$^2$; preferably about 25 to about 350 mg/m$^2$; more preferably about 25 to about 300 mg/m$^2$; still more preferably about 25 to about 250 mg/m$^2$; even more preferably about 50 to about 250 mg/m$^2$; and still even more preferably about 75 to about 150 mg/m$^2$.

Typically, in therapeutic applications, the treatment would be for the duration of the disease state.

Further, it will be apparent to one of ordinary skill in the art that the optimal quantity and spacing of individual dosages will be determined by the nature and extent of the disease state being treated, the form, route and site of administration, and the nature of the particular individual being treated. Also, such optimum conditions can be determined by conventional techniques.

It will also be apparent to one of ordinary skill in the art that the optimal course of treatment, such as the number of doses of the composition given per day for a defined number of days, can be ascertained by those skilled in the art using conventional course of treatment determination tests.

Embodiments of the invention also contemplate the administration of a polynucleotide encoding Cpn10. In such situations the polynucleotide is typically operably linked to a promoter such that the appropriate polynucleotide sequence is produced following administration of the polynucleotide to a subject. The polynucleotide may be administered to subjects in a vector. The vector may be a plasmid vector, a viral vector, or any suitable vehicle adapted for the insertion of foreign sequences, their introduction into eukaryotic cells and the expression of the introduced sequences. Typically the vector is a eukaryotic expression vector and may include expression control and processing sequences such as a promoter, an enhancer, ribosome binding sites, polyadenylation signals and transcription termination sequences. The nucleic acid construct to be administered may comprise naked DNA or may be in the form of a composition, together with one or more pharmaceutically acceptable carriers.

Those skilled in the art will appreciate that in accordance with the methods of the present invention Cpn10 polypeptides of the invention may be administered alone or in conjunction with one or more additional agents. For example, a Cpn10 polypeptide of the invention may be administered together with one or more agonists capable of stimulating a TLR receptor such as TLR4. Additionally, the present invention contemplates combination therapy using Cpn10 polypeptides of the invention in conjunction with other therapeutic approaches to the treatment of diseases and disorders. For example, Cpn10 polypeptides may be useful in the treatment of viral diseases which are responsive to therapy with Type I interferons such as IFNβ or IFNα, and Cpn10 polypeptides of the invention may be used in conjunction with IFNβ in the treatment of autoimmune diseases such as multiple sclerosis.

For such combination therapies, each component of the combination therapy may be administered at the same time, or sequentially in any order, or at different times, so as to provide the desired effect. Alternatively, the components may be formulated together in a single dosage unit as a combination product. When administered separately, it may be preferred for the components to be administered by the same route of administration, although it is not necessary for this to be so.

The present invention will now be described with reference to specific examples, which should not be construed as in any way limiting the scope of the invention.

EXAMPLES

Example 1

Genetic Parameters Used for the Production of Cpn10 Polypeptides

Table 2 describes the genetic parameters, specifically the expression systems, (i.e. plasmid names, antibiotic selection and host cells) used for the production of the Cpn10 polypeptides listed below.

TABLE 2

Description of genetic parameters for the production of the Cpn10 polypeptides

| Cpn10 polypeptide | Plasmid Name | Production System |
|---|---|---|
| Ala-Cpn10 | Ala-Cpn10_pPL550 | XL1-Blue cells with pPL550 AmpR |
| X-Cpn10 | X-Cpn10_pPL550 | XL1-Blue cells with pPL550 AmpR |
| Ala-Cpn10-Δml | Ala-Cpn10-Δml_pPL550 | XL1-Blue cells with pPL550 AmpR |
| Ala-Cpn10-Δroof | Ala-Cpn10-Δroof_pPL550 | XL1-Blue cells with pPL550 AmpR |
| Ala-Cpn10-β-barrel | Ala-Cpn10-β-barrel_pET23a | BL21(DE3)STAR cells with pET23a AmpR |
| Gly-Cpn10 | Gly-Cpn10_pET30a | BL21(DE3)STAR cells with pET30a KanR |
| GroES | GroES_pET11a | BL21(DE3)STAR cells with pET11a AmpR |
| Ala-Cpn10-IFI | Ala-Cpn10-IFI_pPL550 | XL1-Blue cells with pPL550 AmpR |
| Ala-Cpn10-III | Ala-Cpn10-III_pPL550 | XL1-Blue cells with pPL550 AmpR |
| Ala-Cpn10-EEE-cHis | Ala-Cpn10-EEE-cHis_pET23a | BL21(DE3)STAR cells with pET23a AmpR |
| Ala-Cpn10-cHis | Ala-Cpn10-cHis_pET23a | BL21(DE3)STAR cells with pET23a AmpR |
| Cpn10-NtermES | Cpn10-Nterm ES_pET23a | BL21(DE3)STAR cells with pET23a AmpR |

Example 2

Process for Producing Cpn10 Polypeptides

To further define the production process of Cpn10, Ala-Cpn10 is exemplified below with regard to the production process.

Firstly, a heat-inducible expression plasmid encoding human Cpn10 with an additional N-terminal alanine residue (Ala-Cpn10_pPL550) was obtained from Somodevilla-Torres et al. (2003, *Prot. Exp. Purif.* 32: 276-287). Then, the plasmid vector was transformed into the *E. coli* strain XL1-Blue (Stratagene), and a master cell bank was established from a single selected clone.

Ala-Cpn10 was then produced in *E. coli* essentially as described by Ryan et al. (1995, *J Biol Chem* 270: 22037-22043). In addition, the material that did not bind Macro-Prep High Q (BioRad) was further purified by S-Sepharose and then Gel-Filtration (Superdex 200, Amersham Biosciences). Purified Cpn10 in a 50 mM Tris-HCl (pH 7.6) and 150 mM NaCl buffer, was filtered through an Acrodisc with a 0.2 mm Mustang E membrane according to the manufacturer's instructions (Pall Corporation, Ann Arbor, Mich. Cat No. MSTG5E3) to remove residual endotoxins and was stored at −70° C. The purity of Cpn10 was determined to be >99% by SDS-PAGE. Aliquots were thawed once prior to use.

Most of human Cpn10 polypeptides showed the same molar activity as *E. coli* GroES in GroEL-mediated rhodanese refolding assays (Brinker et al., 2001, Cell, 107 223-233) (data not shown). LPS contamination of Cpn10 was determined by the *Limulus Amebocyte* Lysate assay (Bio-Whittaker, Walkersville, Md.) to be <0.03 EU/mg of purified Cpn10 protein.

The authenticity of Cpn10 polypeptides obtained from the production process as described above was assessed on a batch by batch basis by mass spectrometry. As shown in table 3 below the predicted and calculated masses are in agreement.

TABLE 3

Mass Spectrometry Data and Theoretical pI for Cpn10 polypeptides.

| Cpn10 polypeptides | Predicted mass | Calculated mass (Da) |
|---|---|---|
| Ala-Cpn10 | 10871.5 | 10871.6 |
|  | 10871.5 | 10873.0 |
| X-Cpn10 | 10800.5 | 10799.3 |
| Ala-Cpn10-Δml | 9200.6 | 9200.0 |
| Ala-Cpn10-Δroof | 10201.8 | 10202.0 |
| Ala-Cpn10-β-barrel | 8530.8 | 8531.0 |
| Gly-Cpn10 | 10857.5 | 10857.0 |
| GroES | 10386.9 | 10386.0 |
| Ala-Cpn10-IFI | 10887.5 | 10885.8 |
| Ala-Cpn10-III | 10853.5 | 10851.9 |
| Ala-Cpn10-EEE-cHis | 11966.5 | 11966.0 |
| Ala-Cpn10-cHis | 11936.7 | 11936.0 |
| Cpn10-NtermES | 10295.9 | 10295.0 |

Example 3

RAW264-HIV-LTR-LUC Bioassay to Determine Immunomodulatory Activity Cpn10 Polypeptides Immunomodulatory activity of Cpn10 polypeptides were tested using the RAW264-HIV-LTR luciferase bioassay essentially as described in International Patent Application No. PCT/AU2005/000041. This assay, in the presence of lipopolysaccharide (LPS), measures the ability of Cpn10 or the variant, mutant or derivative thereof to modulate signalling from the Toll-like receptor TLR4.

RAW264-HIV-LTR-LUC cells were cultured in the presence of G418 (200 mg/ml) for 5 days after recovery from liquid nitrogen and grown as suspension cultures in 75 cm$^3$ flasks (Greiner Labortechnik, Frickenhausen, Germany). RAW264-HIV-LTR-LUC cells were disaggregated by repeated pipetting and plated at 2.5×10$^5$ cells/well in 24-well plates and incubated overnight (37° C. and 5% $CO_2$). Crude LPS from *E. coli* (Cat. No. L-6529, Strain 055:B5, Sigma) and ultra-pure LPS from *E. coli* (Cat. No. Uri-pelps, Strain 0111:B4, Invivogen) were dissolved in sterile distilled water and stored at 4° C. in glass vials at 1 mg/ml or 5 mg/ml respectively. Immediately prior to use, the solution was vigorously vortexed before aliquots were taken. Cpn10 was preincubated with cells for 2 h prior to the addition of LPS at the indicated concentrations. Following a further 2 h incubation, the adherent cells were processed for the luciferase assay (Luciferase Assay System, Promega, Madison, Wis.). Luciferase activity was measured using either a Turner Designs Luminometer TD 20/20 (RLU) or a Perkin-Elmer Wallace Victor 2 Multilabel Counter (CPS).

Example 4

Analysis of Co-chaperone Activity for Cpn10 Polypeptides Using an in vitro GroEL-mediated Rhodanese Refolding Assay The ability of Cpn10 polypeptides to act as molecular chaperones and fold proteins in conjunction with GroEL was determined by assaying for rhodanese refolding in vitro utilizing a method adapted from Weber F. and Hayer-Hartl M. K. (Chaperonin Protocols, Ed Schneider C., Humana Press Inc., 2000, p 117-126). Native bovine rhodanese (30 μM, SIGMA) was denatured in 20 mM MOPS-KOH (pH7.5), 100 mM KCl and 20 mM MgCl2 (buffer A) containing 5M Guanidine HCl and 8 mM DTT then subsequently diluted (75-fold) from denaturant into buffer A containing GroEL (400 nM), such that the final concentration of rhodanese was 400 nM. GroEL rapidly and stably binds denatured rhodanese (D-Rho) whereas in buffer alone, D-Rho mis-folds and aggregates (i.e. inefficient spontaneous refolding). The addition of Cpn10 (see below) and ATP (20.6 mM) to preformed, stable complexes of GroEL-bound rhodanese permits efficient refolding to proceed. In the absence of Cpn10, the addition of ATP causes D-Rho to cycle on and off GroEL in a folding incompetent manner leading eventually to misfolding and aggregation (this reaction serves as a suitable assay blank). Each folding reaction has a total volume of 290 1.1, at specific time points (ie 0, 15, 30, 45, 60, 75, 90 mins) 304 aliquots are removed and combined with 704 of rhodanese activity assay mixture (57.1 mM $KH_2PO_4$ (pH7.5), 71.4 mM EDTA, 71.4 mM Na thiosulfate and 71.4 mM KCN) for 6 min. Prior to the initiation of refolding reactions with ATP, a 30 μL aliquot is taken as a T=0 min of refolding time point. EDTA within the rhodanese activity assay mixture chelates $Mg^{2+}$ ions, which prevents GroEL binding ATP, the result is an immediate stopping of the folding reaction. Subsequently, rhodanese activity is stopped after 6 min by the addition of 50 μL of 15% (v/v) formaldehyde (final concentration 5% v/v).

Rhodanese catalyses the formation of thiocyanide (Rhodanid) from thiosulfate and cyanide. Thiocyanide is easily detected colorimetrically (Absorbance 450 nm) by the formation of its red iron complex in the presence of Ferric Nitrate. Rhodanese activity measurements (150 μL) are developed by the addition of 150 μL of Ferric Nitrate reagent (164.5 mM ferric nitrate and 9.2% v/v nitric acid). Rhodanese activity measurements are read at A450 nm in 96 well microplates.

A typical rhodanese folding reactions follow an exponential incline in rhodanese activity (i.e. folded rhodanese) with time to a maximum yield of folded rhodanese. At constant amounts of GroEL (400 nM) and rhodanese (400 nM), a linear relationship is observed (between rhodanese activity and time) with increasing amounts of Cpn10 until an equal molar concentration of Cpn10 (7 mer) to GroEL (14 mer) is reached (ie 400 nM). At concentrations of Cpn10 above 400 nM, the increase in rhodanese activity rapidly reaches a maximum. The assay consists of five standards (in duplicate) and test samples (in duplicate). The concentrations of Cpn10 standards are 0 nM, 140 nM, 250 nM, 280 nM and 350 nM. Rhodanese activity (ie Cpn10 activity) measurements from the 30, 45, 60, 75 and 90 min time points are averaged. The 0nM Cpn10 standard serves as a suitable measurement of the assays' background activity; therefore the absorbance value for the 0 nM Cpn10 standard is subtracted from all other calculated absorbance values (or activity values). Following background correction, the absorbance value for the 280 nM Cpn10 standard is nominated as 100% activity and all other absorbance values are converted to a relative % activity based on the 100% standard. Outlier data points are removed by comparison of duplicate measurements, >30% deviation between duplicates is considered unacceptable. Utilizing the acceptable data, a linear calibration curve is generated with five standard concentrations 0 nM Cpn10 (0% Activity), 140 nM Cpn10 (50% Activity), 250 nM Cpn10 (89.3% Activity), 280 nM Cpn10 (100% Activity) and 350 nM Cpn10 (125% Activity). Rhodanese activity (ie Cpn10 activity) is plotted against Cpn10 concentration. For correction of assay bias, the % activity values from the test samples are recalculated using the equation generated from the linear calibration curve.

Concentrations of chaperonins are calculated using the oligomeric molecular weights (MW) of the proteins while rhodanese is calculated using the monomeric MW; i.e E. coli GroEL 14 mer (SwissProt P06139)=800,766.4 g/mol, Human Cpn10 7 mer SwissProt Q04984)=76,100.5 g/mol and Bovine rhodanese 1 mer (SwisProt P00586)=33,164.6 g/mol.

Table 4 shows the refolding activity of the Cpn10 polypeptides on a batch by batch basis and calculated as a percentage of Ala-Cpn10 activity.

TABLE 4

Refolding Activity of Cpn10 polypeptides

| Cpn10 Polypeptides | Refolding activity (% of Ala-Cpn10) |
|---|---|
| Ala-Cpn10 | 100 |
|  | 100 |
| X-Cpn10 | 105 |
| Ala-Cpn10-Δml | 0 |
| Ala-Cpn10-Δroof | 68 |
| Ala-Cpn10-(β-barrel) | 0 |
| Gly-Cpn10 | 107 |
| GroES | 109 |
| Ala-Cpn10-1FI | 114 |
| Ala-Cpn10-III | 41 |
| Ala-Cpn10-EEE-cHis | 0 |
| Ala-Cpn10-cHis | 40 |
| Cpn10-NtermES | 12 |

Example 5

E. Coli GroES does not Inhibit LPS-mediated HIV-LTR Activation

Figure 2B:
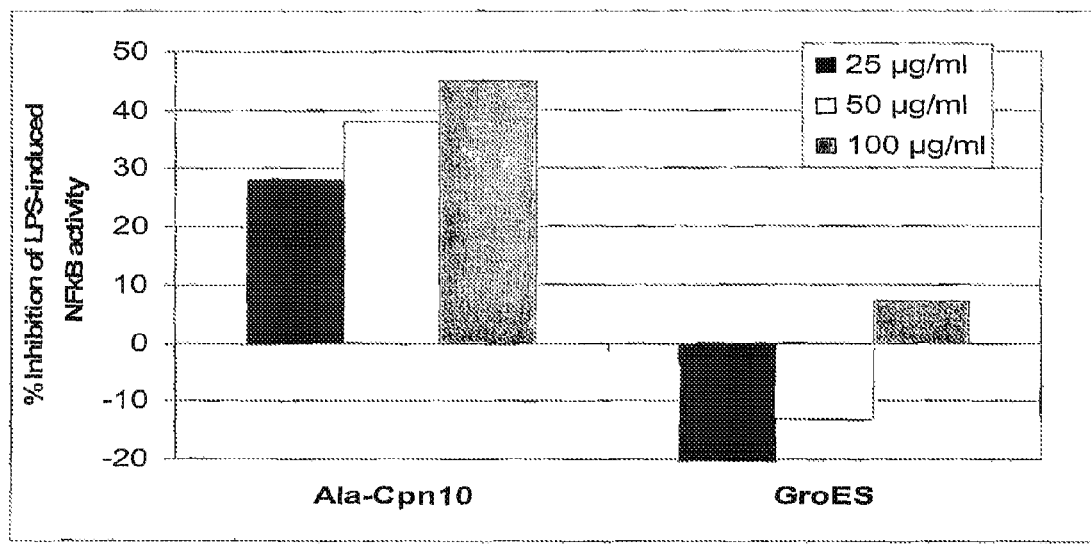
Figure 3:
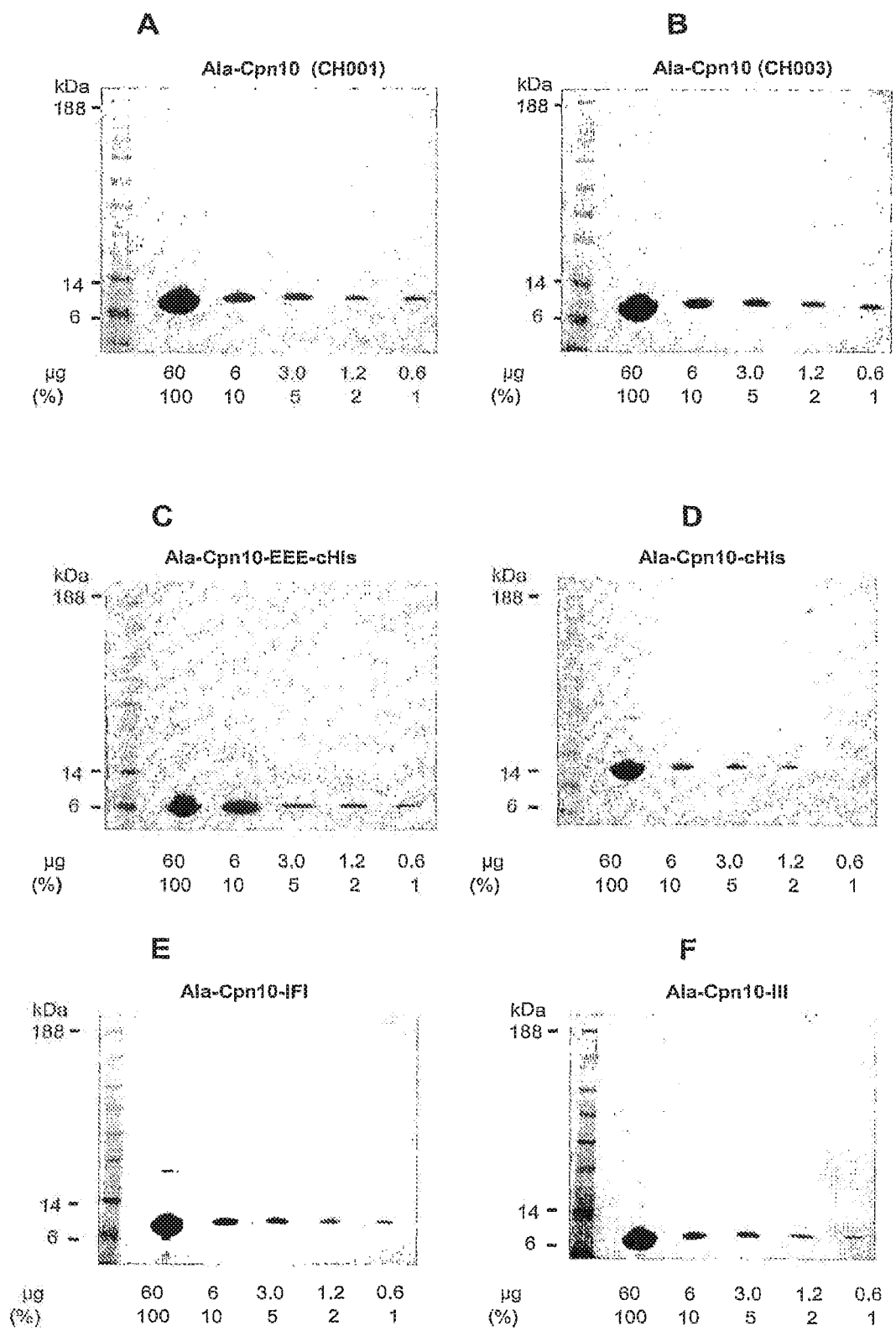
FIG. 3. SDS-PAGE gels. Lane assignments for gels A to 0, except H: Lane 1, molecular weight markers (kDa); lanes 2 to 6, 604, 64, 34, 1.24 and 0.34 of Cpn10 respectively A. 4-12% SDS-PAGE gel stained with Coomassie brilliant blue of purified Ala-Cpn10 (CH001); B. 4-12% SDS-PAGE gel stained with Coomassie brilliant blue of purified Ala-Cpn10 (CH003); C. 4-12% SDS-PAGE gel stained with Coomassie brilliant blue of purified Ala-Cpn10-EEE-cHis; D. 4-12% SDS-PAGE gel stained with Coomassie brilliant blue of purified Ala-Cpn10-cHis; E. 4-12% SDS-PAGE gel stained with Coomassie brilliant blue of purified Ala-Cpn10-IFI; F. 4-12% SDS-PAGE gel stained with Coomassie brilliant blue of purified Ala-Cpn10-III; G. 4-12% SDS-PAGE gel stained with Coomassie brilliant blue of purified Ala-Cpn10-Δml; H. Partial glutaraldehyde cross-linking of Cpn10-Δml (lane 2) shows 7 distinct bands on silver stained 4-12% SDS-PAGE gel, revealing the heptameric structure of the molecule. Lane 1, molecular weight markers (kDa). I. 4-12% SDS-PAGE gel stained with Coomassie brilliant blue of purified Ala-Cpn 10-Δroof. J. 4-12% SDS-PAGE gel stained with Coomassie brilliant blue of purified Ala-Cpn10-β-barrel. K. 4-12% SDS-PAGE gel stained with Coomassie brilliant blue of purified *E. coli* GroES; L. 4-12% SDS-PAGE gel stained with Coomassie brilliant blue of purified Cpn10-NtermES; M. 4-12% SDS-PAGE gel stained with Coomassie brilliant blue of purified *E. coli* GroES; N: 4-12% SDS-PAGE gel stained with Coomassie brilliant blue of purified Gly-Cpn10.

Recombinant E. coli GroES was purified and shown to be essentially free of endotoxin contamination 0.14 EU/mg (see FIG. 3K). Purified GroES was tested in the RAW264.7-HIV-LTR-LUC inhibition assay side by side with Ala-Cpn10 as described above. As shown in FIG. 2, GroES did not inhibit LPS-induced activation of HIV-LTR at any of the tested concentrations (25-100 μg/ml). These results confirm that the immunomodulatory activity observed for Cpn10 is a real and significant biological effect.

Example 6

Construction of Human Cpn10 Mutants

Site-specific Mutants of IML$_{23-25}$

The hydrophobic IML moiety (residues 23-25) of the mobile loop region was mutated to alter the strength of interaction between Cpn10 and Cpn60 (see Table 1). IML was replaced with the charged tripeptide EEE which is predicted to perturb interaction with Cpn60. IML was also mutated to either III or IFI moieties both which are predicted to increase hydrophobicity and thereby potentially strengthen the interaction of Cpn10 with Cpn60. An SDS-PAGE gel showing purification of Ala-Cpn10-EEE-cHis, Ala-Cpn10-IFI, Ala-Cpn10-III and is presented in FIGS. 3C, E and F.

Ala-Cpn10-III, Ala-Cpn10-IFI and Ala-Cpn10-EEE-cHis were generated by Quick Change Site-Directed Mutagenesis (Stratagene) according to the manufacturer's instructions utilizing the complimentary pairs of primers as set forth in table 1. For AlaCpn10-III and Ala-Cpn10-IFI, the Ala-Cpn10_pPL550 plasmid was used as the DNA template. For Ala-Cpn10-EEE-cHis, the Ala-Cpn10-cHis_pET23 plasmid was used as the DNA template (see below).

Ala-Cpn 10

The amino acid sequence predicted to comprise Ala-Cpn10 is set forth in SEQ ID NO:21. A synthetic DNA sequence encoding Ala-Cpn10 (SEQ ID NO:22) was inserted into the pPL550 plasmid at the NcoI and EcoRI sites (Somodevilla-Torres et al., 2003, Prot. Exp. Purif. 32: 276-287). An SDS-PAGE gel showing purification of Ala-Cpn10 in batch CH001 and CH003 is presented in FIGS. 3A and B respectively.

Ala-Cpn 10-cHis

The amino acid sequence predicted to comprise Ala-Cpn10-cHis is set forth in SEQ ID NO:41. A synthetic DNA sequence encoding Ala-Cpn10-cHis (SEQ ID NO:42) was prepared by insertion of the Ala-Cpn10 DNA sequence (SEQ ID NO:22) minus the stop codon into the pET23a plasmid (Novagen) at the NdeI and XhoI sites. The cloning enables a C-terminal hexahistidine tag to be present on Ala-Cpn10. An SDS-PAGE gel showing purification of Ala-Cpn10-cHis is presented in FIG. 3D.

Ala-Cpn10-Δml 16 amino acids were deleted from the mobile loop region (SEQ ID NO:12) of Cpn10 to generate the 86 amino acid variant designated Ala-Cpn10-Δml (SEQ ID NO: 24). A synthetic DNA sequence encoding Ala-Cpn10-Δml (SEQ ID NO: 25) was inserted into the pPL550 plasmid at the NcoI and EcoRI sites (Somodevilla-Torres et al., 2003, Prot. Exp. Purif. 32: 276-287). As the mobile loop is situated in the middle of the Cpn10 polypeptide chain, two residues (one at either end) of the mobile loop were retained to join the N-terminal fragment with the C-terminal fragment and ensure proper folding and assembly of the heptamer.

An SDS-PAGE gel showing purification of Ala-Cpn10-Δml is presented in FIG. 3G. Partial glutaraldehyde cross-linking of Ala-Cpn10-Δml (FIG. 3H, lane 2) shows 7 distinct bands on silver stained 4-12% SDS-PAGE gel, confirming the heptameric structure of the molecule. An amount of 580 pg of Ala-Cpn10-Δml in PBS (pH 7.4) was incubated with 0.01% (w/w) glutaraldehyde (APS) in a total volume of 300 µl at 25° C. for 30 min. Reactions were quenched by the addition of 15 µl of 2M Tris-HCl (pH 8.0). An aliquot of 100 µl of the reaction mixture was resolved on a Superdex 200 HR 10/30 (GE Biosciences) size exclusion column in phosphate buffered saline (PBS) at a flow rate of 0.5 ml min$^{-1}$. The peak eluting at the same retention time as the non-cross-linked Cpn10 oligomer was collected in two 0.5 ml fractions and subsequently analysed by SDS-PAGE and silver staining.

Ala-Cpn10-Δroof 7 amino acids were deleted from the β-hairpin region (SEQ ID NO:13) to generate the 95 amino acid variant designated Ala-Cpn10-Δroof. A synthetic DNA sequence encoding Ala-Cpn10-Δroof (SEQ ID NO:27). was inserted into the pPL550 plasmid at the NcoI and EcoRI sites (Somodevilla-Torres et al., 2003, Prot. Exp. Purif. 32: 276-287). The amino acid sequence of Ala-Cpn10-Δroof is set forth in SEQ ID NO:26. Further, the polynucleotide encoding this polypeptide is set forth in SEQ ID NO:27. An SDS-PAGE gel showing purification of Ala-Cpn10-Δroof is presented in FIG. 3I.

Ala-Cpn10-β-barrel

The amino acid sequence predicted to comprise Ala-Cpn10-β-barrel is set forth in SEQ ID NO:28. An SDS-PAGE gel showing purification of Cpn10-β-barrel is presented in FIG. 3D. A synthetic DNA sequence encoding Ala-Cpn10-β-barrel (SEQ ID NO:29) was inserted into the pPL550 plasmid at the NcoI and EcoRI sites (Somodevilla-Torres et al., 2003, Prot. Exp. Purif. 32: 276-287). An SDS-PAGE gel showing purification of Ala-Cpn10-β-barrel is presented in FIG. 3J.

Gly-Cpn10

The amino acid sequence predicted to comprise Gly-Cpn10 is set forth in SEQ ID NO:30. A synthetic DNA sequence encoding Gly-Cpn10 (SEQ ID NO:31) was inserted into the pET30a plasmid. An SDS-PAGE gel showing purification of Gly-Cpn10 is presented in FIG. 3N.

X-Cpn10

The amino acid sequence predicted to comprise X-Cpn10 is set forth in SEQ ID NO:23. A synthetic DNA sequence encoding X-Cpn10 (SEQ ID NO:44) was inserted into the pPL550 plasmid at the NcoI and EcoRI sites (Somodevilla-Torres et al., 2003, Prot. Exp. Purif. 32: 276-287). An SDS-PAGE gel showing purification of X-Cpn10 is presented in FIG. 3M.

GroES

The amino acid sequence predicted to comprise E. Coli GroES (SwissProt P05380) is set forth in SEQ ID NO:11. A synthetic DNA sequence encoding GroES (SEQ ID NO:34) was inserted into the pET11a plasmid. An SDS-PAGE gel showing purification of GroES is presented in FIG. 3K.

Cpn10-NtermES

The amino acid sequence predicted to comprise Cpn10-NtermES is set forth in SEQ ID NO:14. The Cpn10-NtermES protein was made by replacing residues 1-AGQAFRKFL-9 of human X-Cpn10 (SEQ ID NO:23) with residues 1-MNIR-4 of E. coli GroES (SEQ ID NO:11). A synthetic DNA sequence encoding Cpn10-NtermES (SEQ ID NO:43) was inserted into the pET23a plasmid. An SDS-PAGE gel showing purification of Cpn10-NtermES is presented in FIG. 3L.

Example 7

Activity of IML Tripeptide Mutants of Cpn10

Mutants of the IML tripeptide of the mobile loop (crucial to interaction with Cpn60 and therefore to protein folding) were generated to either perturb or strengthen the interaction of the mobile loop with Cpn60 (see Example 6).

The EEE mobile loop Ala-Cpn10 mutant protein (Ala-Cpn10-EEE-cHis) abolished the ability of Cpn10 to function with GroEL (E. coli Cpn60) during the process of rhodanese refolding in vitro, while the III and IFI mutants remained active (see Table 4).

Figure 4A:
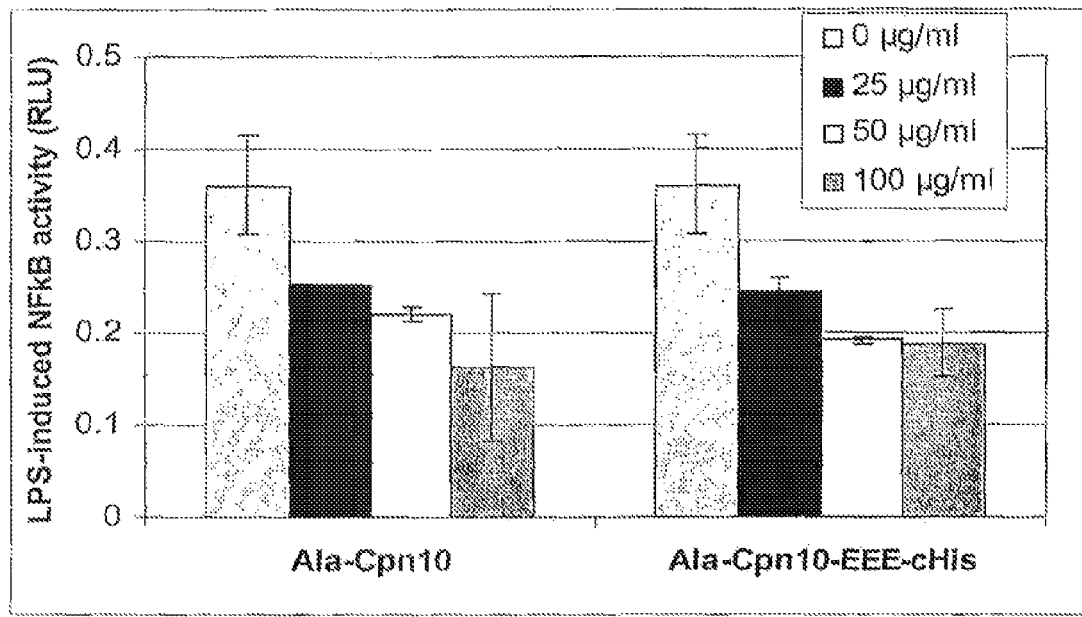
FIG. 4. Effect of Ala-Cpn10, Ala-Cpn10-III, Ala-Cpn10-IFI, Ala-Cpn10-EEE-cHis and Ala-Cpn10-cHis on TLR4 signalling. Dose-responsive inhibition of LPS-induced HIV-LTR activation by human Ala-Cpn10 (batch CH001), Ala-Cpn10 C-terminal hexahistidine tag (Ala-Cpn10-cHis) and numerous mobile loop mutants. Panels B,D,F,H show the results from panels A,C,E,G as percent inhibition of luciferase activity (NFκB activity) relative to the levels of luciferase produced with LPS alone. The LPS alone samples are the mean of 4 replicates, all other samples are the mean of 2 replicates. RLU=relative light units. NFκB activity was induced with 5 ng/ml Lipopolysaccharide (LPS).
Figure 4B:
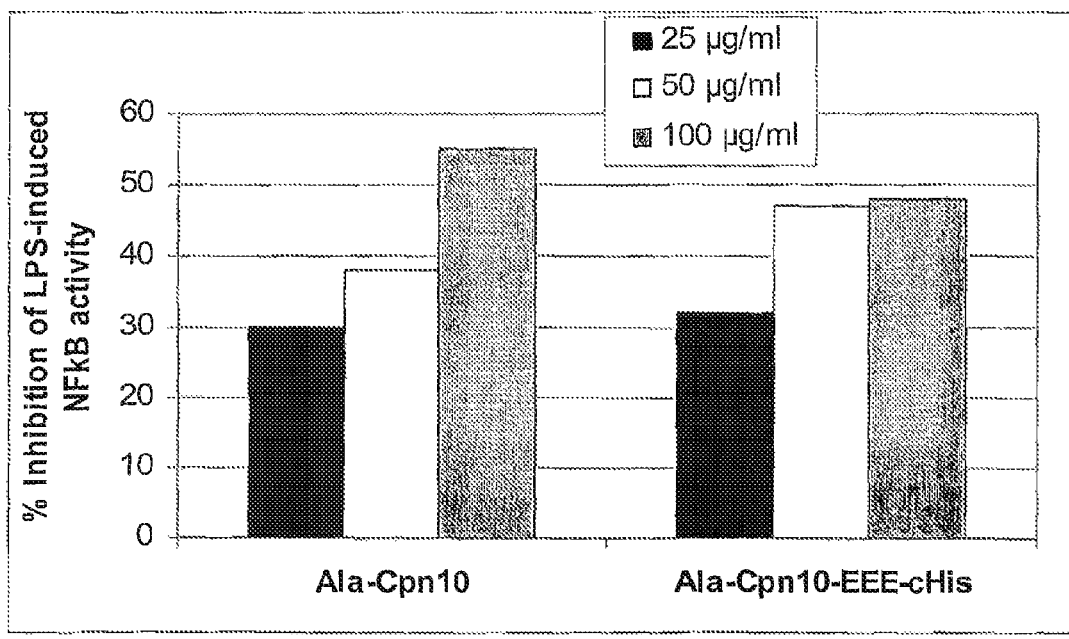
Figure 4C:
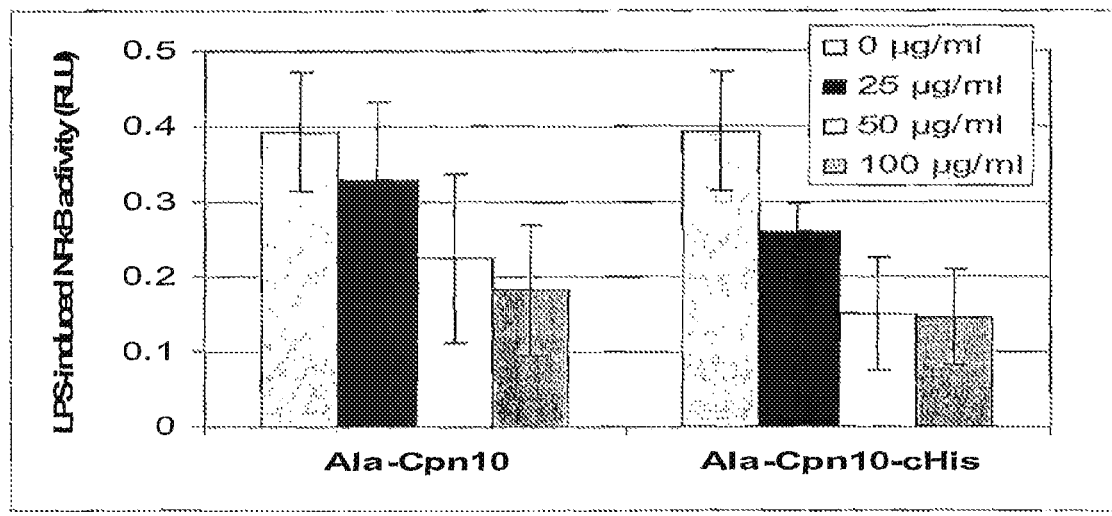
Figure 4D:
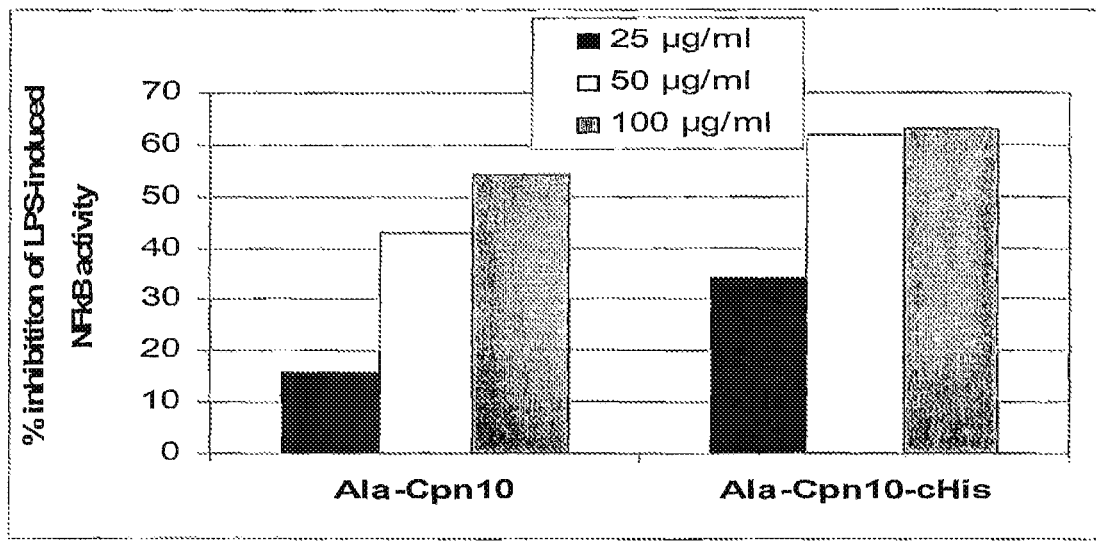
Figure 4E:
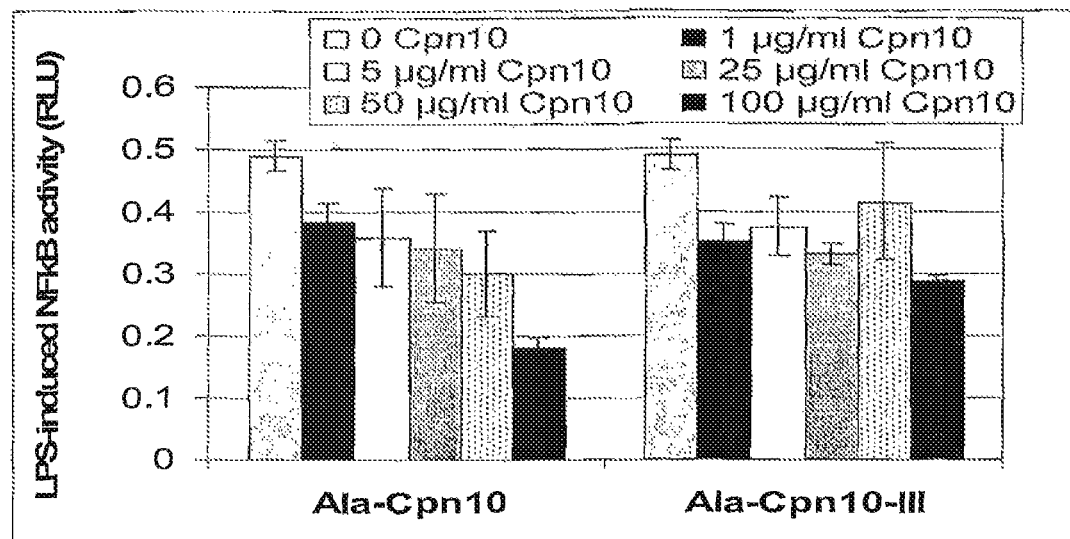
Figure 4F:
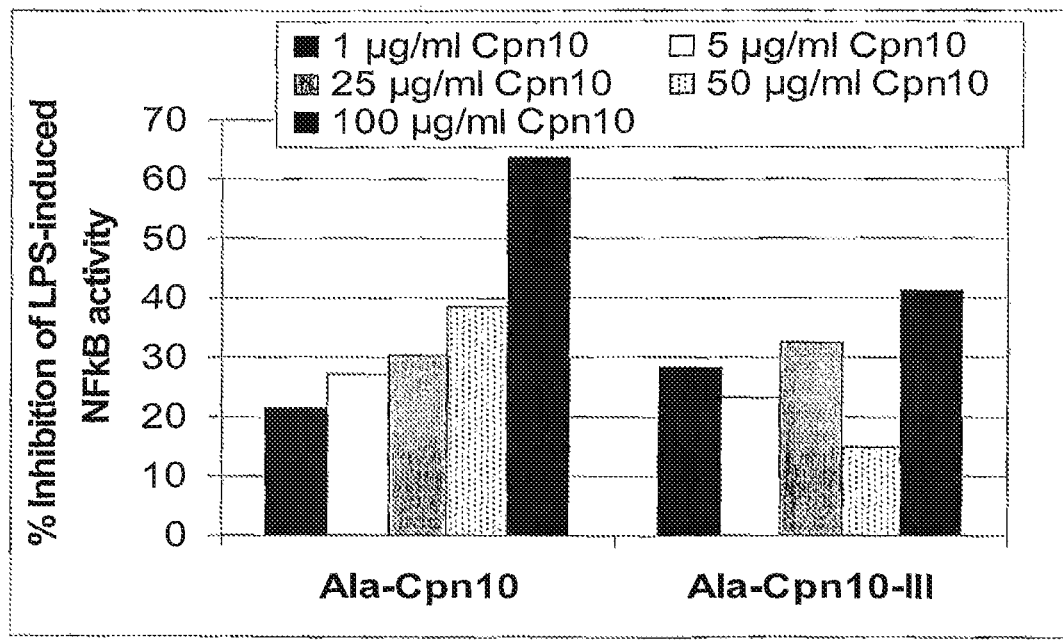
Figure 4G:
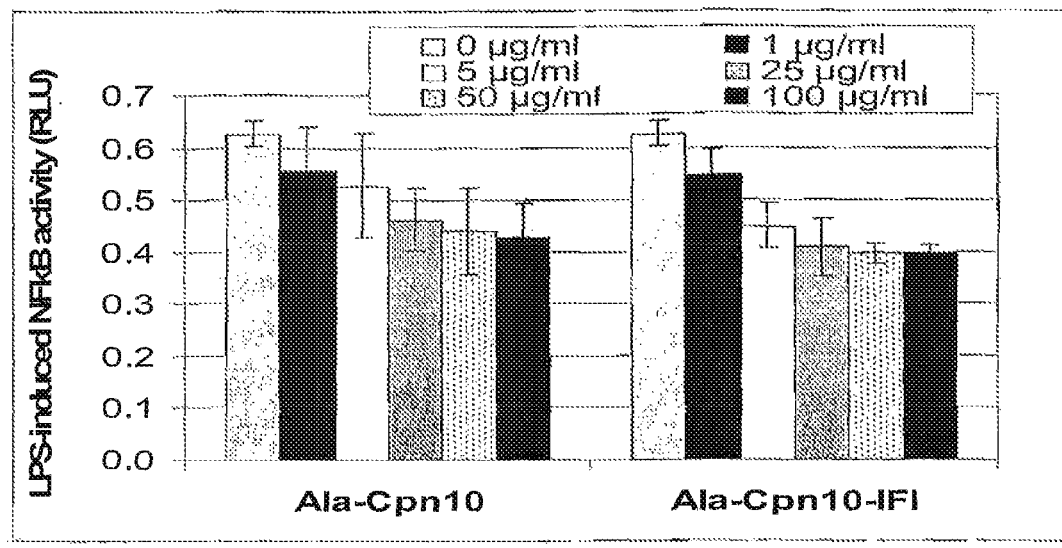
Figure 4H:
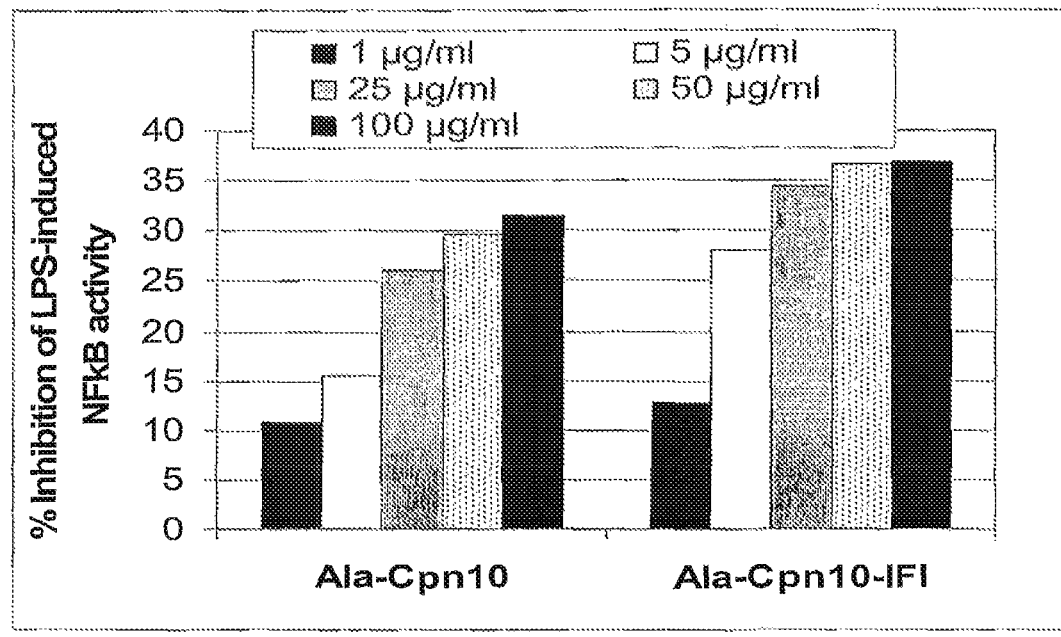

The results indicate that the affinity of Ala-Cpn10-EEE-cHis for GroEL is indeed significantly reduced. In contrast to the protein folding assay, the RAW264.7-HIV-LTR-LUC inhibition assay demonstrated that all tripeptide mutants (including Ala-Cpn10-cHis) are able to modulate TLR4 signalling, with activity similar to the Ala-Cpn10, indicating that the mobile loop (and therefore Cpn60) is not important for this immunomodulatory activity of Cpn10 (see FIGS. 4B, D, F and H).

Example 8

Ala-Cpn10-Δml does not Cooperate with GroEL in Rhodanese Refolding

To confirm that the mobile loop region (and therefore Cpn60) is not required for immunomodulatory activity, 16 amino acids were deleted from the mobile loop region (SEQ ID NO:12) to generate the 86 amino acid variant designated Ala-Cpn10-Δml (see Example 6). The amino acid sequence of Ala-Cpn10-Δml is set forth in SEQ ID NO:24. Ala-Cpn10-Δml was tested for its ability to function productively with GroEL (E. coli Cpn60) in the process of rhodanese refolding. As a positive control, Ala-Cpn10 was included in the same assay and resulted in an activity of ~100% (see table 4). The activity of Ala-Cpn10-Δml was measured as ~0% activity, indicating that it does not interact with GroEL and therefore cannot function as a co-chaperone during the process of protein folding. Both the Ala-Cpn10 and Ala-Cpn10-Δml polypeptides were tested at equal molar concentration.

Example 9

Ala-Cpn10-Δml Inhibits LPS-Induced Activation of HIV LTR

Figure 5A:
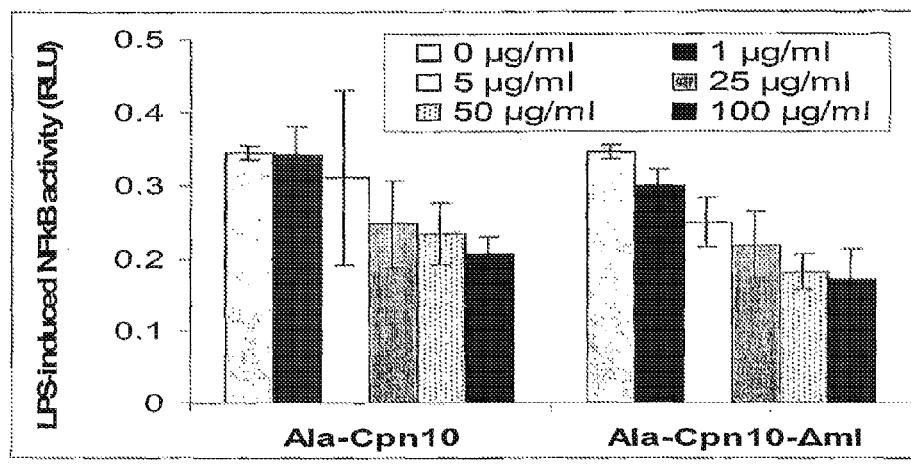
FIG. 5. Effect of Ala-Cpn10 and Ala-Cpn10Δml on TLR4 signalling. Dose-responsive inhibition of LPS-induced HIV-LTR activation by human Ala-Cpn10 (batchCH001) and Ala-Cpn10-Δml. Panel B shows the results from panel A as percent inhibition of luciferase activity (NFκB activity) relative to the levels of luciferase produced with LPS alone. The LPS alone samples are the mean of 4 replicates, all other samples are the mean of 2 replicates. RLU=relative light units. NFκB activity was induced with 5 ng/ml Lipopolysaccharide (LPS).
Figure 5B:
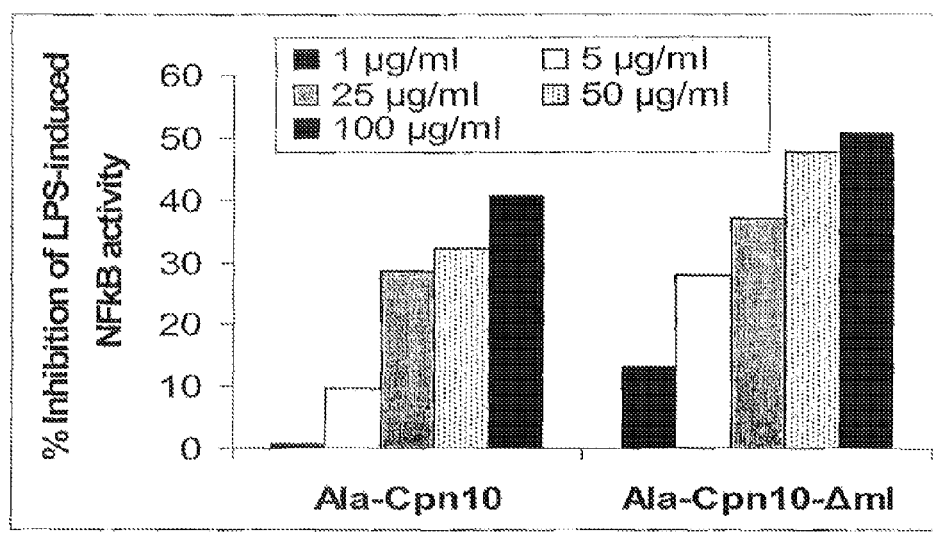

Ala-Cpn10-Δml was tested using the RAW264.7-HIV-LTR-LUC inhibition assay side by side with Ala-Cpn10. In this assay a luciferase reporter is linked indirectly to NF-κB signal transduction. NF-κB is the primary transcription factor induced by LPS. Luciferase activity is measured as relative light units (RLU) or counts per second (CPS) depending on the instrumentation used. As shown in FIGS. 5A and 5B, Ala-Cpn10-Δml inhibited LPS-induced activation of HIV-LTR between the concentrations of 1 and 100 1.1 µg/ml. Although this is a single assay, two replicate experiments were set up on separate microtitre plates and demonstrated the same activity. In this data set, Ala-Cpn10-Δml appeared to possess consistently greater inhibitory activity as compared with Ala-Cpn10.

As described above in Example 8, Ala-Cpn10-Δml was not able to function as a co-chaperone for GroEL in the process of rhodanese refolding. However, when used in the RAW264.7-HIV-LTR-LUC inhibition assay in the presence of LPS, Ala-Cpn10 levels of activity of Ala-Cpn10-Δml was observed. That is, Ala-Cpn10-Δml dose-dependently inhibited LPS-induced activation of the HIV-LTR reporter. These results clearly rule out an involvement of Cpn60 in the ability of Cpn10 to modulate TLR4 signalling.

Example 10

Ala-Cpn10-Δroof Inhibits LPS-induced Activation of HIV LTR

The β-hairpin roof loop region (see FIG. 1) of Cpn10 contains a net positive charge in mammals but predominantly a net negative charge in bacteria (for example as represented by E. coli GroES). Intriguingly, bacteriophage T4 also contains a specialized Cpn10 (Gp31) that functions together with E. coli GroEL to fold the T4 major capsid protein Gp23. Neither GroES nor Cpn10 can fulfill this function. A major difference between Gp31 and Cpn10/GroES is that Gp31 completely lacks the roof β-hairpin loop, possibly accounting for the unusual function and abilities of Gp31 (Hunt et al, 1997, Cell 90: 361-371).

To determine the contribution of the roof β-hairpin region to Cpn10 immunomodulatory activity, 7 amino acids were deleted from the β-hairpin region (SEQ ID NO:13) to generate the 95 amino acid variant designated Ala-Cpn10-Δroof (see Example 6). The amino acid sequence of Ala-Cpn10-Δroof is set forth in SEQ ID NO:26.

Figure 6A:
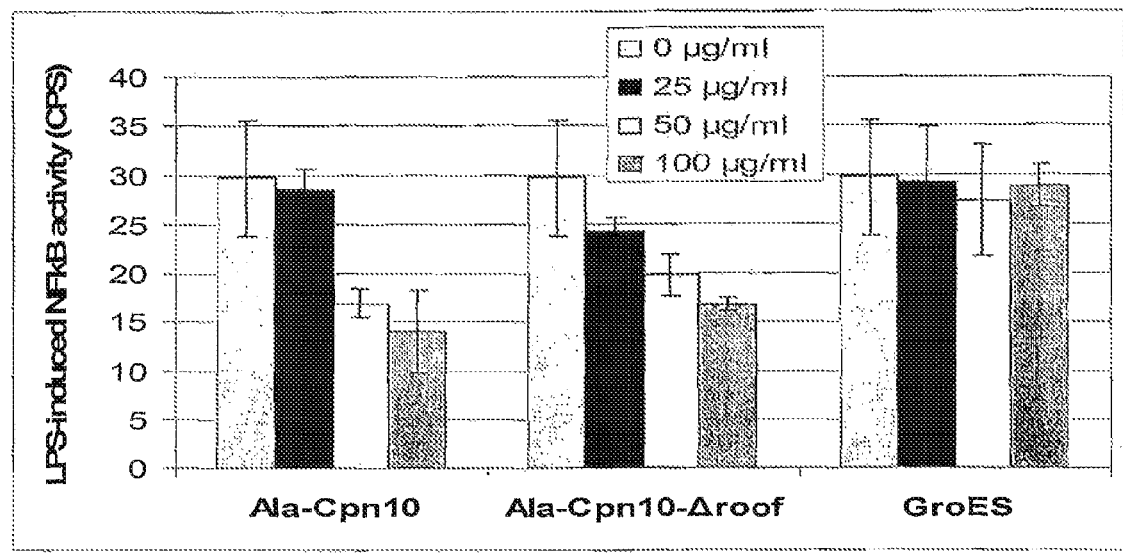
FIG. 6. Effect of Ala-Cpn10 and Ala-Cpn10Δroof and *E. Coli* GroES on TLR4 signalling. Dose-responsive inhibition of LPS-induced HIV-LTR activation by human Ala-Cpn10 (batch CH001) and Ala-Cpn10-Δroof. Panel B shows the results from panel A as percent inhibition of luciferase activity (NFκB activity) relative to the levels of luciferase produced with LPS alone. The LPS alone samples are the mean of 6 replicates, all other samples are the mean of 2 replicates. CPS=relative counts per seconds. NFκB activity was induced with 5 ng/ml Lipopolysaccharide (LPS).
Figure 6B:
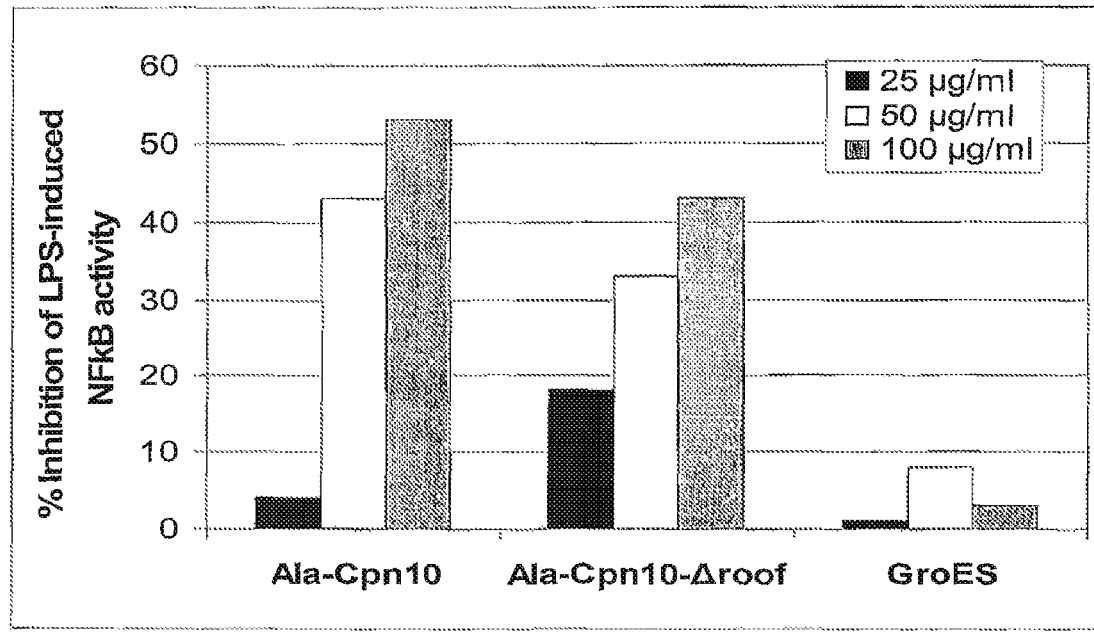

Ala-Cpn10-Δroof was tested in the RAW264.7-HIV-LTR-LUC inhibition assay in the presence of LPS, side by side with Ala-Cpn10 and E. coli GroES. As shown in FIG. 6, Ala-Cpn10-Δroof inhibited LPS-induced activation of HIV-TLR between the concentrations of 50 and 100 µg/ml. Although this is a single assay, two replicate experiments were set up on separate microtitre plates and demonstrated the same activity. In this data set, Ala-Cpn10-Δroof appeared to possess consistently ~80% of the activity of Ala-Cpn10. These results demonstrate that modulation of TLR4 signalling by Cpn10 can occur in the absence of a functional roof β-hairpin region of the molecule.

Example 11

Ala-Cpn10 β-barrel Mutant Exhibits Immunomodulatory Activity

As a confirmation of the above data described in Examples 9 and 10, the inventors generated a human Ala-Cpn10 mutant which lacks both the mobile loops and the β-hairpin roof loops (termed "Ala-Cpn10-β-barrel"; SEQ ID NO:28; see Example 6). Interestingly, the Ala-Cpn10-β-barrel mutant runs as a slightly larger entity on gel filtration chromatography compared with Ala-Cpn10 and the Ala-Cpn10-Δml mutant. This may imply that the roof helps to hold the subunits in a tightly bound conformation. In comparison, the mobile loop destabilizes the heptamer leading to more efficient disassembly; despite this the heptamer is energetically more favored than the disassembled monomers.

Figure 7A:
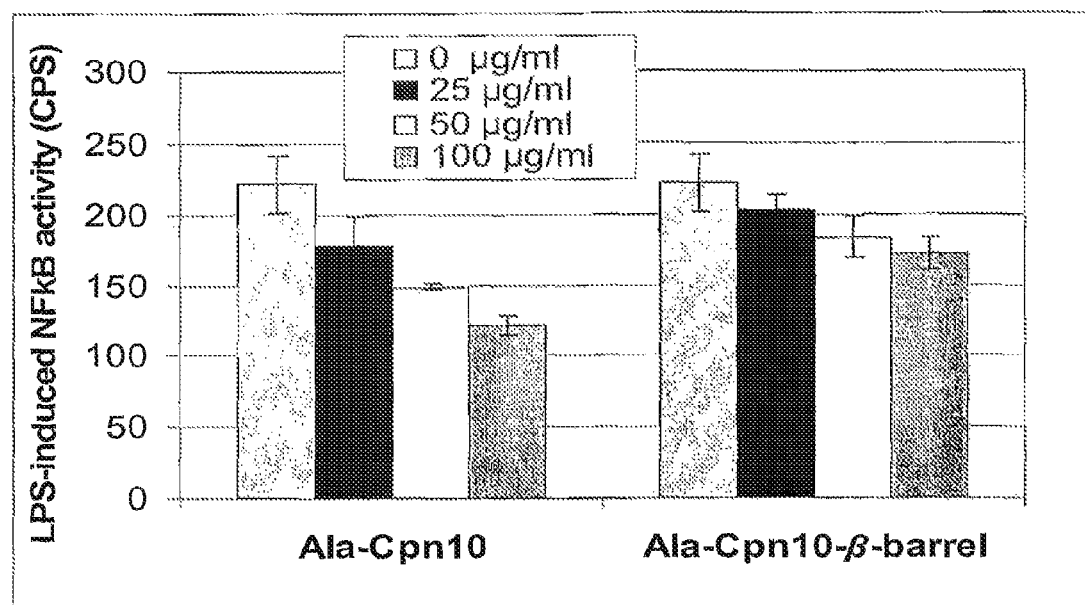
FIG. 7. Effect of Ala-Cpn10 and Ala-Cpn10-β-barrel on TLR4 signalling. Dose-responsive inhibition of LPS-induced HIV-LTR activation by human Ala-Cpn10 (batch CH001) and Ala-Cpn10-β-barrel. Panel B shows the results from panel A as percent inhibition of luciferase activity (NFκB activity) relative to the levels of luciferase produced with LPS alone. The LPS alone samples are the mean of 6 replicates, all other samples are the mean of 2 replicates. CPS=relative counts per seconds. NFκB activity was induced with 5 ng/ml Lipopolysaccharide (LPS).
Figure 7B:
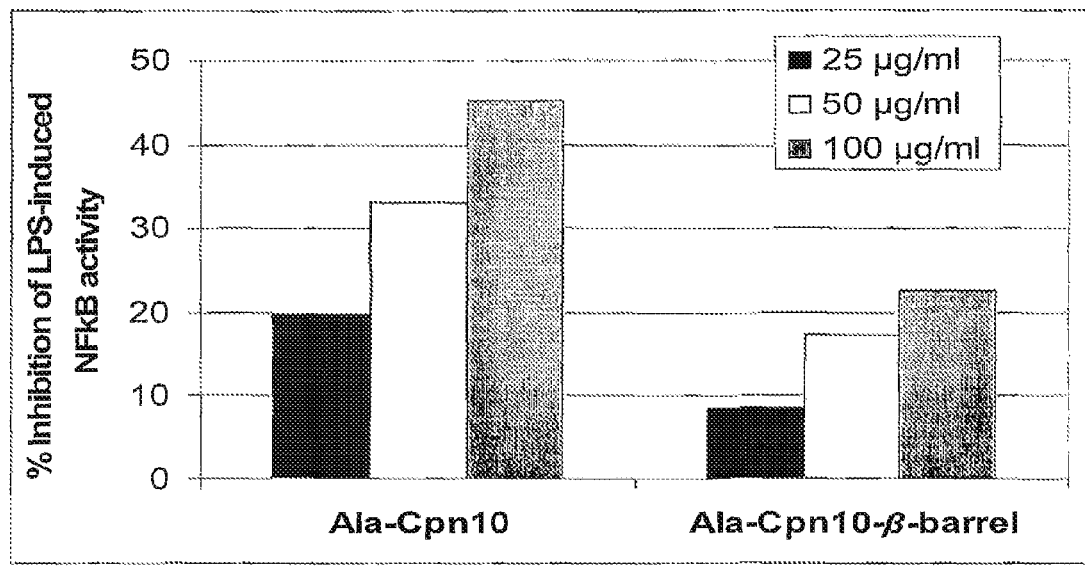

The Ala-Cpn10-β-barrel polypeptide was tested in the RAW264.7-HIV-LTR-LUC inhibition assay in the presence of LPS, side by side with Ala-Cpn10 and E. coli GroES. As shown in FIG. 7, this mutant displayed approximately 50% of the Ala-Cpn10 activity in modulating TLR4 signalling, suggesting that immunomodulatory activity may be partly contributed to the β-hairpin roof loops or might be attributed to stability of the heptamer. The results shown are reflective of two independent experiments.

Example 12

Immunomodulatory Activity of an N-terminal Cpn10 Mutant

The Cpn10 N-terminus is known to assist in targeting to the mitochondrial matrix (following synthesis in the cytosol). However, while most mitochondrial matrix proteins bear a cleavable N-terminal targeting sequence, the Cpn10 N-terminus is not cleaved indicating that it may have a further function.

The inventors have investigated the ability of an N-terminal mutant of human Cpn10 to modulate immune reactivity in vitro. The mutant tested (referred to herein as "Cpn10-NtermES") bears the N-terminal sequence "MNIR" from E. coli GroES in place of the human N-terminal sequence "MAGQAFRKFL". The amino acid sequence of Cpn10-NtermES is provided in SEQ ID NO:14.

The Cpn10-NtermES, showed only ~12% of Ala-Cpn10 activity in chaperone mediated rhodanese refolding (with GroEL; see Table 4). It was however confirmed by gel filtration chromatography that Cpn10-NtermES is a heptamer with intact mobile loops for GroEL (Cpn60) binding (data not shown).

Figure 8A:
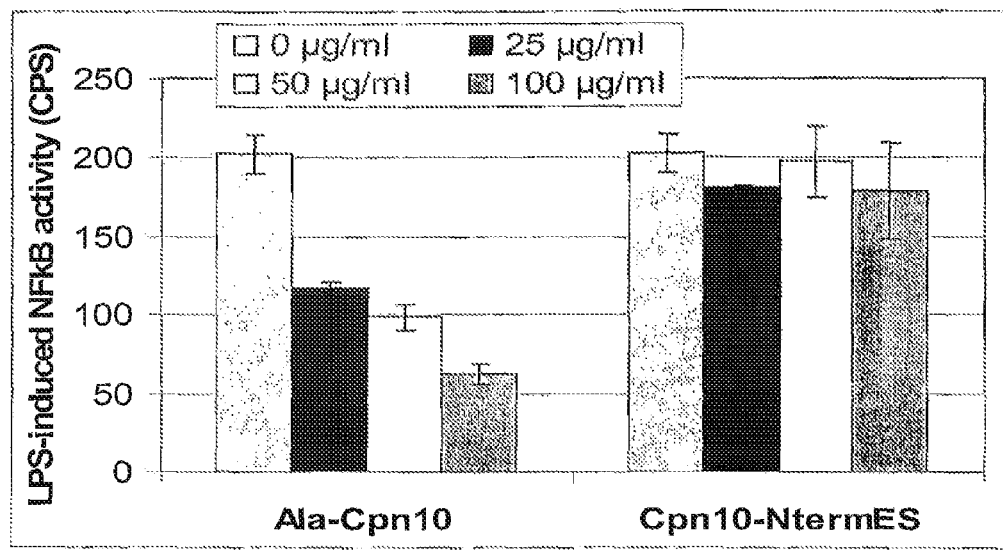
FIG. 8. Effect of Ala-Cpn10 and Cpn10-NtermES on TLR4 signalling. Dose-responsive inhibition of LPS-induced HIV-LTR activation by human wild-type Cpn10 (batch CH001) but not Cpn10-NtermES. Panel B shows the results from panel A as percent inhibition of luciferase activity (NFκB activity) relative to the levels of luciferase produced with LPS alone. The LPS alone samples are the mean of 6 replicates, all other samples are the mean of 2 replicates. CPS=relative counts per seconds; SD=standard deviation. NFκB activity was induced with 5 ng/ml Lipopolysaccharide (LPS).
Figure 8B:
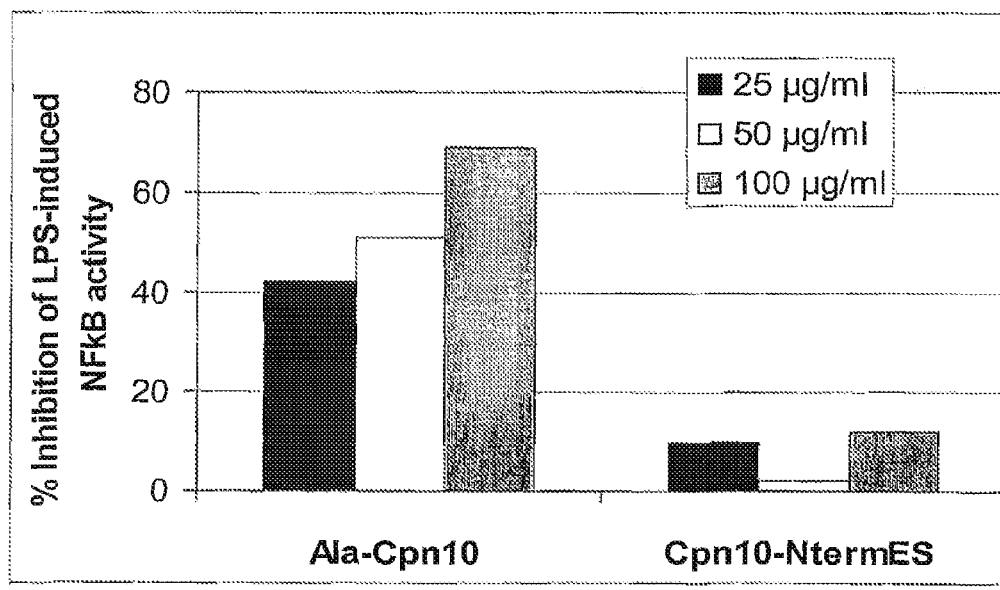
Figure 9A:
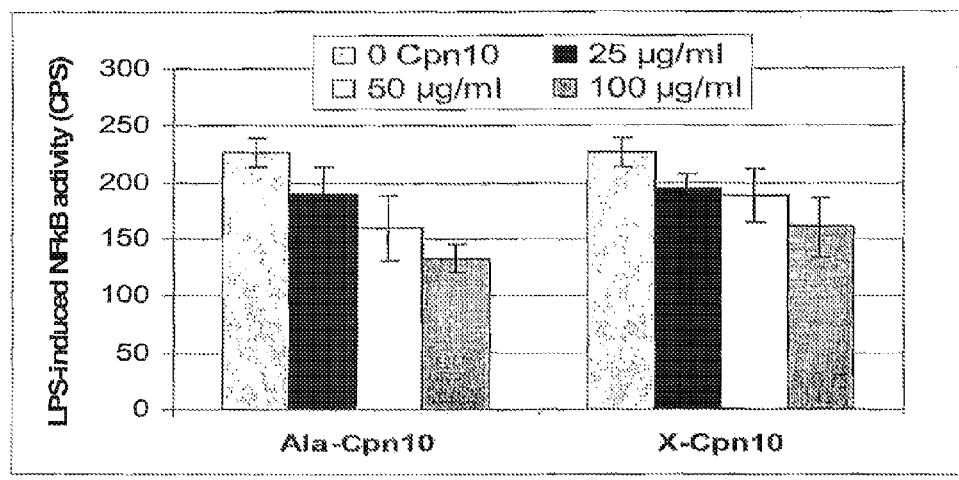
FIG. 9. Effect of Ala-Cpn10 and X-Cpn10 on TLR4 signalling. Dose-responsive inhibition of LPS-induced HIV-LTR activation by human Ala-Cpn10 (batch CH003) and X-Cpn10. Panel B shows the results from panel A as percent inhibition of luciferase activity (NFκB activity) relative to the levels of luciferase produced with LPS alone. The LPS alone samples are the mean of 6 replicates, all other samples are the mean of 2 replicates. CPS=relative counts per seconds. NFκB activity was induced with 5 ng/ml Lipopolysaccharide (LPS).
Figure 9B:
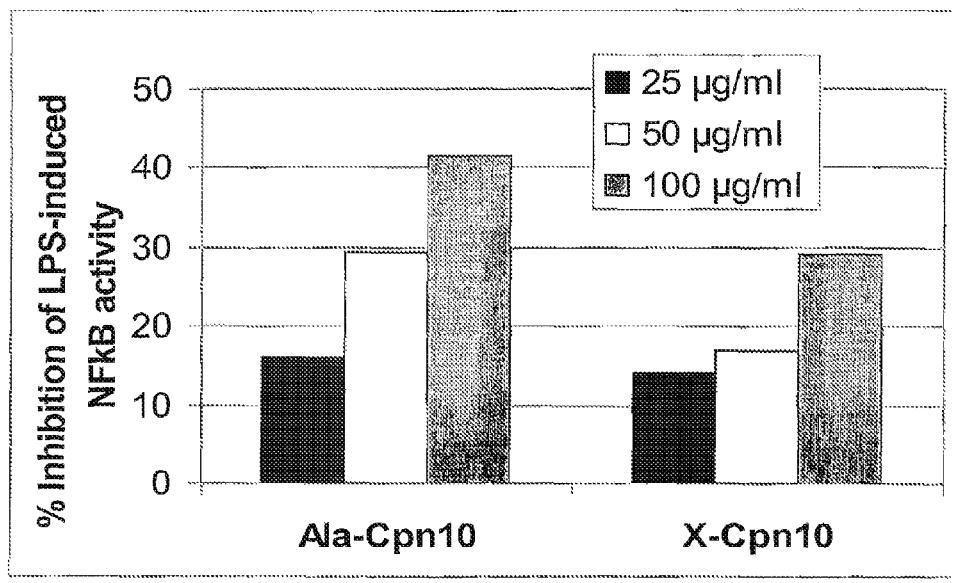
Figure 10A:
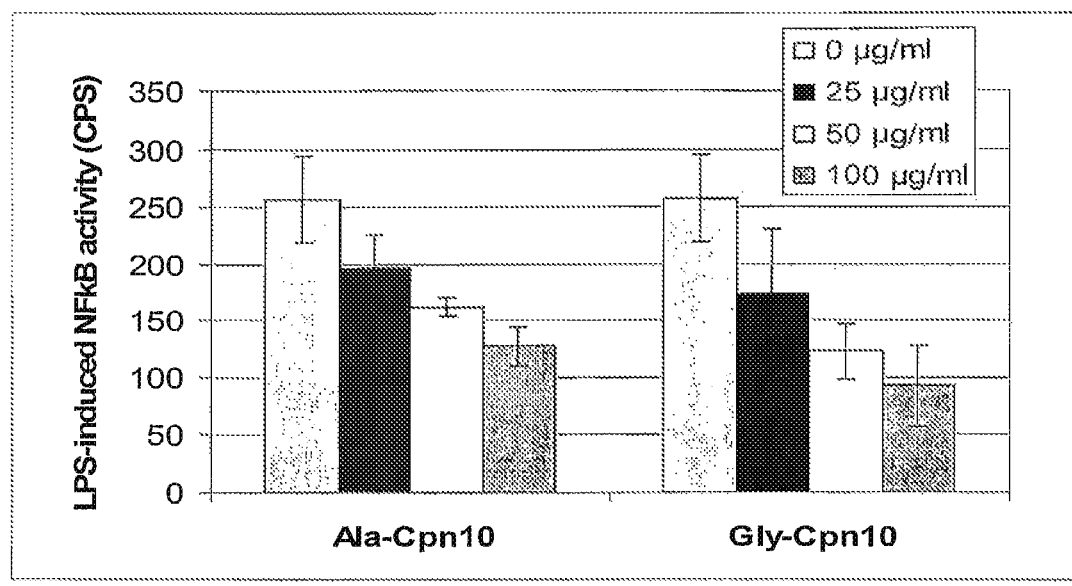
FIG. 10. Effect of Ala-Cpn10 and Gly-Cpn10 on TLR4 signalling. Dose-responsive inhibition of LPS-induced HIV-LTR activation by human Ala-Cpn10 (batch CH003) and Gly-Cpn10. Panel B shows the results from panel A as percent inhibition of luciferase activity (NFκB activity) relative to the levels of luciferase produced with LPS alone. The LPS alone samples are the mean of 6 replicates, all other samples are the mean of 2 replicates. CPS=relative counts per seconds. NFκB activity was induced with 5 ng/ml Lipopolysaccharide (LPS).
Figure 10B:
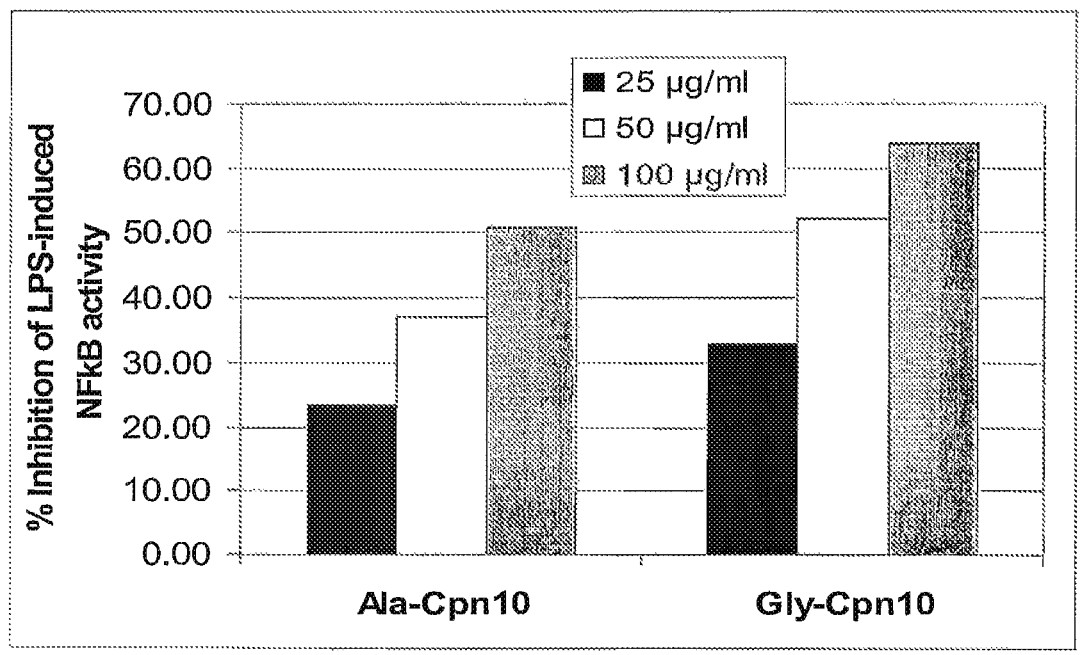
Figure 11A:
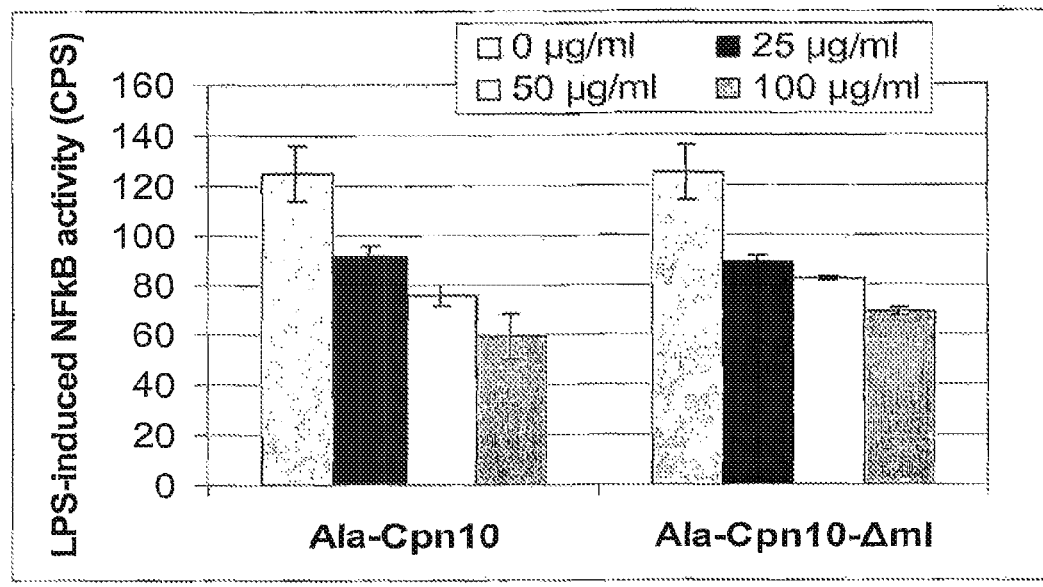
FIG. 11. Effect of Ala-Cpn10 and Ala-Cpn10-Δml on TLR4 signalling. Dose-responsive inhibition of LPS-induced HIV-LTR activation by human Ala-Cpn10 (batch CH003) and Ala-Cpn10-Δml. Panel B shows the results from panel A as percent inhibition of luciferase activity (NFκB activity) relative to the levels of luciferase produced with LPS alone. The LPS alone samples are the mean of 6 replicates, all other samples are the mean of 2 replicates. CPS=relative counts per seconds. NFκB activity was induced with 5 ng/ml Ultra-Pure Lipopolysaccharide (LPS).
Figure 11B:
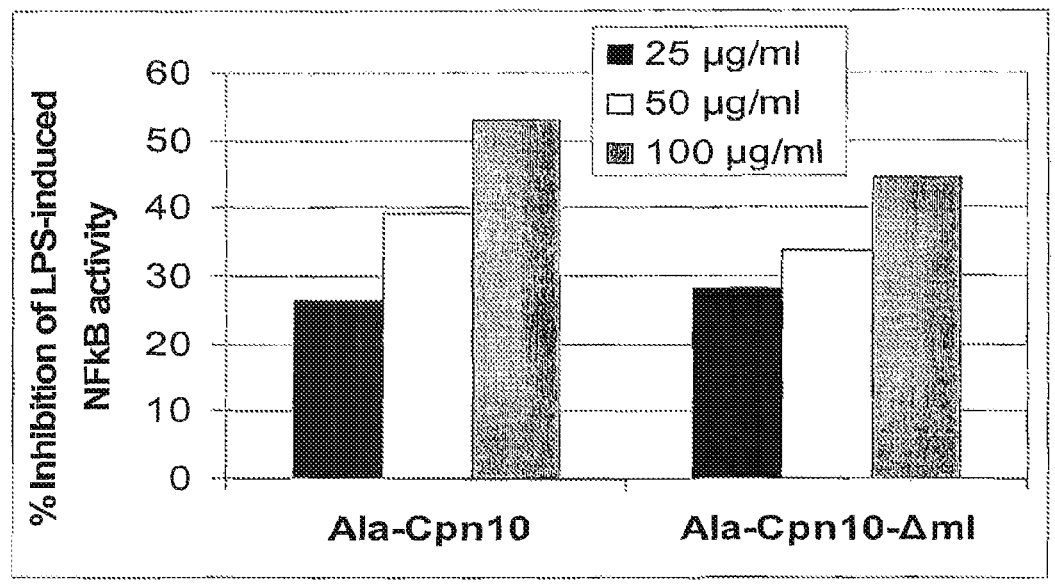
Figure 12A:
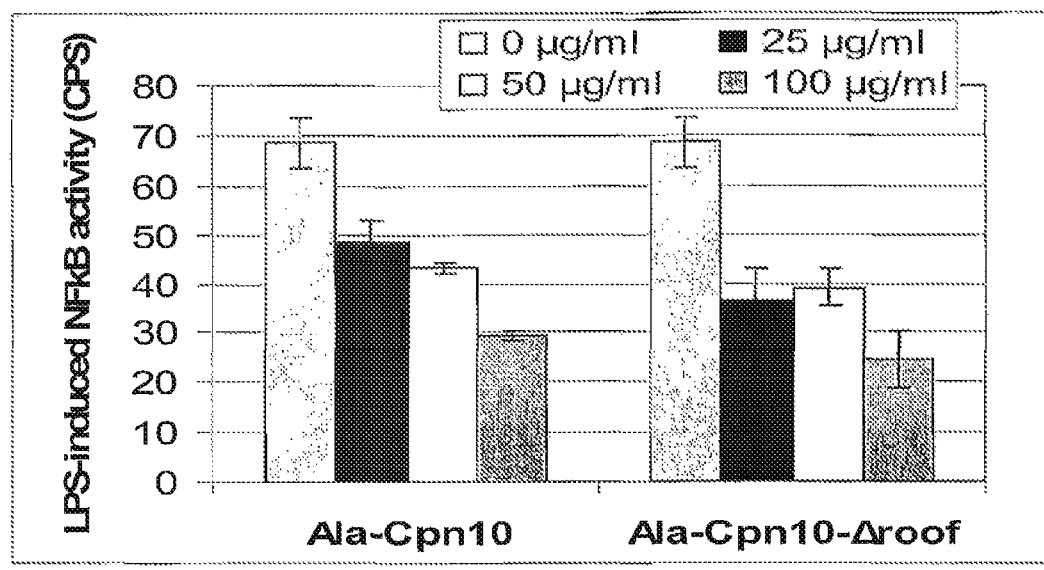
FIG. 12. Effect of Ala-Cpn10 and Ala-Cpn10-Δroof on TLR4 signalling. Dose-responsive inhibition of LPS-induced HIV-LTR activation by human Ala-Cpn10 (batch CH003) and Ala-Cpn10-Δroof. Panel B shows the results from panel A as percent inhibition of luciferase activity (NFκB activity) relative to the levels of luciferase produced with LPS alone. The LPS alone samples are the mean of 6 replicates, all other samples are the mean of 2 replicates. CPS=relative counts per seconds. NFκB activity was induced with 5 ng/ml Ultra-Pure Lipopolysaccharide (LPS).
Figure 12B:
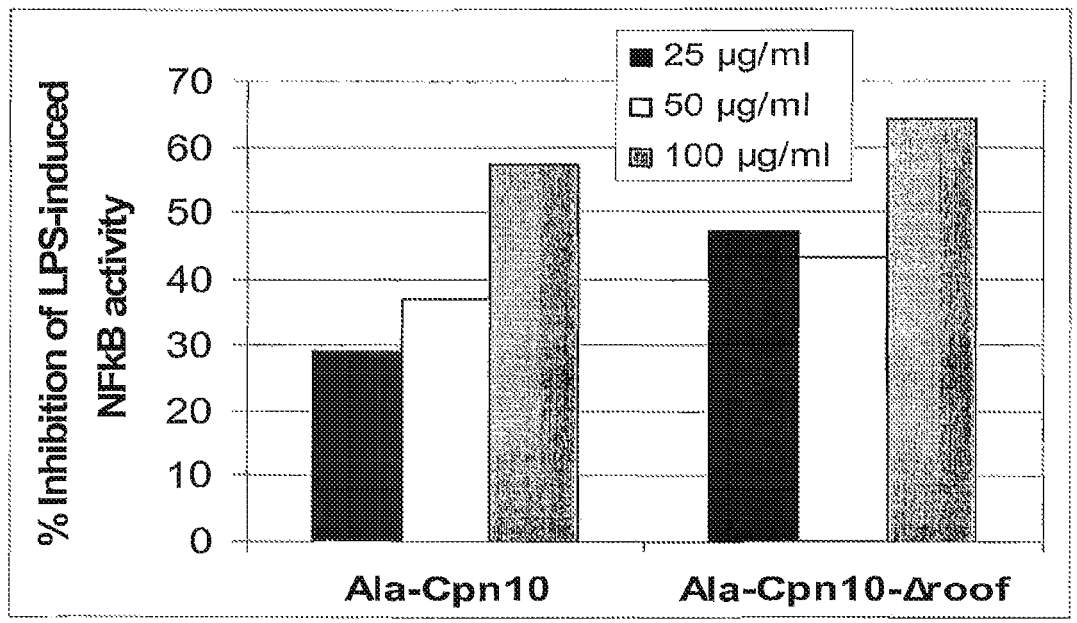
Figure 13A:
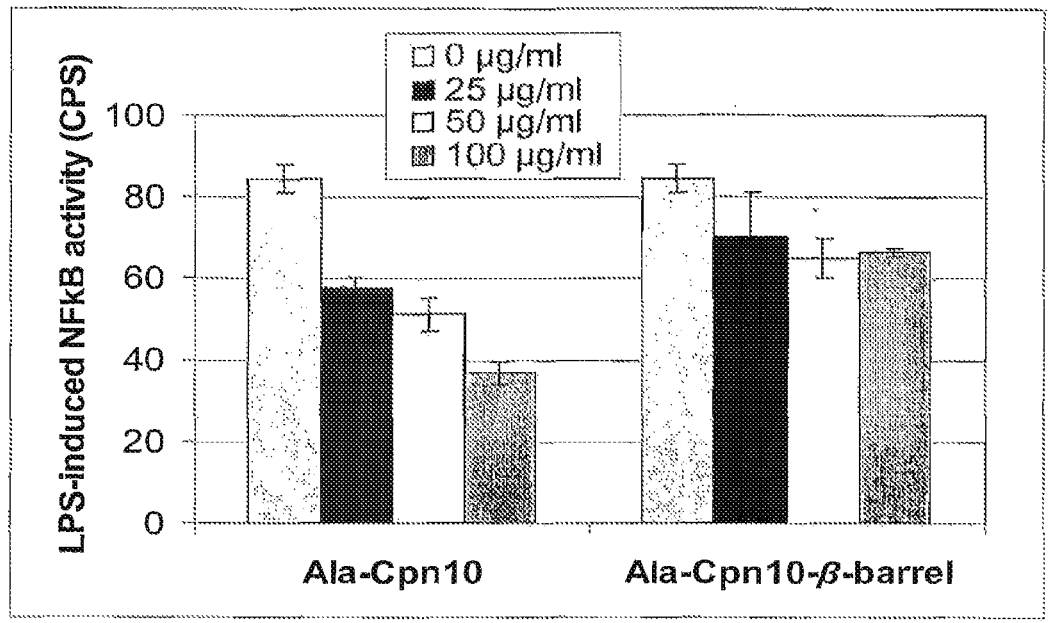
FIG. 13. Effect of Ala-Cpn10 and Ala-Cpn10-β-barrel on TLR4 signalling. Dose-responsive inhibition of LPS-induced HIV-LTR activation by human Ala-Cpn10 (batch CH003) and Ala-Cpn10-β-barrel. Panel B shows the results from panel A as percent inhibition of luciferase activity (NFκB activity) relative to the levels of luciferase produced with LPS alone. The LPS alone samples are the mean of 6 replicates, all other samples are the mean of 2 replicates. CPS=relative counts per seconds. NFκB activity was induced with 5 ng/ml Ultra-Pure Lipopolysaccharide (LPS).
Figure 13B:
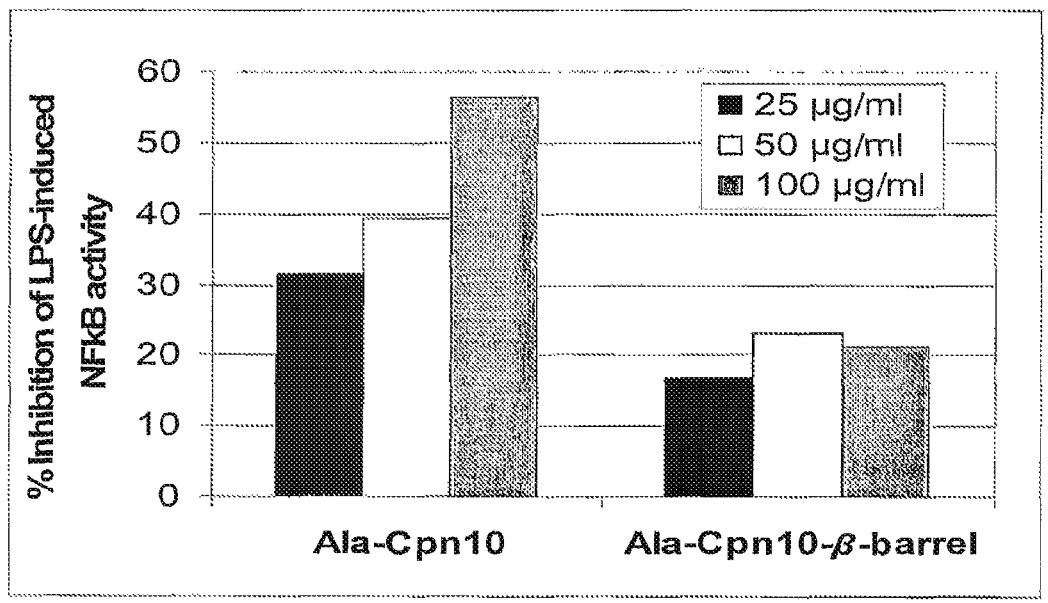
Figure 14A:
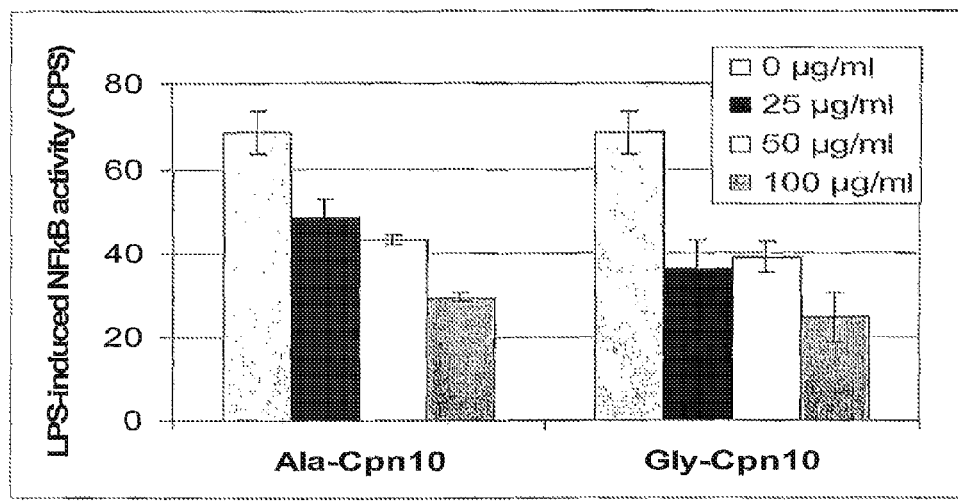
FIG. 14. Effect of Ala-Cpn10 and Gly-Cpn10 on TLR4 signalling. Dose-responsive inhibition of LPS-induced HIV-LTR activation by human Ala-Cpn10 (batch CH003) and Gly-Cpn10. Panel B shows the results from panel A as percent inhibition of luciferase activity (NFκB activity) relative to the levels of luciferase produced with LPS alone. The LPS alone samples are the mean of 6 replicates, all other samples are the mean of 2 replicates. CPS=relative counts per seconds. NFκB activity was induced with 5 ng/ml Ultra-Pure Lipopolysaccharide (LPS).
Figure 14B:
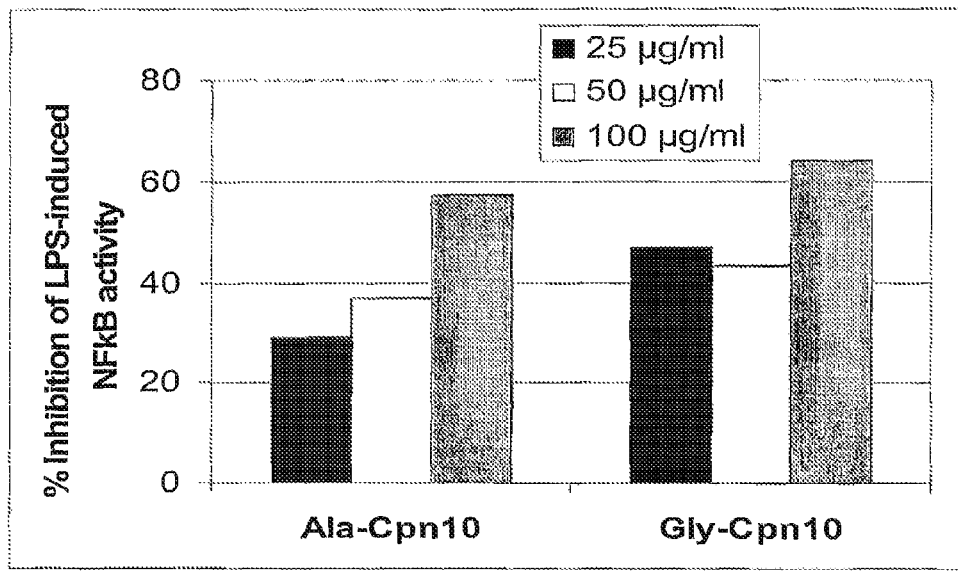
Figure 16:
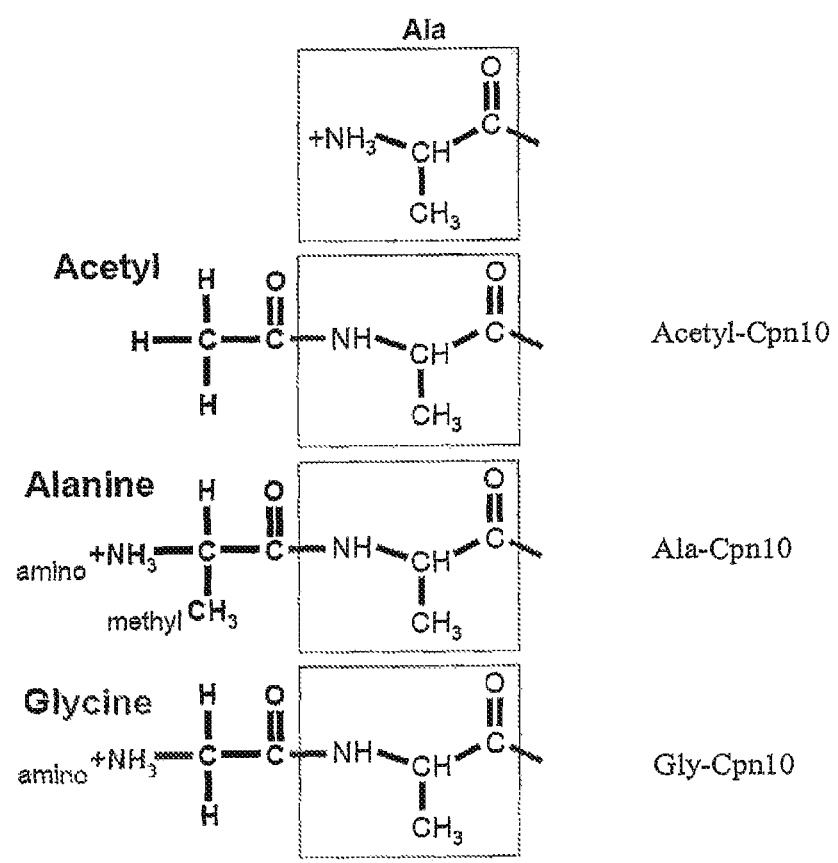
FIG. 16. Partial structural formulas showing chemical similarity and relationship of acetyl, alanine, and glycine in Acetyl-Cpn10, Ala-Cpn10, and Gly-Cpn10.

As shown in FIGS. 8A and 8B, the Cpn10-NtermES mutant lost the ability to immunomodulate LPS-induced activation of HIV-TLR in contrast to the activity observed with Ala-Cpn10. This indicates that the N-terminus of Cpn10 is required for Cpn10 immunomodulatory activity involving TLR4. Therefore, ES-Nterm-Cpn10, like *E. coli* (GroES), was unable to suppress NF-κB induced by LPS (i.e. TLR4 modulation) (see FIG. 8B).

Example 13

Reduced Ability of X-Cpn10 to Inhibit LPS-induced Activation of HIV LTR

X-Cpn10 was tested using the RAW264.7-HIV-LTR-LUC inhibition assay side by side with Ala-Cpn10. As discussed in example 6, X-Cpn10 lacks the extra N terminal alanine residue and an acetyl group which is present in native human Cpn10. In this assay a luciferase reporter is linked indirectly to NF-κB signal transduction. NF-κB is the primary transcription factor induced by LPS. Luciferase activity is measured as relative light units (RLU) or counts per second (CPS) depending on the instrumentation used. As shown in FIGS. 9A and 9B, X-Cpn10 partially inhibited LPS-induced activation of HIV-LTR (approximately 50% of Ala- or Gly-Cpn10 activity). In this data set, it appears that additional residues on the N-terminus of Cpn10 such as an alanine may contribute to the immunomodulatory activity of TLR4 signalling.

Example 14

Gly-Cpn10 Inhibits LPS-induced Activation of HIV LTR

Gly-Cpn10 was tested using the RAW264.7-HIV-LTR-LUC inhibition assay side by side with Ala-Cpn10. As discussed in example 6, Gly-Cpn10 contains a glycine residue which replaced the extra N-terminal alanine residue of Ala-Cpn10. In this assay a luciferase reporter is linked indirectly to NF-κB signal transduction. NF-κB is the primary transcription factor induced by LPS. Luciferase activity is measured as relative light units (RLU) or counts per second (CPS) depending on the instrumentation used. As shown in FIGS. 10A and 10B, Gly-Cpn10 inhibited LPS-induced activation of HIV-LTR to a greater extent than Ala-Cpn10.

As shown in the FIG. 16, an acetyl group is more structurally similar to a glycine residue than an alanine residue. It is therefore contemplated that the activity of the Acetyl-Cpn10 polypeptide (i.e. native Cpn10) is similar to Gly-Cpn10.

Example 15

Use of Ultra Pure LPS in RAW264.7-HIV-LTR-LUC Inhibition Assay

The data as shown in FIGS. 5-7 and 10 were generated by using crude LPS in the abovementioned RAW264.7-HIV-LTR-LUC inhibition assay. In FIGS. 11 to 14, ultra pure LPS was used which is specific for TLR4. The results from FIGS. 11 (Ala-Cpn10-Δml), 12 (Ala-Cpn10-Δroof), 13 (Ala-Cpn10-β-barrel) and 14 (Gly-Cpn10) are very similar to their counterparts as represented in FIGS. 5-7 and 10. This shows that the assays that are used and disclosed herein for the generation of the immunomodulatory activity of Cpn10 are specific for TLR4.

Example 16

Mouse Endotoxemia Study

A mouse endotoxemia study was undertaken to determine whether the in vitro immunomodulatory activity of various Cpn10 polypeptides (i.e. Ala-Cpn10-Δml, Ala-Cpn10-Δroof, and X-Cpn10) reflects the in vivo activity using a mouse model of sepsis. By systematically changing or deleting hypothesized active regions of the Cpn10 molecule, and by testing homologues of Cpn10 from the numerous biological kingdoms, the minimal structural regions and/or sequence-based motifs necessary for optimal activity can be described, leading ultimately to the ability to design a more potent molecule for therapeutic use. To date several variations or mutations in Cpn10 have been made in order to examine the importance of these regions for immunomodulatory activity (see FIG. 1).

From these in vitro studies, it has been observed that relative to Ala-Cpn10, constructs with a deletion in the mobile loop or roof loop region of Cpn10 (i.e. Ala-Cpn10-Δml and Ala-Cpn10-Δroof respectively), showed comparable activity in terms of reducing NF-κB activation in response to ligation of TLR4 with LPS. On the other hand, the non-acetylated Cpn10 (X-Cpn10) showed significantly reduced ability to down-modulate NF-κB activity using this in vitro assessment of activity.

In the present study a number of Cpn10 variants were found to have similar activity to Ala-Cpn10 in an in vivo model of inflammation (i.e. endotoxemia). The mouse endotoxemia model measures the ability of Cpn10 to reduce LPS-induced inflammatory cytokine production.

Example 16a

Material and Methods for the Mouse Endotoxemia Study

The following materials and methods used in the mouse endotoxemia study are described below in examples 17a(1) to 17(a)2.

Example 16a(1)

Mice Used for the Endotoxemia Study

The study was conducted on 84 female Balb/c mice. All were adult (>9 weeks of age, average weight −20 g (0.02 kg)), and divided into twelve groups with seven mice per group (see Table 5). The mice were housed with a 12/12 light/dark cycle and have access to standard laboratory chow (Specialty Feeds, Glen Forrest, Australia) and water ad lib. The weight of each mouse was measured prior to the start of injections. The groups received the following injections via intravenous (IV) route into the tail vein as shown below (see Table 5).

Example 16a(2)

Drugs/Solutions for the Mouse Endotoxemia Study

The drugs/solutions used in the mouse endotoxemia study are the following (listed from (A) to (H)).

(A) Protein formulation buffer (FB): This buffer is the negative control within the study and comprises 50 mM Tris-HCl (pH 7.6)+150 mM NaCl (<0.02 EU/ml). This buffer is to be used as a test article and diluent for positive control and test samples.

(B) Ala-Cpn10: This Cpn10 polypeptide is the positive control within the study and has a stock concentration of 5 mg/ml (<0.01 EU/mg). A 1 mg/ml working solution was made by diluting 4000 of the protein solution into 1.6 ml of formulation buffer.

(C) Ala-Cpn10-Δml: This Cpn10 polypeptide has a stock concentration of 3.5 mg/ml (<0.03 EU/mg). A 1 mg/ml working solution was made by diluting 571 µl of the protein solution into 1.429 ml of formulation buffer.

(D) Ala-Cpn10-Δroof: This Cpn10 polypeptide has a stock concentration of 4.2 mg/ml (<0.1 EU/mg). A 1 mg/ml working solution was made by diluting 477 µl of the protein solution into 1.523 ml of formulation buffer.

(F) X-Cpn10: This Cpn10 polypeptide has a stock concentration of 5 mg/ml (<0.04 EU/mg). A 1 mg/ml working solution was made by diluting 4000 of the protein solution into 1.6 ml of formulation buffer.

(G) Endotoxin: Lipopolysaccharide (LPS) was obtained Sigma Chemical Company (Cat. No. L6529) Immediately prior to use, vial contents (1 mg) were reconstituted in 1 ml sterile saline. Contents were further diluted (1/10) to 100 µg/ml in sterile saline prior to injection of each group.

(H) Endotoxin Control: Sterile saline for injection was obtained from Pfizer, Australia (Cat. No. DW-SC0010) at a concentration of 900 mg/ml (0.9%) (<0.01 EU/ml).

Example 16b

Drug Administration and Blood Collection for the Mouse Endotoxemia Study

The protocol for the drug administration in different groups of mice is as shown in Table 5 (see below). All administrations were carried out via tail vein injections of 100 µl volumes on conscious, restrained mice. All LPS doses were 10 µg/mouse. All Cpn10 variants were injected at 100 µg/mouse (100 µL of volume).

The protocol for blood collections is outlined below in Table 5. Blood samples were collected via cardiac puncture under halothane anaesthesia (Zeneca Ltd., Macclesfield, UK) (SOP ET-011) or via post-mortem open-heart bleed. The blood was collected into paediatric serum tubes with no anticoagulant (clot activator), (Greiner-bio-one, USA, Cat#450401). The samples were left at room temperature for approximately 5 min to improve coagulation prior to centrifugation at 12000 rpm for 5 min (Biofuge 13, Heraeus Instruments) at room temperature. The serum was transferred to a fresh tube and placed at −20° C. prior to shipping on dry ice.

All drug administration and blood collection times were recorded on the clinical record sheets (Form IMVS 2061/A). The same record sheets were used to monitored general condition throughout the course of the experiment.

TABLE 5

| Protocol for Cpn10 Endotoxemia study. | | | | |
|---|---|---|---|---|
| Groups | Mice identity numbers | Drug administration times (T) | | Blood collection time |
| | | T = 0 min | T = 30 min | T = 2 hr |
| 1 | 1-7 | FB | LPS | All |
| 2 | 8-14 | FB | Saline | All |
| 3 | 15-21 | Ala-Cpn10 | LPS | All |
| 4 | 22-28 | Ala-Cpn10 | Saline | All |
| 5 | 29-35 | Ala-Cpn10-Δml | LPS | All |
| 6 | 36-42 | Ala-Cpn10-Δml | Saline | All |
| 7 | 43-49 | Ala-Cpn10-Δroof | LPS | All |
| 8 | 50-56 | Ala-Cpn10-Δroof | Saline | All |
| 11 | 71-77 | X-Cpn10 | LPS | All |
| 12 | 78-84 | X-Cpn10 | Saline | All |

Example 16c

Cytometric Bead Array (CBA) Analysis

Mouse inflammation CBA analysis (Cat#552364, BD Biosciences) was performed on serum samples to assess for changes in the level of inflammation associated cytokines (i.e. TNFα, IL6, IL-10, MCP-1, IL12p 70, IFN-γ). Sera from LPS-challenged mice (Table 5, groups 1, 3, 5, 7, 9 and 11) or Saline control mice (Table 5, groups 2, 4, 6, 8, 10 and 12) were diluted prior to analysis in assay diluent as appropriate (1 in 5 for LPS treated groups and 1 in 2 for saline controls). Each sample was analyzed in duplicate as per manufacturer's instruction using BD FACS-Array instrument with the CBA software.

Example 16d

Percent Cytokine Level Reduction Measurement

The following formula was used to determine the effect of Cpn10 treatment on LPS challenged mice. The percent reduction of LPS-induced cytokine in mice pretreated with Cpn10 variants (i.e. Experimental) relative to non-pretreated mice (i.e. Control) was calculated according to the following formula: % reduction=100−((mean cytokine level of Experimental/mean cytokine of Control)×100].

Example 16e

ELISA Analysis

Mouse TNF-α ELISA was carried out using RnD Systems Duoset ELISA kit (Cat#DY410) as per manufacturer's instruction to confirm the CBA analysis. Dilutions of the samples (1 in 3 dilutions) and standards were performed using PBS-F10% FCS as diluent. Samples were analyzed in duplicate.

Example 16f

Clinical Observations

The behaviour of the various groups of mice described in Table 5, was examined during the 90 min period after LPS or Saline injection and prior to bleeding via cardiac puncture.

All observations were recorded and summarized in Table 6. Observations were made immediately after LPS/saline injection and prior to bleeding of mice by Cardiac Puncture (C.P.). Comparisons of clinical observations were made relative to groups 1, 2 or 3. In general, mice treated with LPS alone (Group 1) showed the effects of LPS-induced sepsis within 15 min of injection. LPS-treated mice demonstrated reduced mobility and were less responsive to stimuli (e.g. noise or touching). Some typical adverse effects due to LPS challenge such as diarrhea or ruffled fur was not observed in any of the mice in this study. This may reflect the relative potency of the lot number of LPS used on this occasion. Saline treated control mice (Group 2) were more responsive to stimulus, exhibiting normal reactions and mobility.

sepsis-associated symptom). Cardiac puncture bleeds in these mice were slower with reduced recovery of blood volume relative to mice which did not receive LPS. For mice which were not able to be bled by direct cardiac puncture, a post-mortem open heart bleed was performed. Cpn10 treatment did not appear to affect or improve blood recovery in LPS treated mice however, in comparison to the LPS control animals, it was noted that blood from Cpn10-treated mice could generally be recovered by direct cardiac puncture without resorting to an open heart bleed. At least 400 µl of blood was recovered from each mouse in this study. All deviations from a normal bleed and recovery were noted on the relevant clinical record sheet.

TABLE 6

Clinical observation of mice pre-treated with various Cpn10 followed with LPS/Saline injection.

| Group #. Treatment | Behavior | Clinical signs |
| --- | --- | --- |
| 1. FB + LPS | Not active, No response to stimuli, Huddling | No ruffled fur or diarrhea Slower/difficult bleeding |
| 2. FB + saline | Active and alert Responsive to stimuli | Normal bleeding |
| 3. Ala-Cpn10 + LPS | Reduced activity, Reduced response to stimuli, Huddling | Normal bleeding |
| 4. Ala-Cpn10 + saline | Active and alert Responsive to stimuli | Normal bleeding |
| 5. Ala-Cpn10-Δml + LPS | Reduced activity Reduced response to stimuli. Reduced huddling | Normal bleeding |
| 6. Ala-Cpn10-Δml + saline | Active and alert Responsive to stimuli | Normal bleeding |
| 7. Ala-Cpn10-Δroof + LPS | Less active, Less response to stimuli, Huddling | Some difficult bleeding |
| 8. Ala-Cpn10-Δroof + saline | Active and alert Responsive to stimuli | Normal bleeding |
| 11. X-Cpn10 + LPS | Not active, Reduced response to stimuli, Huddling | No ruffled fur or diarrhea Slower/difficult bleeding |
| 12. X-Cpn10 + saline | Active and alert Responsive to stimuli | Normal bleeding |

Mice which were pre-treated with Cpn10 and various Cpn10 mutants displayed slightly different behavior in response to LPS challenge, relative to the untreated LPS control group. Mice pre-treated with Ala-Cpn10 and Ala-Cpn10-Δroof (Groups 3 and 7) appeared less subdued, slightly more alert and responsive to stimulus but continued to huddle together for most of the period of observation. Interestingly, mice pre-treated with Ala-Cpn10-Δml (Group 5) were slightly more active and did not huddle as much throughout the observation period. The effect of LPS challenge in mice pre-treated with Acetyl-Cpn10 (Group 9) also appeared different to those observed in other groups. Although these mice showed similar behaviour to Group 3 in the first 30-45 min after LPS injection, these mice appeared to recover towards the end of the observation period and displayed increased mobility and alertness. In contrast, mice pre-treated with X-Cpn10 showed very similar behavior to Group 1. These mice were very much inactive, less responsive to stimulus and huddled together for most of the observation period. The saline controls for each of the Cpn10 mutant groups (i.e. Groups 4, 6, 8, 10 and 12) demonstrated an absence of adverse clinical symptoms similar to control animals in the untreated saline group (Group 2).

The bleeding of mice challenged with LPS was typically more problematic as these mice are generally hypotensive (a Example 16g Reduction of Cytokines in Mice The mean level of TNF-α, IL-6 and IL-10 cytokines in LPS-challenged mice (see FIG. 15) is shown. Cpn10-treated groups demonstrating statistical significance in the reduction of pro-inflammatory cytokines relative to animals which were not treated with Cpn10 are indicated by asterisk (Table 7). The percentage reduction in the various cytokines analysed in mice pre-treated with various Cpn10s relative to non-pre-treated mice (as shown in table 5) are indicated in brackets.

TABLE 7

Mean and percent reduction of LPS-induced pro-inflammatory cytokines in LPS-challenged mice treated with various Cpn10 mutants.

| | Mean and percentage reduction of serum cytokines | | |
| --- | --- | --- | --- |
| Pre-treatment | TNF-a | IL-6 | IL-10 |
| None | 2033 | 5667 | 808 |
| Ala-Cpn10 | 1337 (34%) | 2394* (57%) | 365 (54%) |
| Ala-Cpn10-Δml | 746* (63%) | 4105 (27%) | 539 (33%) |

TABLE 7-continued

Mean and percent reduction of LPS-induced pro-inflammatory cytokines in LPS-challenged mice treated with various Cpn10 mutants.

| Pre-treatment | Mean and percentage reduction of serum cytokines | | |
|---|---|---|---|
| | TNF-a | IL-6 | IL-10 |
| Ala-Cpn10-Δroof | 1010 (50%) | 3052* (46%) | 498 (38%) |
| X-Cpn10 | 969.3* (52%) | 2769* (51%) | 469 (42%) |

CBA Analysis for Serum Cytokine Levels

Serum samples from each mouse were analyzed using the BD Mouse inflammation CBA assay for the detection of circulating pro-inflammatory cytokines. The assay detects TNFα, IL-6, IL-10, IL-12p 70, MCP-1 and IFN-γ cytokines in the test sample. The analyses were performed on samples which were serially diluted (see example 16a) for optimal detection within the limits of the assay. All samples were analyzed in duplicate.

The relative expression of the cytokines TNF-α, IL-6 and IL-10 in control versus Cpn10-treated animals as indices of inflammation in this mouse sepsis model was examined. In the time frame of this endotoxemia study (90 min LPS administration), levels of IFN-γ, MCP-1 and IL-12p 70 cytokines are generally outside the detection limits of this assay and therefore the data is not presented here. As such, these cytokines were not examined in this study. Prior to analysis of the CBA results, we assessed the robustness of the data based on consistency between replicates and where the data point fell with respect to the linear range of the standard curve. Extreme outliers were excluded from the analysis.

The absolute value and mean of circulating TNF-α, IL-6 and IL-10 in the various groups of mice in this study are shown in FIG. 15. As expected the mean level of TNF-α, IL-6 and IL-10 cytokines were higher in sera derived from mice challenged with LPS relative to their saline controls (FIGS. 15A, C, E vs B, E, F respectively). This indicates that the amount of LPS used in this study induced an inflammatory response and that the background levels of these cytokines were sufficiently low in these mice. In some saline control samples (FIG. 15F, "X-Cpn10+Saline") the level of IL-10 detected was as high as to what was detected in LPS-challenged control (i.e. Group 1-"FB+LPS"). These samples were analyzed in a more concentrated form and thus endogenous serum factors may have interfered with the assay readout thus contributing to inaccuracies with this data. The data also show that mice challenged with LPS have reduced serum TNF-α, IL-6 and IL-10 cytokine levels when pre-treated with any of the Cpn10 proteins compared to non-Cpn10 pre-treated mice (FIGS. 15A, C and E, respectively). For each cytokine profile, a one-way ANOVA analysis (with Tukey's post-hoc test) was performed. The analysis found that some of the means of TNF-α and IL-6 level but not IL-10 cytokine level in the various groups are statistically different (FIGS. 15A, C and E). The lack of statistical difference in the IL-10 cytokine level despite the apparent reduction of mean cytokine level shown on the plot is likely due to the large variation of the IL-10 cytokine in the control group alone (FIG. 15E, "FB+LPS"). A larger sampling population may improve the statistical significance of these observations for future studies.

Tukey's post-hoc tests showed that the mean TNF-α and IL-6 cytokine levels in groups pre-treated with either Ala-Cpn10-Δroof or X-Cpn10 (i.e. Groups 7 and 11) was considered to be statistically lower relative to the untreated group (i.e. Group 1) (Table 7). However, in some groups, a statistically significant reduction in pro-inflammatory cytokines (relative to the untreated group) was only seen in one of the cytokine profiles. For example, Ala-Cpn10-Δml pre-treated group had a reduced mean TNF-α but not IL-6 cytokine levels relative to the untreated group and vice versa for Ala-Cpn10 pre-treated group (Table 7). Furthermore, statistical analysis did not find the mean cytokine levels of the Cpn10 variant pre-treated groups relative to each other to be different.

Despite statistical significant reduction in only some of the Cpn10 variant pre-treated group, the overall trend showed that all Cpn10 variants reduced inflammatory-associated cytokines in LPS-challenged mice. Overall approximately 30 to 50% reduction of TNF-α, IL-6 and IL-10 cytokines level in these mice were observed (Table 7).

Discussion and Conclusions

This study showed that pre-treatment of mice with various Cpn10 polypeptides (i.e. Ala-Cpn10, Ala-Cpn10-Δml, Ala-Cpn10-Δroof, and X-Cpn10) appeared to reduce clinical effects of LPS-induced endotoxemia. Mice which received LPS alone displayed typical symptoms of endotoxemia (i.e. reduced activity, responsive and alertness). On the other hand, mice pre-treated with any of the Cpn10 proteins appeared less affected by LPS challenge (i.e. more responsive and mobile to stimulus) (Table 6).

CBA analysis for inflammation associated cytokines showed that the sera of all Cpn10 variant pre-treated mice prior to LPS injection have reduced levels of TNF-α, IL-6 and IL-10 cytokines relative to sera of mice which received LPS alone. As expected, mice pre-treated with Ala-Cpn10 showed reduced levels of TNF-α and IL-6 cytokines, consistent with our previous results (Johnson et al, 2005). The current results suggest that Ala-Cpn10 may reduce IL-10 production in response to all TLR agonists. We next established a similar reduction in the levels of these inflammation associated cytokines in mice pre-treated with a number of Cpn10 variants (Table 7). Although, statistical analysis show the reduction of TNF-α and IL-6 cytokine levels is only significant with some of the Cpn10 variant pre-treatment relative to untreated group (FIGS. 15A&C, Table 7), the overall trend shows that all Cpn10 proteins used in this study appear to down modulate the LPS-inflammatory response.

The in vivo endotoxemia results reveal that all Cpn10 polypeptides studied (i.e. Ala-Cpn10, Ala-Cpn10-Δml, Ala-Cpn10-Δroof, and X-Cpn10) have similar activities to Ala-Cpn10. This reconfirms that the mobile loop or the roof loop regions of Cpn10 are not necessary for modulation of the response to TLR4-LPS ligation. The variations observed in the in vitro activities of X-Cpn10 could not be assessed in the endotoxaemia study as the mean cytokine levels between Cpn10 variant pre-treated groups are not statistically different.

Example 17

Purification of Cpn10 from *E. coli* Batch Fermentation

A bioprocess has been developed for the production of Cpn10 polypeptides. As demonstrated below, this process has successfully been used for the production of ~20 g of recombinant human Cpn10 from a 100 liter *E. coli* fermentation with >99% purity, ≤0.03 EU mg$^{-1}$ endotoxin and ≤155.3 pg mg$^{-1}$ DNA. The process is outlined below.

Fermentation

A vial containing the *E. coli* strain XL1-Blue harbouring the AlaCpn10_pPL550 plasmid was retrieved from the master cell bank (see "General Methods" above) and "pre-cultured" overnight in Soya Broth with no antibiotic supplementation at 30° C. An inoculum culture was subsequently prepared for the 100 L bioreactor maintaining the above media and growth temperature parameters. An aliquot of this inoculum was dispensed into a 100 L bioreactor in a soya-based peptone-enriched minimal media containing no animal-derived products (BresaGen, SA, Australia) and no antibiotic supplementation. The bioreactor cultivation did not require batch feeding and the temperature was maintained throughout the growth phase at 30±0.1° C. The pH was maintained at 7.0±0.2 by the addition of ammonia. Induction of Cpn10 was achieved by a temperature shift to 42° C. at an OD600 of 10 and further incubation at 42±0.1° C. for 3 h at which time the fermentation reached an OD600 of between 20-25.

Cell Lysis and Preparation of a Soluble Lysate

Bacterial cells (~3.5 kg wet weight) were pelleted by centrifugation (5,000×g), resuspended in 25 mM Tris-HCl (pH 8.0) and lysed by 3 passages through an APV Gaulin Model 30CD pressure homogeniser at 7000 psi (APV, USA) within three hours of the completion of fermentation. The soluble Cpn10 contained in the bacterial lysate was harvested after pelleting cell debris using a flow-through Westfalia MSB-7 centrifuge. Approximately 20 L of clarified lysate was stored overnight at 4° C.

Purification of Cpn10

A three-step downstream process was developed for the purification of Cpn10, incorporating Big Bead Sulfopropyl-Sepharose (BBSP) cation exchange, Q-Sepharose Fast Flow (QFF) anion exchange and High Performance Sepharose SP (HPSP) cation exchange chromatography. Chromatography was carried out using a K-prime 40-11 Bioprocess Unit (Millipore).

All ion-exchange chromatography columns were depyrogenated by washing with 1 M NaOH and equilibrated with buffer until eluates returned to the pH and conductivity of the specific buffers. All containers used for buffer storage and receipt of column eluates in the various purification steps were pyrogen-free. All buffers used in the purification were produced using Water For Injection (WFI).

Big Bead Sulfopropyl-Sepharose Chromatography

The lysate was loaded over 20-40 min onto a BBSP cation exchange column (BPG 300/500 with 8.6 L of BBSP SP-Sepharose resin, GE Biosciences) pre-equilibrated with 25 mM Tris-HCl, pH8.0 (Buffer A), at 75 cm hr$^{-1}$ linear flow-rate and a loading rate of up to 10 g Cpn10 per liter of resin. After washing with Buffer A, the captured Cpn10 was eluted with BufferA containing 150 mM NaCl and 1 L fractions were collected. SDS-PAGE analysis showed the BBSP pool to be >95% pure.

Q-Sepharose Fast Flow Chromatography

The BBSP eluate was desalted against two changes of 15 volumes of Buffer A at room temperature. The first dialysis step was performed for 2-3 hr, followed by transfer to a fresh BufferA tank where dialysis continued overnight. The redistribution of NaCl from the dialysis bags into the tank buffer was monitored by measuring dialysate conductivity (Cyberscan 100, Eutech Instruments, Singapore) against calibrated standards. The dialysed BBSP pool was loaded onto a BPG 200/500 column packed with 4.7 L of QFF anion exchange resin (GE Biosciences) pre-equilibrated in Buffer A at a linear flow-rate of 75 cm hr$^{-1}$ and a loading rate of up to 15 g Cpn10 per liter of resin. The QFF anion exchange flowthrough containing the Cpn10 was collected. Under the loading conditions, the majority of the E. coli cell proteins, nucleic acid and endotoxin remained bound to the matrix.

Sulfopropyl-Sepharose High Performance Chromatography

The QFF flowthrough was applied to a BPG 100/500 column packed with 1.67 L of SPHP resin (GE Biosciences), pre-equilibrated with 50 mM Tris-HCl pH 7.6 (Buffer B), at 15-20 g Cpn10 per liter of resin. The bound Cpn10 was eluted with a linear gradient from 0-120 mM NaCl over 15 L and 0.5 L fractions were collected. The fractions were pooled according to size exclusion chromatography (SEC), HPLC and SDS-PAGE analyses. The Cpn10 protein and NaCl ion concentrations were determined by UV Absorbance at 280 nm and the Ion Selective Electrode method (IDEXX, Australia), respectively.

Formulation

Based on Na$^+$ and Cl$^-$ ion measurements combined with conductivity measurements of the pooled SPHP fractions, the buffer was adjusted to a final formulation of 50 mM Tris-HCl pH 7.6 containing 150 mM NaCl. The formulated Cpn10 was filtered through a 0.2 μm filter under aseptic conditions. The filtered solution was dispensed into 500 ml pyrogen-free plastic bottles, with each bottle receiving 500 ml for a total of 2.5 g Cpn10 per bottle.

SDS-PAGE Analysis

SDS PAGE analyses on E. coli cell lysates and chromatography fractions was performed using NuPAGE 4-12% Bis-Tris gradient gels (Invitrogen, Carlsbad, Calif.) according to the manufacturer's protocol. Gels were Coomassie Brilliant Blue stained and each gel included Cpn10 protein and molecular weight standards.

Quantitation of Purified Cpn10 by Spectrophotometry

Purified Cpn10 concentrations were determined by UV absorbance (BioRad SmartSpec-3000 spectrophotometer) at 280 nm using an extinction coefficient of 0.353 mg$^{-1}$ mL$^{-1}$ cm$^{-1}$. It should be noted that the BioRad SmartSpec-3000 typically return an A280 nm value of 0.59 for bovine serum albumin (Pierce) while the literature value is 0.67 (Pierce technical resource No. TR0006.0).

Summary of Cpn10 purity and yields throughout the above described purification process are shown in Table 8. In (A) total protein concentrations were determined by the BCA protein assay (Sigma) and Cpn10 purity was determined by densitometry of cell lysate and Cpn10-containing fractions after each purification step. (B) Comparison of the final purity and yields from three Cpn10 purifications. Each purification was prepared from a 100 L E. coli batch fermentation. All preparations had a final Cpn10 purity of >99% by Coomassie stained SDS-PAGE. Endotoxin units (EU) are expressed as EU per mg of Cpn10 while DNA levels are expressed as pg per mg of Cpn10.

TABLE 8

| A. Cpn10 purity and yield after each purification step | | | | |
| --- | --- | --- | --- | --- |
| Purification Steps | Total Cpn10 Protein | Total Volume (L) | Cpn10 purity (%) | Step yield (%) |
| E. coil soluble lysate | 95 | 20.8 | | |
| Big Bead Sulfopropyl- | 28.8 | 6.2 | >98 | 30 |
| Q-Sepharose Fast | 26.1 | 8.6 | >99 | 91 |

TABLE 8-continued

| Sulfopropyl-Sepharose High Performance | 21.3 | 2.1 | >99 | 82 |

B. Cpn10 purity and yield from three purifications

| Batch No. | Cpn10 (g L$^{-1}$) | Total Cpn10 (g) | Endotoxin (EU mg$^{-1}$) | Host DNA (pg mg$^{-1}$) |
|---|---|---|---|---|
| 1 | 4.84 | 20.6 | 0.02 | <122.9 |
| 2 | 5.03 | 19.0 | <0.01 | <155.3 |
| 3 | 4.96 | 22.9 | 0.03 | <133.3 |

Example 18

Compositions

Molecules and agents of the present invention, and those identified by methods of the invention may be used for the treatment or prevention of various disease states and conditions. Such molecules and agents may be administered alone, although it is more typical that they be administered as a pharmaceutical composition.

In accordance with the best mode of performing the invention provided herein, specific preferred compositions are outlined below. The following are to be construed as merely illustrative examples of compositions and not as a limitation of the scope of the present invention in any way.

Example 18(a)

Composition for Parenteral Administration

A composition for intramuscular injection could be prepared to contain 1 mL sterile buffered water, and 1 mg of a suitable agent or molecule.

Similarly, a composition for intravenous infusion may comprise 250 ml of sterile Ringer's solution, and 5 mg of a suitable agent or molecule.

Example 18(b)

Injectable Parenteral Administration

A composition suitable for administration by injection may be prepared by mixing 1% by weight of a suitable agent or molecule in 10% by volume propylene glycol and water. The solution is sterilized by filtration.

Example 18(c)

Capsule Composition

A composition of a suitable agent or molecule in the form of a capsule may be prepared by filling a standard two-piece hard gelatin capsule with 50 mg of the agent or molecule, in powdered form, 100 mg of lactose, 35 mg of talc and 10 mg of magnesium stearate.

Example 18(d)

Eye Drop Composition

A typical composition for delivery as an eye drop is outlined below:

| Suitable agent or compound | 0.3 g |
| Methyl Hydroxybenzoate | 0.005 g |
| Propyl Hydroxybenzoate | 0.06 g |
| Purified Water about to | 100.00 ml. |

The methyl and propyl hydroxybenzoates are dissolved in 70 ml purified water at 75° C., and the resulting solution is allowed to cool. The suitable agent or molecule is then added, and the solution sterilized by filtration through a membrane filter (0.22 μm pore size), and aseptically packed into sterile containers.

Example 18(e)

Composition for Inhalation Administration

For an aerosol container with a capacity of 20-30 ml: a mixture of 10 mg of a suitable agent or compound with 0.5-0.8% by weight of a lubricating agent, such as polysorbate 85 or oleic acid, is dispersed in a propellant, such as freon, and put into an appropriate aerosol container for either intranasal or oral inhalation administration.

Example 18(f)

Ointment Composition

A typical composition for delivery as an ointment includes 1.0 g of a suitable agent or molecule, together with white soft paraffin to 100.0 g, dispersed to produce a smooth, homogeneous product.

Example 18(g)

Topical Cream Composition

A typical composition for delivery as a topical cream is outlined below:

| Suitable agent or molecule | 1.0 g |
| Polawax GP 200 | 25.0 g |
| Lanolin Anhydrous | 3.0 g |
| White Beeswax | 4.5 g |
| Methyl hydroxybenzoate | 0.1 g |
| Deionized & sterilized Water to | 100.0 g |

The polawax, beeswax and lanolin are heated together at 60° C., a solution of methyl hydroxybenzoate is added and homogenization achieved using high speed stirring. The temperature is then allowed to fall to 50° C. The agent or molecule is then added and dispersed throughout, and the composition is allowed to cool with slow speed stirring.

Example 18(h)

Topical Lotion Composition

A typical composition for delivery as a topical lotion is outlined below:

| Suitable agent or molecule | 1.2 g |
|---|---|
| Sorbitan Monolaurate | 0.8 g |
| Polysorbate 20 | 0.7 g |
| Cetostearyl Alcohol | 1.5 g |
| Glycerin | 7.0 g |
| Methyl Hydroxybenzoate | 0.4 g |
| Sterilized Water about to | 100.00 ml |

The methyl hydroxybenzoate and glycerin are dissolved in 70 ml of the water at 75° C. The sorbitan monolaurate, polysorbate 20 and cetostearyl alcohol are melted together at 75° C. and added to the aqueous solution. The resulting emulsion is homogenized, allowed to cool with continuous stirring and the agent or molecule is added as a suspension in the remaining water. The whole suspension is stirred until homogenized.

What is claimed is:

1. An isolated Cpn10 polypeptide, wherein the first five amino-terminal amino acids arc Gly-Ala-Gly-Gln-Ala (SEQ ID NO: 47).

2. The isolated Cpn10 polypeptide of claim 1 wherein the polypeptide comprises the amino acid sequence of SEQ ID NO: 30.

3. The polypeptide of claim 1 or 2 displaying immunomodulatory activity at least as great as the level of immunomodulatory activity of the corresponding wild-type Cpn10 polypeptide.

4. A pharmaceutical composition comprising the isolated polypeptide of claim 1.

5. The pharmaceutical composition of claim 4 comprising one or more additional agents.

* * * * *

```
                         SEQUENCE LISTING

<160> NUMBER OF SEQ ID NOS: 47

<210> SEQ ID NO 1
<211> LENGTH: 102
<212> TYPE: PRT
<213> ORGANISM: Homo sapiens
<220> FEATURE:
<223> OTHER INFORMATION: human Cpn10 (wild-type), including initiating
      Met, not including N-terminal acetyl group

<400> SEQUENCE: 1

Met Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 2
<211> LENGTH: 309
<212> TYPE: DNA
<213> ORGANISM: Homo sapiens
<220> FEATURE:
<223> OTHER INFORMATION: human Cpn10 (wild-type), including initiating
      Met
<220> FEATURE:
<221> NAME/KEY: CDS
<222> LOCATION: (1)..(306)
<223> OTHER INFORMATION: Cpn10

<400> SEQUENCE: 2 atg gca gga caa gcg ttt aga aag ttt ctt cca ctc ttt gac cga gta       48
Met Ala Gly Gln Ala Phe Arg Lys Phe Leu Pro Leu Phe Asp Arg Val
1               5                   10                  15 ttg gtt gaa agg agt gct gct gaa act gta acc aaa gga ggc att atg       96
Leu Val Glu Arg Ser Ala Ala Glu Thr Val Thr Lys Gly Gly Ile Met
            20                  25                  30 ctt cca gaa aaa tct caa gga aaa gta ttg caa gca aca gta gtc gct      144
Leu Pro Glu Lys Ser Gln Gly Lys Val Leu Gln Ala Thr Val Val Ala
        35                  40                  45
```

```
gtt gga tcg ggt tct aaa gga aag ggt gga gag att caa cca gtt agc       192
Val Gly Ser Gly Ser Lys Gly Lys Gly Gly Glu Ile Gln Pro Val Ser
 50                  55                  60 gtg aaa gtt gga gat aaa gtt ctt ctc cca gaa tat gga ggc acc aaa       240
Val Lys Val Gly Asp Lys Val Leu Leu Pro Glu Tyr Gly Gly Thr Lys
 65                  70                  75                  80 gta gtt cta gat gac aag gat tat ttc cta ttt aga gat ggt gac att       288
Val Val Leu Asp Asp Lys Asp Tyr Phe Leu Phe Arg Asp Gly Asp Ile
                 85                  90                  95 ctt gga aag tac gta gac tga                                           309
Leu Gly Lys Tyr Val Asp
            100

<210> SEQ ID NO 3
<211> LENGTH: 86
<212> TYPE: PRT
<213> ORGANISM: Artificial Sequence
<220> FEATURE:
<223> OTHER INFORMATION: Description of Artificial Sequence: Synthetic
      Cpn10-deltaml, including initiating Met, mobile loop deleted

<400> SEQUENCE: 3

Met Ala Gly Gln Ala Phe Arg Lys Phe Leu Pro Leu Phe Asp Arg Val
 1               5                  10                  15

Leu Val Glu Arg Ser Ala Gly Lys Val Leu Gln Ala Thr Val Val Ala
             20                  25                  30

Val Gly Ser Gly Ser Lys Gly Lys Gly Gly Glu Ile Gln Pro Val Ser
         35                  40                  45

Val Lys Val Gly Asp Lys Val Leu Leu Pro Glu Tyr Gly Gly Thr Lys
 50                  55                  60

Val Val Leu Asp Asp Lys Asp Tyr Phe Leu Phe Arg Asp Gly Asp Ile
 65                  70                  75                  80

Leu Gly Lys Tyr Val Asp
             85

<210> SEQ ID NO 4
<211> LENGTH: 261
<212> TYPE: DNA
<213> ORGANISM: Artificial Sequence
<220> FEATURE:
<223> OTHER INFORMATION: Description of Artificial Sequence: synthetic
      Cpn10-deltaml, including initiating Met, mobile loop deleted
<220> FEATURE:
<221> NAME/KEY: CDS
<222> LOCATION: (1)..(258)
<223> OTHER INFORMATION: Cpn10-deltaml

<400> SEQUENCE: 4 atg gca gga caa gcg ttt aga aag ttt ctt cca ctc ttt gac cga gta        48
Met Ala Gly Gln Ala Phe Arg Lys Phe Leu Pro Leu Phe Asp Arg Val
 1               5                  10                  15 ttg gtt gaa agg agt gct gga aaa gta ttg caa gca aca gta gtc gct        96
Leu Val Glu Arg Ser Ala Gly Lys Val Leu Gln Ala Thr Val Val Ala
             20                  25                  30 gtt gga tcg ggt tct aaa gga aag ggt gga gag att caa cca gtt agc       144
Val Gly Ser Gly Ser Lys Gly Lys Gly Gly Glu Ile Gln Pro Val Ser
         35                  40                  45 gtg aaa gtt gga gat aaa gtt ctt ctc cca gaa tat gga ggc acc aaa       192
Val Lys Val Gly Asp Lys Val Leu Leu Pro Glu Tyr Gly Gly Thr Lys
 50                  55                  60 gta gtt cta gat gac aag gat tat ttc cta ttt aga gat ggt gac att       240
Val Val Leu Asp Asp Lys Asp Tyr Phe Leu Phe Arg Asp Gly Asp Ile
```

```
                65                  70                  75                  80
ctt gga aag tac gta gac tga                                                        261
Leu Gly Lys Tyr Val Asp
                85

<210> SEQ ID NO 5
<211> LENGTH: 264
<212> TYPE: DNA
<213> ORGANISM: Artificial Sequence
<220> FEATURE:
<223> OTHER INFORMATION: Description of Artificial Sequence: Synthetic
      Cpn10-deltaml, including initiating Met, mobile loop deleted, with
      extra Ala at position 2
<220> FEATURE:
<221> NAME/KEY: CDS
<222> LOCATION: (1)..(261)
<223> OTHER INFORMATION: Cpn10-deltaml

<400> SEQUENCE: 5 atg gcg gcg ggt cag gcg ttt cgt aaa ttt ctg ccg ctg ttt gat cgt        48
Met Ala Ala Gly Gln Ala Phe Arg Lys Phe Leu Pro Leu Phe Asp Arg
1               5                   10                  15 gtt ctg gtt gaa cgt agc gcg ggc aaa gtt ctg cag gcg acc gtt gtt        96
Val Leu Val Glu Arg Ser Ala Gly Lys Val Leu Gln Ala Thr Val Val
                20                  25                  30 gcg gtt ggt agc ggc agc aaa ggt aaa ggc ggt gaa att cag ccg gtt       144
Ala Val Gly Ser Gly Ser Lys Gly Lys Gly Gly Glu Ile Gln Pro Val
            35                  40                  45 agc gtg aaa gtg ggc gat aaa gtt ctg ctg ccg gaa tat ggc ggc acc       192
Ser Val Lys Val Gly Asp Lys Val Leu Leu Pro Glu Tyr Gly Gly Thr
        50                  55                  60 aaa gtt gtg ctg gat gat aaa gat tac ttc ctg ttc cgc gat ggt gat       240
Lys Val Val Leu Asp Asp Lys Asp Tyr Phe Leu Phe Arg Asp Gly Asp
65                  70                  75                  80 atc ctg ggc aaa tac gtg gat taa                                       264
Ile Leu Gly Lys Tyr Val Asp
                85

<210> SEQ ID NO 6
<211> LENGTH: 95
<212> TYPE: PRT
<213> ORGANISM: Artificial Sequence
<220> FEATURE:
<223> OTHER INFORMATION: Description of Artificial Sequence: Synthetic
      Cpn10-deltaroof, including initiating Met, roof loop deleted

<400> SEQUENCE: 6

Met Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
                20                  25                  30

Leu Pro Glu Lys Ser Gln Gly Lys Val Leu Gln Ala Thr Val Val Ala
            35                  40                  45

Val Gly Ser Gly Ser Gln Pro Val Ser Val Lys Val Gly Asp Lys Val
        50                  55                  60

Leu Leu Pro Glu Tyr Gly Gly Thr Lys Val Val Leu Asp Asp Lys Asp
65                  70                  75                  80

Tyr Phe Leu Phe Arg Asp Gly Asp Ile Leu Gly Lys Tyr Val Asp
                85                  90                  95

<210> SEQ ID NO 7
<211> LENGTH: 288
<212> TYPE: DNA
```

<213> ORGANISM: Artificial Sequence
<220> FEATURE:
<223> OTHER INFORMATION: Description of Artificial Sequence: Synthetic Cpn10-deltaroof, including initiating Met, roof loop deleted
<220> FEATURE:
<221> NAME/KEY: CDS
<222> LOCATION: (1)..(285)
<223> OTHER INFORMATION: Cpn10-deltaml

<400> SEQUENCE: 7

```
atg gca gga caa gcg ttt aga aag ttt ctt cca ctc ttt gac cga gta      48
Met Ala Gly Gln Ala Phe Arg Lys Phe Leu Pro Leu Phe Asp Arg Val
1               5                   10                  15 ttg gtt gaa agg agt gct gct gaa act gta acc aaa gga ggc att atg      96
Leu Val Glu Arg Ser Ala Ala Glu Thr Val Thr Lys Gly Gly Ile Met
            20                  25                  30 ctt cca gaa aaa tct caa gga aaa gta ttg caa gca aca gta gtc gct    144
Leu Pro Glu Lys Ser Gln Gly Lys Val Leu Gln Ala Thr Val Val Ala
        35                  40                  45 gtt gga tcg ggt tct caa cca gtt agc gtg aaa gtt gga gat aaa gtt    192
Val Gly Ser Gly Ser Gln Pro Val Ser Val Lys Val Gly Asp Lys Val
    50                  55                  60 ctt ctc cca gaa tat gga ggc acc aaa gta gtt cta gat gac aag gat    240
Leu Leu Pro Glu Tyr Gly Gly Thr Lys Val Val Leu Asp Asp Lys Asp
65                  70                  75                  80 tat ttc cta ttt aga gat ggt gac att ctt gga aag tac gta gac tga    288
Tyr Phe Leu Phe Arg Asp Gly Asp Ile Leu Gly Lys Tyr Val Asp
                85                  90                  95
```

<210> SEQ ID NO 8
<211> LENGTH: 291
<212> TYPE: DNA
<213> ORGANISM: Artificial Sequence
<220> FEATURE:
<223> OTHER INFORMATION: Description of Artificial Sequence: Synthetic Cpn10-deltaroof, including initiating Met, roof loop deleted, with extra Ala at position 2
<220> FEATURE:
<221> NAME/KEY: CDS
<222> LOCATION: (1)..(285)
<223> OTHER INFORMATION: Cpn10-deltaml

<400> SEQUENCE: 8

```
atg gcg gcg ggt cag gcg ttt cgt aaa ttt ctg ccg ctg ttt gat cgt      48
Met Ala Ala Gly Gln Ala Phe Arg Lys Phe Leu Pro Leu Phe Asp Arg
1               5                   10                  15 gtt ctg gtt gaa cgt agc gcg gcg gaa acc gtt acc aaa ggc ggt att      96
Val Leu Val Glu Arg Ser Ala Ala Glu Thr Val Thr Lys Gly Gly Ile
            20                  25                  30 atg ctg ccg gaa aaa agc cag ggt aaa gtt ctg cag gcg acc gtt gtt    144
Met Leu Pro Glu Lys Ser Gln Gly Lys Val Leu Gln Ala Thr Val Val
        35                  40                  45 gcg gtt ggt agc ggt agc cag ccg gtt agc gtg aaa gtg ggc gat aaa    192
Ala Val Gly Ser Gly Ser Gln Pro Val Ser Val Lys Val Gly Asp Lys
    50                  55                  60 gtt ctg ctg ccg gaa tat ggc ggc acc aaa gtt gtg ctg gat gat aaa    240
Val Leu Leu Pro Glu Tyr Gly Gly Thr Lys Val Val Leu Asp Asp Lys
65                  70                  75                  80 gat tac ttc ctg ttc cgc gat ggt gat atc ctg ggc aaa tac gtg           285
Asp Tyr Phe Leu Phe Arg Asp Gly Asp Ile Leu Gly Lys Tyr Val
                85                  90                  95 gattaa                                                              291
```

<210> SEQ ID NO 9

```
<211> LENGTH: 79
<212> TYPE: PRT
<213> ORGANISM: Artificial Sequence
<220> FEATURE:
<223> OTHER INFORMATION: Description of Artificial Sequence: Synthetic
      Cpn10 beta-barrel, including initiating Met, roof loop and mobile
      loop deleted

<400> SEQUENCE: 9

Met Ala Gly Gln Ala Phe Arg Lys Phe Leu Pro Leu Phe Asp Arg Val
1               5                   10                  15

Leu Val Glu Arg Ser Ala Gly Lys Val Leu Gln Ala Thr Val Val Ala
            20                  25                  30

Val Gly Ser Gly Ser Gln Pro Val Ser Val Lys Val Gly Asp Lys Val
        35                  40                  45

Leu Leu Pro Glu Tyr Gly Gly Thr Lys Val Val Leu Asp Asp Lys Asp
    50                  55                  60

Tyr Phe Leu Phe Arg Asp Gly Asp Ile Leu Gly Lys Tyr Val Asp
65                  70                  75

<210> SEQ ID NO 10
<211> LENGTH: 240
<212> TYPE: DNA
<213> ORGANISM: Artificial Sequence
<220> FEATURE:
<223> OTHER INFORMATION: Description of Artificial Sequence: Synthetic
      Cpn10 beta-barrel, including initiating Met, roof loop and mobile
      loop deleted
<220> FEATURE:
<221> NAME/KEY: CDS
<222> LOCATION: (1)..(237)
<223> OTHER INFORMATION: Cpn10 beta-barrel

<400> SEQUENCE: 10 atg gca gga caa gcg ttt aga aag ttt ctt cca ctc ttt gac cga gta      48
Met Ala Gly Gln Ala Phe Arg Lys Phe Leu Pro Leu Phe Asp Arg Val
1               5                   10                  15 ttg gtt gaa agg agt gct gga aaa gta ttg caa gca aca gta gtc gct      96
Leu Val Glu Arg Ser Ala Gly Lys Val Leu Gln Ala Thr Val Val Ala
            20                  25                  30 gtt gga tcg ggt tct caa cca gtt agc gtg aaa gtt gga gat aaa gtt     144
Val Gly Ser Gly Ser Gln Pro Val Ser Val Lys Val Gly Asp Lys Val
        35                  40                  45 ctt ctc cca gaa tat gga ggc acc aaa gta gtt cta gat gac aag gat     192
Leu Leu Pro Glu Tyr Gly Gly Thr Lys Val Val Leu Asp Asp Lys Asp
    50                  55                  60 tat ttc cta ttt aga gat ggt gac att ctt gga aag tac gta gac tga     240
Tyr Phe Leu Phe Arg Asp Gly Asp Ile Leu Gly Lys Tyr Val Asp
65                  70                  75

<210> SEQ ID NO 11
<211> LENGTH: 97
<212> TYPE: PRT
<213> ORGANISM: Escherichia coli
<220> FEATURE:
<223> OTHER INFORMATION: Bacterial homolog of Cpn10 (GroES)

<400> SEQUENCE: 11

Met Asn Ile Arg Pro Leu His Asp Arg Val Ile Val Lys Arg Lys Glu
1               5                   10                  15

Val Glu Thr Lys Ser Ala Gly Gly Ile Val Leu Thr Gly Ser Ala Ala
            20                  25                  30

Ala Lys Ser Thr Arg Gly Glu Val Leu Ala Val Gly Asn Gly Arg Ile
        35                  40                  45
```

```
Leu Glu Asn Gly Glu Val Lys Pro Leu Asp Val Lys Val Gly Asp Ile
 50                  55                  60

Val Ile Phe Asn Asp Gly Tyr Gly Val Lys Ser Glu Lys Ile Asp Asn
 65                  70                  75                  80

Glu Glu Val Leu Ile Met Ser Glu Ser Asp Ile Leu Ala Ile Val Glu
                 85                  90                  95

Ala

<210> SEQ ID NO 12
<211> LENGTH: 16
<212> TYPE: PRT
<213> ORGANISM: Artificial Sequence
<220> FEATURE:
<223> OTHER INFORMATION: Description of Artificial Sequence: Synthetic
      Cpn10 mobile loop

<400> SEQUENCE: 12

Ala Glu Thr Val Thr Lys Gly Gly Ile Met Leu Pro Glu Lys Ser Gln
 1               5                  10                  15

<210> SEQ ID NO 13
<211> LENGTH: 7
<212> TYPE: PRT
<213> ORGANISM: Artificial Sequence
<220> FEATURE:
<223> OTHER INFORMATION: Description of Artificial Sequence: Synthetic
      Cpn10 beta hairpin roof loop

<400> SEQUENCE: 13

Lys Gly Lys Gly Gly Glu Ile
 1               5

<210> SEQ ID NO 14
<211> LENGTH: 96
<212> TYPE: PRT
<213> ORGANISM: Artificial Sequence
<220> FEATURE:
<223> OTHER INFORMATION: Description of Artificial Sequence: Synthetic
      Cpn10-NtermES, including initiating Met, including E. coli
      bacterial homolog of Cpn10 (GroES) N-terminus

<400> SEQUENCE: 14

Met Asn Ile Arg Pro Leu Phe Asp Arg Val Leu Val Glu Arg Ser Ala
 1               5                  10                  15

Ala Glu Thr Val Thr Lys Gly Gly Ile Met Leu Pro Glu Lys Ser Gln
                 20                  25                  30

Gly Lys Val Leu Gln Ala Thr Val Val Ala Val Gly Ser Gly Ser Lys
             35                  40                  45

Gly Lys Gly Gly Glu Ile Gln Pro Val Ser Val Lys Val Gly Asp Lys
         50                  55                  60

Val Leu Leu Pro Glu Tyr Gly Gly Thr Lys Val Val Leu Asp Asp Lys
 65                  70                  75                  80

Asp Tyr Phe Leu Phe Arg Asp Gly Asp Ile Leu Gly Lys Tyr Val Asp
                 85                  90                  95

<210> SEQ ID NO 15
<211> LENGTH: 43
<212> TYPE: DNA
<213> ORGANISM: Artificial Sequence
<220> FEATURE:
<223> OTHER INFORMATION: Description of Artificial Sequence: Synthetic
      forward primer for EEE tripeptide in mobile loop
```

<400> SEQUENCE: 15
ctgtaaccaa aggaggcgaa gaggaaccag aaaaatctca agg         43

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: Synthetic
      reverse primer for EEE tripeptide in mobile loop

<400> SEQUENCE: 16
ccttgagatt tttctggttc ctcttcgcct cctttggtta cag         43

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Synthetic
      forward primer for IFI tripeptide in mobile loop

<400> SEQUENCE: 17
ccaaaggagg cattttcatt ccagaaaaat ctc         33

<210> SEQ ID NO 18
<211> LENGTH: 33
<212> TYPE: DNA
<213> ORGANISM: Artificial Sequence
<220> FEATURE:
<223> OTHER INFORMATION: Description of Artificial Sequence: Synthetic
      reverse primer for IFI tripeptide in mobile loop

<400> SEQUENCE: 18 gagattttc tggaatgaaa atgcctcctt tgg         33

<210> SEQ ID NO 19
<211> LENGTH: 43
<212> TYPE: DNA
<213> ORGANISM: Artificial Sequence
<220> FEATURE:
<223> OTHER INFORMATION: Description of Artificial Sequence: Synthetic
      forward primer for III tripeptide in mobile loop

<400> SEQUENCE: 19
ctgtaaccaa aggaggcatt ataattccag aaaaatctca agg         43

<210> SEQ ID NO 20
<211> LENGTH: 43
<212> TYPE: DNA
<213> ORGANISM: Artificial Sequence
<220> FEATURE:
<223> OTHER INFORMATION: Description of Artificial Sequence: Synthetic
      reverse primer for III tripeptide in mobile loop

<400> SEQUENCE: 20
ccttgagatt tttctggaat tataatgcct cctttggtta cag         43

<210> SEQ ID NO 21
<211> LENGTH: 102
<212> TYPE: PRT
<213> ORGANISM: Artificial Sequence
<220> FEATURE:
<223> OTHER INFORMATION: Description of Artificial Sequence: Synthetic
      Ala-Cpn10 (wild-type), extra N-terminal Ala residue, not including
      N-terminal acetyl group

<400> SEQUENCE: 21

```
Ala Ala Gly Gln Ala Phe Arg Lys Phe Leu Pro Leu Phe Asp Arg Val
1               5                   10                  15
Leu Val Glu Arg Ser Ala Ala Glu Thr Val Thr Lys Gly Gly Ile Met
            20                  25                  30
Leu Pro Glu Lys Ser Gln Gly Lys Val Leu Gln Ala Thr Val Val Ala
        35                  40                  45
Val Gly Ser Gly Ser Lys Gly Lys Gly Gly Glu Ile Gln Pro Val Ser
    50                  55                  60
Val Lys Val Gly Asp Lys Val Leu Leu Pro Glu Tyr Gly Gly Thr Lys
65                  70                  75                  80
Val Val Leu Asp Asp Lys Asp Tyr Phe Leu Phe Arg Asp Gly Asp Ile
                85                  90                  95
Leu Gly Lys Tyr Val Asp
            100
```

<210> SEQ ID NO 22
<211> LENGTH: 312
<212> TYPE: DNA
<213> ORGANISM: Artificial Sequence
<220> FEATURE:
<223> OTHER INFORMATION: Description of Artificial Sequence: Synthetic Ala-Cpn10 (wild-type), extra N-terminal Ala residue
<220> FEATURE:
<221> NAME/KEY: CDS
<222> LOCATION: (1)..(309)
<223> OTHER INFORMATION: Ala-Cpn10

<400> SEQUENCE: 22

```
atg gca gca gga caa gcg ttt aga aag ttt ctt cca ctc ttt gac cga    48
Met Ala Ala Gly Gln Ala Phe Arg Lys Phe Leu Pro Leu Phe Asp Arg
1               5                   10                  15 gta ttg gtt gaa agg agt gct gct gaa act gta acc aaa gga ggc att    96
Val Leu Val Glu Arg Ser Ala Ala Glu Thr Val Thr Lys Gly Gly Ile
            20                  25                  30 atg ctt cca gaa aaa tct caa gga aaa gta ttg caa gca aca gta gtc   144
Met Leu Pro Glu Lys Ser Gln Gly Lys Val Leu Gln Ala Thr Val Val
        35                  40                  45 gct gtt gga tcg ggt tct aaa gga aag ggt gga gag att caa cca gtt   192
Ala Val Gly Ser Gly Ser Lys Gly Lys Gly Gly Glu Ile Gln Pro Val
    50                  55                  60 agc gtg aaa gtt gga gat aaa gtt ctt ctc cca gaa tat gga ggc acc   240
Ser Val Lys Val Gly Asp Lys Val Leu Leu Pro Glu Tyr Gly Gly Thr
65                  70                  75                  80 aaa gta gtt cta gat gac aag gat tat ttc cta ttt aga gat ggt gac   288
Lys Val Val Leu Asp Asp Lys Asp Tyr Phe Leu Phe Arg Asp Gly Asp
                85                  90                  95 att ctt gga aag tac gta gac tga                                    312
Ile Leu Gly Lys Tyr Val Asp
            100
```

<210> SEQ ID NO 23
<211> LENGTH: 101
<212> TYPE: PRT
<213> ORGANISM: Homo sapiens
<220> FEATURE:
<223> OTHER INFORMATION: Human X-Cpn10 (wild-type), not including N-terminal acetyl group

<400> SEQUENCE: 23

```
Ala Gly Gln Ala Phe Arg Lys Phe Leu Pro Leu Phe Asp Arg Val Leu
1               5                   10                  15
```

```
Val Glu Arg Ser Ala Ala Glu Thr Val Thr Lys Gly Gly Ile Met Leu
         20                  25                  30

Pro Glu Lys Ser Gln Gly Lys Val Leu Gln Ala Thr Val Val Ala Val
             35                  40                  45

Gly Ser Gly Ser Lys Gly Lys Gly Gly Glu Ile Gln Pro Val Ser Val
 50                  55                  60

Lys Val Gly Asp Lys Val Leu Leu Pro Glu Tyr Gly Gly Thr Lys Val
 65                  70                  75                  80

Val Leu Asp Asp Lys Asp Tyr Phe Leu Phe Arg Asp Gly Asp Ile Leu
                 85                  90                  95

Gly Lys Tyr Val Asp
            100

<210> SEQ ID NO 24
<211> LENGTH: 86
<212> TYPE: PRT
<213> ORGANISM: Artificial Sequence
<220> FEATURE:
<223> OTHER INFORMATION: Description of Artificial Sequence: Synthetic
      Ala-Cpn10-deltaml, extra N-terminal Ala residue, mobile
      loop deleted

<400> SEQUENCE: 24

Ala Ala Gly Gln Ala Phe Arg Lys Phe Leu Pro Leu Phe Asp Arg Val
 1               5                  10                  15

Leu Val Glu Arg Ser Ala Gly Lys Val Leu Gln Ala Thr Val Val Ala
             20                  25                  30

Val Gly Ser Gly Ser Lys Gly Lys Gly Gly Glu Ile Gln Pro Val Ser
             35                  40                  45

Val Lys Val Gly Asp Lys Val Leu Leu Pro Glu Tyr Gly Gly Thr Lys
 50                  55                  60

Val Val Leu Asp Asp Lys Asp Tyr Phe Leu Phe Arg Asp Gly Asp Ile
 65                  70                  75                  80

Leu Gly Lys Tyr Val Asp
                 85

<210> SEQ ID NO 25
<211> LENGTH: 264
<212> TYPE: DNA
<213> ORGANISM: Artificial Sequence
<220> FEATURE:
<223> OTHER INFORMATION: Description of Artificial Sequence: Synthetic
      Ala-Cpn10-deltaml, extra N-terminal Ala residue, mobile
      loop deleted
<220> FEATURE:
<221> NAME/KEY: CDS
<222> LOCATION: (1)..(261)
<223> OTHER INFORMATION: Ala-Cpn10-deltaml

<400> SEQUENCE: 25 atg gcg gcg ggt cag gcg ttt cgt aaa ttt ctg ccg ctg ttt gat cgt      48
Met Ala Ala Gly Gln Ala Phe Arg Lys Phe Leu Pro Leu Phe Asp Arg
 1               5                  10                  15 gtt ctg gtt gaa cgt agc gcg ggc aaa gtt ctg cag gcg acc gtt gtt      96
Val Leu Val Glu Arg Ser Ala Gly Lys Val Leu Gln Ala Thr Val Val
             20                  25                  30 gcg gtt ggt agc ggc agc aaa ggt aaa ggc ggt gaa att cag ccg gtt     144
Ala Val Gly Ser Gly Ser Lys Gly Lys Gly Gly Glu Ile Gln Pro Val
             35                  40                  45 agc gtg aaa gtg ggc gat aaa gtt ctg ctg ccg gaa tat ggc ggc acc     192
Ser Val Lys Val Gly Asp Lys Val Leu Leu Pro Glu Tyr Gly Gly Thr
```

```
aaa gtt gtg ctg gat gat aaa gat tac ttc ctg ttc cgc gat ggt gat      240
Lys Val Val Leu Asp Asp Lys Asp Tyr Phe Leu Phe Arg Asp Gly Asp
 65                  70                  75                  80 atc ctg ggc aaa tac gtg gat taa                                      264
Ile Leu Gly Lys Tyr Val Asp
                85
```

<210> SEQ ID NO 26
<211> LENGTH: 95
<212> TYPE: PRT
<213> ORGANISM: Artificial Sequence
<220> FEATURE:
<223> OTHER INFORMATION: Description of Artificial Sequence: Synthetic
      Ala-Cpn10-deltaroof, extra N-terminal Ala residue, roof
      loop deleted

<400> SEQUENCE: 26

```
Ala Ala Gly Gln Ala Phe Arg Lys Phe Leu Pro Leu Phe Asp Arg Val
 1               5                  10                  15

Leu Val Glu Arg Ser Ala Ala Glu Thr Val Thr Lys Gly Gly Ile Met
             20                  25                  30

Leu Pro Glu Lys Ser Gln Gly Lys Val Leu Gln Ala Thr Val Val Ala
         35                  40                  45

Val Gly Ser Gly Ser Gln Pro Val Ser Val Lys Val Gly Asp Lys Val
     50                  55                  60

Leu Leu Pro Glu Tyr Gly Gly Thr Lys Val Val Leu Asp Asp Lys Asp
 65                  70                  75                  80

Tyr Phe Leu Phe Arg Asp Gly Asp Ile Leu Gly Lys Tyr Val Asp
                 85                  90                  95
```

<210> SEQ ID NO 27
<211> LENGTH: 291
<212> TYPE: DNA
<213> ORGANISM: Artificial Sequence
<220> FEATURE:
<223> OTHER INFORMATION: Description of Artificial Sequence: Synthetic
      Ala-Cpn10-deltaroof, extra N-terminal Ala residue, roof
      loop deleted
<220> FEATURE:
<221> NAME/KEY: CDS
<222> LOCATION: (1)..(288)
<223> OTHER INFORMATION: Ala-Cpn10-deltaml

<400> SEQUENCE: 27

```
atg gcg gcg ggt cag gcg ttt cgt aaa ttt ctg ccg ctg ttt gat cgt      48
Met Ala Ala Gly Gln Ala Phe Arg Lys Phe Leu Pro Leu Phe Asp Arg
 1               5                  10                  15 gtt ctg gtt gaa cgt agc gcg gcg gaa acc gtt acc aaa ggc ggt att      96
Val Leu Val Glu Arg Ser Ala Ala Glu Thr Val Thr Lys Gly Gly Ile
             20                  25                  30 atg ctg ccg gaa aaa agc cag ggt aaa gtt ctg cag gcg acc gtt gtt     144
Met Leu Pro Glu Lys Ser Gln Gly Lys Val Leu Gln Ala Thr Val Val
         35                  40                  45 gcg gtt ggt agc ggt agc cag ccg gtt agc gtg aaa gtg ggc gat aaa     192
Ala Val Gly Ser Gly Ser Gln Pro Val Ser Val Lys Val Gly Asp Lys
     50                  55                  60 gtt ctg ctg ccg gaa tat ggc ggc acc aaa gtt gtg ctg gat gat aaa     240
Val Leu Leu Pro Glu Tyr Gly Gly Thr Lys Val Val Leu Asp Asp Lys
 65                  70                  75                  80 gat tac ttc ctg ttc cgc gat ggt gat atc ctg ggc aaa tac gtg gat     288
Asp Tyr Phe Leu Phe Arg Asp Gly Asp Ile Leu Gly Lys Tyr Val Asp
                 85                  90                  95
```

-continued

```
taa                                                                    291
```

<210> SEQ ID NO 28
<211> LENGTH: 79
<212> TYPE: PRT
<213> ORGANISM: Artificial Sequence
<220> FEATURE:
<223> OTHER INFORMATION: Description of Artificial Sequence: Synthetic
      Ala-Cpn10 beta-barrel, extra N-terminal Ala residue,
      roof loop and mobile loop deleted

<400> SEQUENCE: 28

```
Ala Ala Gly Gln Ala Phe Arg Lys Phe Leu Pro Leu Phe Asp Arg Val
1               5                   10                  15

Leu Val Glu Arg Ser Ala Gly Lys Val Leu Gln Ala Thr Val Val Ala
            20                  25                  30

Val Gly Ser Gly Ser Gln Pro Val Ser Val Lys Val Gly Asp Lys Val
        35                  40                  45

Leu Leu Pro Glu Tyr Gly Gly Thr Lys Val Val Leu Asp Asp Lys Asp
    50                  55                  60

Tyr Phe Leu Phe Arg Asp Gly Asp Ile Leu Gly Lys Tyr Val Asp
65                  70                  75
```

<210> SEQ ID NO 29
<211> LENGTH: 243
<212> TYPE: DNA
<213> ORGANISM: Artificial Sequence
<220> FEATURE:
<223> OTHER INFORMATION: Description of Artificial Sequence: Synthetic
      Ala-Cpn10 beta-barrel, extra N-terminal Ala residue,
      roof loop and mobile loop deleted
<220> FEATURE:
<221> NAME/KEY: CDS
<222> LOCATION: (1)..(240)
<223> OTHER INFORMATION: Ala-Cpn10 beta-barrel

<400> SEQUENCE: 29

```
atg gca gca gga caa gcg ttt aga aag ttt ctt cca ctc ttt gac cga        48
Met Ala Ala Gly Gln Ala Phe Arg Lys Phe Leu Pro Leu Phe Asp Arg
1               5                   10                  15 gta ttg gtt gaa agg agt gct gga aaa gta ttg caa gca aca gta gtc        96
Val Leu Val Glu Arg Ser Ala Gly Lys Val Leu Gln Ala Thr Val Val
            20                  25                  30 gct gtt gga tcg ggt tct caa cca gtt agc gtg aaa gtt gga gat aaa       144
Ala Val Gly Ser Gly Ser Gln Pro Val Ser Val Lys Val Gly Asp Lys
        35                  40                  45 gtt ctt ctc cca gaa tat gga ggc acc aaa gta gtt cta gat gac aag       192
Val Leu Leu Pro Glu Tyr Gly Gly Thr Lys Val Val Leu Asp Asp Lys
    50                  55                  60 gat tat ttc cta ttt aga gat ggt gac att ctt gga aag tac gta gac       240
Asp Tyr Phe Leu Phe Arg Asp Gly Asp Ile Leu Gly Lys Tyr Val Asp
65                  70                  75                  80 tga                                                                   243
```

<210> SEQ ID NO 30
<211> LENGTH: 102
<212> TYPE: PRT
<213> ORGANISM: Artificial Sequence
<220> FEATURE:
<223> OTHER INFORMATION: Description of Artificial Sequence: Synthetic
      Gly-Cpn10, extra N-terminal Gly residue, not including N-terminal
      acetyl group

<400> SEQUENCE: 30

```
Gly Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Met
            20                  25                  30

Leu Pro Glu Lys Ser Gln Gly Lys Val Leu Gln Ala Thr Val Val Ala
            35                  40                  45

Val Gly Ser Gly Ser Lys Gly Lys Gly Gly Glu Ile Gln Pro Val Ser
50                  55                  60

Val Lys Val Gly Asp Lys Val Leu Leu Pro Glu Tyr Gly Gly Thr Lys
65                  70                  75                  80

Val Val Leu Asp Asp Lys Asp Tyr Phe Leu Phe Arg Asp Gly Asp Ile
                85                  90                  95

Leu Gly Lys Tyr Val Asp
            100
```

<210> SEQ ID NO 31
<211> LENGTH: 312
<212> TYPE: DNA
<213> ORGANISM: Artificial Sequence
<220> FEATURE:
<223> OTHER INFORMATION: Description of Artificial Sequence: Synthetic
      Gly-Cpn10, extra N-terminal Gly residue
<220> FEATURE:
<221> NAME/KEY: CDS
<222> LOCATION: (1)..(309)
<223> OTHER INFORMATION: Gly-Cpn10

<400> SEQUENCE: 31

```
atg ggt gcg ggc cag gcg ttt cgt aaa ttt ctg ccg ctg ttt gat cgt      48
Met Gly Ala Gly Gln Ala Phe Arg Lys Phe Leu Pro Leu Phe Asp Arg
1               5                   10                  15 gtg ctg gtt gaa cgt agc gcg gcg gaa acc gtg acc aaa ggc ggc att      96
Val Leu Val Glu Arg Ser Ala Ala Glu Thr Val Thr Lys Gly Gly Ile
            20                  25                  30 atg ctg ccg gaa aaa agc cag ggc aaa gtg ctg cag gcg acc gtg gtt    144
Met Leu Pro Glu Lys Ser Gln Gly Lys Val Leu Gln Ala Thr Val Val
            35                  40                  45 gcg gtt ggc agc ggc agc aaa ggc aaa ggc ggc gaa att cag ccg gtg    192
Ala Val Gly Ser Gly Ser Lys Gly Lys Gly Gly Glu Ile Gln Pro Val
50                  55                  60 agc gtg aaa gtg ggc gat aaa gtg ctg ctg ccg gaa tat ggc ggc acc    240
Ser Val Lys Val Gly Asp Lys Val Leu Leu Pro Glu Tyr Gly Gly Thr
65                  70                  75                  80 aaa gtg gtg ctg gat gat aaa gat tat ttt ctg ttc cgc gat ggc gat    288
Lys Val Val Leu Asp Asp Lys Asp Tyr Phe Leu Phe Arg Asp Gly Asp
                85                  90                  95 att ctg ggc aaa tat gtg gat tga                                    312
Ile Leu Gly Lys Tyr Val Asp
            100
```

<210> SEQ ID NO 32
<211> LENGTH: 10
<212> TYPE: PRT
<213> ORGANISM: Artificial Sequence
<220> FEATURE:
<223> OTHER INFORMATION: Description of Artificial Sequence: Synthetic
      Cpn10 (wild-type) N-terminal sequence

<400> SEQUENCE: 32

```
Met Ala Gly Gln Ala Phe Arg Lys Phe Leu
1               5                   10
```

-continued

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      X-Cpn10 (wild-type) N-terminal sequence

<400> SEQUENCE: 33

Ala Gly Gln Ala Phe Arg Lys Phe Leu
1               5

<210> SEQ ID NO 34
<211> LENGTH: 294
<212> TYPE: DNA
<213> ORGANISM: Escherichia coli
<220> FEATURE:
<223> OTHER INFORMATION: Bacterial homolog of Cpn10 (GroES)
<220> FEATURE:
<221> NAME/KEY: CDS
<222> LOCATION: (1)..(291)
<223> OTHER INFORMATION: Cpn10 (GroES)

<400> SEQUENCE: 34 atg aat att cgt cca ttg cat gat cgc gtg atc gtc aag cgt aaa gaa      48
Met Asn Ile Arg Pro Leu His Asp Arg Val Ile Val Lys Arg Lys Glu
1               5                   10                  15 gtt gaa act aaa tct gct ggc ggc atc gtt ctg acc ggc tct gca gcg      96
Val Glu Thr Lys Ser Ala Gly Gly Ile Val Leu Thr Gly Ser Ala Ala
            20                  25                  30 gct aaa tcc acc cgc ggc gaa gtg ctg gct gtc ggc aat ggc cgt atc     144
Ala Lys Ser Thr Arg Gly Glu Val Leu Ala Val Gly Asn Gly Arg Ile
        35                  40                  45 ctt gaa aat ggc gaa gtg aag ccg ctg gat gtg aaa gtt ggc gac atc     192
Leu Glu Asn Gly Glu Val Lys Pro Leu Asp Val Lys Val Gly Asp Ile
    50                  55                  60 gtt att ttc aac gat ggc tac ggt gtg aaa tct gag aag atc gac aat     240
Val Ile Phe Asn Asp Gly Tyr Gly Val Lys Ser Glu Lys Ile Asp Asn
65                  70                  75                  80 gaa gaa gtg ttg atc atg tcc gaa agc gac att ctg gca att gtt gaa     288
Glu Glu Val Leu Ile Met Ser Glu Ser Asp Ile Leu Ala Ile Val Glu
                85                  90                  95 gcg taa                                                              294
Ala

<210> SEQ ID NO 35
<211> LENGTH: 102
<212> TYPE: PRT
<213> ORGANISM: Artificial Sequence
<220> FEATURE:
<223> OTHER INFORMATION: Description of Artificial Sequence: Synthetic
      Ala-Cpn10-IFI, extra N-terminal Ala residue, IFI tripeptide
      replaces IML tripeptide in mobile loop

<400> SEQUENCE: 35

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Ile Phe
            20                  25                  30

Ile Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

```
Val Lys Val Gly Asp Lys Val Leu Leu Pro Glu Tyr Gly Gly Thr Lys
 65                  70                  75                  80

Val Val Leu Asp Asp Lys Asp Tyr Phe Leu Phe Arg Asp Gly Asp Ile
                 85                  90                  95

Leu Gly Lys Tyr Val Asp
            100
```

<210> SEQ ID NO 36
<211> LENGTH: 312
<212> TYPE: DNA
<213> ORGANISM: Artificial Sequence
<220> FEATURE:
<223> OTHER INFORMATION: Description of Artificial Sequence: Synthetic
      Ala-Cpn10-IFI, extra N-terminal Ala residue, IFI
      tripeptide replaces IML tripeptide in mobile loop
<220> FEATURE:
<221> NAME/KEY: CDS
<222> LOCATION: (1)..(309)
<223> OTHER INFORMATION: Ala-Cpn10-IFI

<400> SEQUENCE: 36

```
atg gca gca gga caa gcg ttt aga aag ttt ctt cca ctc ttt gac cga     48
Met Ala Ala Gly Gln Ala Phe Arg Lys Phe Leu Pro Leu Phe Asp Arg
 1               5                  10                  15 gta ttg gtt gaa agg agt gct gct gaa act gta acc aaa gga ggc att     96
Val Leu Val Glu Arg Ser Ala Ala Glu Thr Val Thr Lys Gly Gly Ile
             20                  25                  30 ttc att cca gaa aaa tct caa gga aaa gta ttg caa gca aca gta gtc    144
Phe Ile Pro Glu Lys Ser Gln Gly Lys Val Leu Gln Ala Thr Val Val
         35                  40                  45 gct gtt gga tcg ggt tct aaa gga aag ggt gga gag att caa cca gtt    192
Ala Val Gly Ser Gly Ser Lys Gly Lys Gly Gly Glu Ile Gln Pro Val
     50                  55                  60 agc gtg aaa gtt gga gat aaa gtt ctt ctc cca gaa tat gga ggc acc    240
Ser Val Lys Val Gly Asp Lys Val Leu Leu Pro Glu Tyr Gly Gly Thr
 65                  70                  75                  80 aaa gta gtt cta gat gac aag gat tat ttc cta ttt aga gat ggt gac    288
Lys Val Val Leu Asp Asp Lys Asp Tyr Phe Leu Phe Arg Asp Gly Asp
                 85                  90                  95 att ctt gga aag tac gta gac tga                                    312
Ile Leu Gly Lys Tyr Val Asp
            100
```

<210> SEQ ID NO 37
<211> LENGTH: 102
<212> TYPE: PRT
<213> ORGANISM: Artificial Sequence
<220> FEATURE:
<223> OTHER INFORMATION: Description of Artificial Sequence: Synthetic
      Ala-Cpn10-III, extra N-terminal Ala residue, III tripeptide
      replaces IML tripeptide in mobile loop

<400> SEQUENCE: 37

```
Ala Ala Gly Gln Ala Phe Arg Lys Phe Leu Pro Leu Phe Asp Arg Val
 1               5                  10                  15

Leu Val Glu Arg Ser Ala Ala Glu Thr Val Thr Lys Gly Gly Ile Ile
             20                  25                  30

Ile Pro Glu Lys Ser Gln Gly Lys Val Leu Gln Ala Thr Val Val Ala
         35                  40                  45

Val Gly Ser Gly Ser Lys Gly Lys Gly Gly Glu Ile Gln Pro Val Ser
     50                  55                  60

Val Lys Val Gly Asp Lys Val Leu Leu Pro Glu Tyr Gly Gly Thr Lys
 65                  70                  75                  80
```

```
Val Val Leu Asp Asp Lys Asp Tyr Phe Leu Phe Arg Asp Gly Asp Ile
                85                  90                  95

Leu Gly Lys Tyr Val Asp
            100

<210> SEQ ID NO 38
<211> LENGTH: 312
<212> TYPE: DNA
<213> ORGANISM: Artificial Sequence
<220> FEATURE:
<223> OTHER INFORMATION: Description of Artificial Sequence: Synthetic
      Ala-Cpn10-III, extra N-terminal Ala residue, III
      tripeptide replaces IML tripeptide in mobile loop
<220> FEATURE:
<221> NAME/KEY: CDS
<222> LOCATION: (1)..(309)
<223> OTHER INFORMATION: Ala-Cpn10-III

<400> SEQUENCE: 38 atg gca gca gga caa gcg ttt aga aag ttt ctt cca ctc ttt gac cga      48
Met Ala Ala Gly Gln Ala Phe Arg Lys Phe Leu Pro Leu Phe Asp Arg
1               5                   10                  15 gta ttg gtt gaa agg agt gct gct gaa act gta acc aaa gga ggc att      96
Val Leu Val Glu Arg Ser Ala Ala Glu Thr Val Thr Lys Gly Gly Ile
            20                  25                  30 ata att cca gaa aaa tct caa gga aaa gta ttg caa gca aca gta gtc     144
Ile Ile Pro Glu Lys Ser Gln Gly Lys Val Leu Gln Ala Thr Val Val
        35                  40                  45 gct gtt gga tcg ggt tct aaa gga aag ggt gga gag att caa cca gtt     192
Ala Val Gly Ser Gly Ser Lys Gly Lys Gly Gly Glu Ile Gln Pro Val
    50                  55                  60 agc gtg aaa gtt gga gat aaa gtt ctt ctc cca gaa tat gga ggc acc     240
Ser Val Lys Val Gly Asp Lys Val Leu Leu Pro Glu Tyr Gly Gly Thr
65                  70                  75                  80 aaa gta gtt cta gat gac aag gat tat ttc cta ttt aga gat ggt gac     288
Lys Val Val Leu Asp Asp Lys Asp Tyr Phe Leu Phe Arg Asp Gly Asp
                85                  90                  95 att ctt gga aag tac gta gac tga                                     312
Ile Leu Gly Lys Tyr Val Asp
            100

<210> SEQ ID NO 39
<211> LENGTH: 110
<212> TYPE: PRT
<213> ORGANISM: Artificial Sequence
<220> FEATURE:
<223> OTHER INFORMATION: Description of Artificial Sequence: Synthetic
      Ala-Cpn10-EEE-cHis, extra N-terminal Ala residue, EEE
      tripeptide replaces IML tripeptide in mobile loop,
      C-terminal hexahistidine His tag

<400> SEQUENCE: 39

Ala Ala Gly Gln Ala Phe Arg Lys Phe Leu Pro Leu Phe Asp Arg Val
1               5                   10                  15

Leu Val Glu Arg Ser Ala Ala Glu Thr Val Thr Lys Gly Gly Glu Glu
            20                  25                  30

Glu Pro Glu Lys Ser Gln Gly Lys Val Leu Gln Ala Thr Val Val Ala
        35                  40                  45

Val Gly Ser Gly Ser Lys Gly Lys Gly Gly Glu Ile Gln Pro Val Ser
    50                  55                  60

Val Lys Val Gly Asp Lys Val Leu Leu Pro Glu Tyr Gly Gly Thr Lys
65                  70                  75                  80
```

```
Val Val Leu Asp Asp Lys Asp Tyr Phe Leu Phe Arg Asp Gly Asp Ile
             85                  90                  95

Leu Gly Lys Tyr Val Asp Leu Glu His His His His His His
            100                 105                 110

<210> SEQ ID NO 40
<211> LENGTH: 336
<212> TYPE: DNA
<213> ORGANISM: Artificial Sequence
<220> FEATURE:
<223> OTHER INFORMATION: Description of Artificial Sequence: Synthetic
      Ala-Cpn10-EEE-cHis, extra N-terminal Ala residue, EEE
      tripeptide replaces IML tripeptide in mobile loop,
      C-terminal hexahistidine His tag
<220> FEATURE:
<221> NAME/KEY: CDS
<222> LOCATION: (1)..(333)
<223> OTHER INFORMATION: Ala-Cpn10-EEE-cHis

<400> SEQUENCE: 40 atg gca gca gga caa gcg ttt aga aag ttt ctt cca ctc ttt gac cga      48
Met Ala Ala Gly Gln Ala Phe Arg Lys Phe Leu Pro Leu Phe Asp Arg
 1                5                  10                  15 gta ttg gtt gaa agg agt gct gct gaa act gta acc aaa gga ggc gaa      96
Val Leu Val Glu Arg Ser Ala Ala Glu Thr Val Thr Lys Gly Gly Glu
             20                  25                  30 gag gaa cca gaa aaa tct caa gga aaa gta ttg caa gca aca gta gtc     144
Glu Glu Pro Glu Lys Ser Gln Gly Lys Val Leu Gln Ala Thr Val Val
         35                  40                  45 gct gtt gga tcg ggt tct aaa gga aag ggt gga gag att caa cca gtt     192
Ala Val Gly Ser Gly Ser Lys Gly Lys Gly Gly Glu Ile Gln Pro Val
     50                  55                  60 agc gtg aaa gtt gga gat aaa gtt ctt ctc cca gaa tat gga ggc acc     240
Ser Val Lys Val Gly Asp Lys Val Leu Leu Pro Glu Tyr Gly Gly Thr
 65                  70                  75                  80 aaa gta gtt cta gat gac aag gat tat ttc cta ttt aga gat ggt gac     288
Lys Val Val Leu Asp Asp Lys Asp Tyr Phe Leu Phe Arg Asp Gly Asp
                     85                  90                  95 att ctt gga aag tac gta gac ctc gag cac cac cac cac cac cac tga     336
Ile Leu Gly Lys Tyr Val Asp Leu Glu His His His His His His
            100                 105                 110

<210> SEQ ID NO 41
<211> LENGTH: 110
<212> TYPE: PRT
<213> ORGANISM: Artificial Sequence
<220> FEATURE:
<223> OTHER INFORMATION: Description of Artificial Sequence: Synthetic
      Ala-Cpn10-cHis, extra N-terminal Ala residue, C-terminal
      hexahistidine His tag

<400> SEQUENCE: 41

Ala Ala Gly Gln Ala Phe Arg Lys Phe Leu Pro Leu Phe Asp Arg Val
 1               5                  10                  15

Leu Val Glu Arg Ser Ala Ala Glu Thr Val Thr Lys Gly Gly Ile Met
             20                  25                  30

Leu Pro Glu Lys Ser Gln Gly Lys Val Leu Gln Ala Thr Val Val Ala
         35                  40                  45

Val Gly Ser Gly Ser Lys Gly Lys Gly Gly Glu Ile Gln Pro Val Ser
     50                  55                  60

Val Lys Val Gly Asp Lys Val Leu Leu Pro Glu Tyr Gly Gly Thr Lys
 65                  70                  75                  80

Val Val Leu Asp Asp Lys Asp Tyr Phe Leu Phe Arg Asp Gly Asp Ile
```

85                  90                  95
Leu Gly Lys Tyr Val Asp Leu Glu His His His His His His
                100                 105                 110

<210> SEQ ID NO 42
<211> LENGTH: 336
<212> TYPE: DNA
<213> ORGANISM: Artificial Sequence
<220> FEATURE:
<223> OTHER INFORMATION: Description of Artificial Sequence: Synthetic
      Ala-Cpn10-cHis, extra N-terminal Ala residue, C-terminal
      hexahistidine His tag
<220> FEATURE:
<221> NAME/KEY: CDS
<222> LOCATION: (1)..(333)
<223> OTHER INFORMATION: Ala-Cpn10-cHis

<400> SEQUENCE: 42 atg gca gca gga caa gcg ttt aga aag ttt ctt cca ctc ttt gac cga      48
Met Ala Ala Gly Gln Ala Phe Arg Lys Phe Leu Pro Leu Phe Asp Arg
1               5                   10                  15 gta ttg gtt gaa agg agt gct gct gaa act gta acc aaa gga ggc att      96
Val Leu Val Glu Arg Ser Ala Ala Glu Thr Val Thr Lys Gly Gly Ile
            20                  25                  30 atg ctt cca gaa aaa tct caa gga aaa gta ttg caa gca aca gta gtc     144
Met Leu Pro Glu Lys Ser Gln Gly Lys Val Leu Gln Ala Thr Val Val
        35                  40                  45 gct gtt gga tcg ggt tct aaa gga aag ggt gga gag att caa cca gtt     192
Ala Val Gly Ser Gly Ser Lys Gly Lys Gly Gly Glu Ile Gln Pro Val
    50                  55                  60 agc gtg aaa gtt gga gat aaa gtt ctt ctc cca gaa tat gga ggc acc     240
Ser Val Lys Val Gly Asp Lys Val Leu Leu Pro Glu Tyr Gly Gly Thr
65                  70                  75                  80 aaa gta gtt cta gat gac aag gat tat ttc cta ttt aga gat ggt gac     288
Lys Val Val Leu Asp Asp Lys Asp Tyr Phe Leu Phe Arg Asp Gly Asp
                85                  90                  95 att ctt gga aag tac gta gac ctc gag cac cac cac cac cac cac tga     336
Ile Leu Gly Lys Tyr Val Asp Leu Glu His His His His His His
                100                 105                 110

<210> SEQ ID NO 43
<211> LENGTH: 291
<212> TYPE: DNA
<213> ORGANISM: Artificial Sequence
<220> FEATURE:
<223> OTHER INFORMATION: Description of Artificial Sequence: Synthetic
      Cpn10-NtermES, including initiating Met, including E. coli
      bacterial homolog of Cpn10 (GroES) N-terminus
<220> FEATURE:
<221> NAME/KEY: CDS
<222> LOCATION: (1)..(288)
<223> OTHER INFORMATION: Cpn10-NtermES

<400> SEQUENCE: 43 atg aat att cgt cca ctc ttt gac cga gta ttg gtt gaa agg agt gct      48
Met Asn Ile Arg Pro Leu Phe Asp Arg Val Leu Val Glu Arg Ser Ala
1               5                   10                  15 gct gaa act gta acc aaa gga ggc att atg ctt cca gaa aaa tct caa      96
Ala Glu Thr Val Thr Lys Gly Gly Ile Met Leu Pro Glu Lys Ser Gln
            20                  25                  30 gga aaa gta ttg caa gca aca gta gtc gct gtt gga tcg ggt tct aaa     144
Gly Lys Val Leu Gln Ala Thr Val Val Ala Val Gly Ser Gly Ser Lys
        35                  40                  45 gga aag ggt gga gag att caa cca gtt agc gtg aaa gtt gga gat aaa     192
Gly Lys Gly Gly Glu Ile Gln Pro Val Ser Val Lys Val Gly Asp Lys

```
                        50                 55                    60
gtt ctt ctc cca gaa tat gga ggc acc aaa gta gtt cta gat gac aag        240
Val Leu Leu Pro Glu Tyr Gly Gly Thr Lys Val Val Leu Asp Asp Lys
 65                  70                  75                  80 gat tat ttc cta ttt aga gat ggt gac att ctt gga aag tac gta gac        288
Asp Tyr Phe Leu Phe Arg Asp Gly Asp Ile Leu Gly Lys Tyr Val Asp
                 85                  90                  95 tga                                                                    291

<210> SEQ ID NO 44
<211> LENGTH: 309
<212> TYPE: DNA
<213> ORGANISM: Homo sapiens
<220> FEATURE:
<223> OTHER INFORMATION: Human X-Cpn10 (wild-type)
<220> FEATURE:
<221> NAME/KEY: CDS
<222> LOCATION: (1)..(306)
<223> OTHER INFORMATION: X-Cpn10

<400> SEQUENCE: 44 atg gca gga caa gcg ttt aga aag ttt ctt cca ctc ttt gac cga gta         48
Met Ala Gly Gln Ala Phe Arg Lys Phe Leu Pro Leu Phe Asp Arg Val
 1               5                  10                  15 ttg gtt gaa agg agt gct gct gaa act gta acc aaa gga ggc att atg         96
Leu Val Glu Arg Ser Ala Ala Glu Thr Val Thr Lys Gly Gly Ile Met
             20                  25                  30 ctt cca gaa aaa tct caa gga aaa gta ttg caa gca aca gtc gtc gct        144
Leu Pro Glu Lys Ser Gln Gly Lys Val Leu Gln Ala Thr Val Val Ala
         35                  40                  45 gtt gga tcg ggt tct aaa gga aag ggt gga gag att caa cca gtt agc        192
Val Gly Ser Gly Ser Lys Gly Lys Gly Gly Glu Ile Gln Pro Val Ser
 50                  55                  60 gtg aaa gtt gga gat aaa gtt ctt ctc cca gaa tat gga ggc acc aaa        240
Val Lys Val Gly Asp Lys Val Leu Leu Pro Glu Tyr Gly Gly Thr Lys
 65                  70                  75                  80 gta gtt cta gat gac aag gat tat ttc cta ttt aga gat ggt gac att        288
Val Val Leu Asp Asp Lys Asp Tyr Phe Leu Phe Arg Asp Gly Asp Ile
                 85                  90                  95 ctt gga aag tac gta gac tga                                            309
Leu Gly Lys Tyr Val Asp
            100

<210> SEQ ID NO 45
<211> LENGTH: 6
<212> TYPE: PRT
<213> ORGANISM: Artificial Sequence
<220> FEATURE:
<223> OTHER INFORMATION: Description of Artificial Sequence: Synthetic
      C-terminal hexahistidine His tag

<400> SEQUENCE: 45

His His His His His His
 1               5

<210> SEQ ID NO 46
<211> LENGTH: 4
<212> TYPE: PRT
<213> ORGANISM: Artificial Sequence
<220> FEATURE:
<223> OTHER INFORMATION: Description of Artificial Sequence: Synthetic
      E. coli GroES N-terminal residues 1-4

<400> SEQUENCE: 46
```

```
Met Asn Ile Arg
1

<210> SEQ ID NO 47
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Gly Ala Gly Gln Ala
1               5
```